(12) United States Patent
Yao et al.

(10) Patent No.: US 7,371,927 B2
(45) Date of Patent: May 13, 2008

(54) METHODS FOR MODULATING PLANT GROWTH AND BIOMASS

(75) Inventors: Jia-Long Yao, Auckland (NZ); Charles Ampomah-Dwamena, Auckland (NZ)

(73) Assignee: Arborgen, LLC, Summerville, SC (US)

( * ) Notice: Subject to any disclaimer, the term of this patent is extended or adjusted under 35 U.S.C. 154(b) by 260 days.

(21) Appl. No.: 10/899,942

(22) Filed: Jul. 27, 2004

(65) Prior Publication Data

US 2005/0044591 A1 Feb. 24, 2005

Related U.S. Application Data

(60) Provisional application No. 60/502,573, filed on Sep. 12, 2003, provisional application No. 60/490,846, filed on Jul. 28, 2003.

(51) Int. Cl.
*C12N 15/82* (2006.01)

(52) U.S. Cl. ................................. 800/290; 800/287

(58) Field of Classification Search .................. 800/290
See application file for complete search history.

(56) References Cited

U.S. PATENT DOCUMENTS 6,518,487 B1  2/2003  Lowe et al.

FOREIGN PATENT DOCUMENTS

WO    WO 99/22002       5/1999
WO    WO 01/96579 A1   12/2001

OTHER PUBLICATIONS

Zhou Y et al. The plant cyclin-dependent kinase inhibitor ICK1 has distinct functional domains for in vivo kinase inhibition, protein instability and nuclear localization. Plant J. Aug. 2003;35(4):476-89.*
Cockcroft CE et al. Cyclin D control of growth rate in plants. Nature. Jun. 1, 2000;405(6786):575-9.*
Schnittger A. et al. Ectopic D-type cyclin expression induces not only DNA replication but also cell division in Arabidopsis trichomes. Proc Natl Acad Sci U S A. Apr. 30, 2002;99(9):6410-5.*
Hill M.A. et al. Functional analysis of conserved histidines in ADP-glucose pyrophosphorylase from Escherichia coli. Biochem Biophys Res Commun. Mar. 17, 1998;244(2):573-7.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*
Schnittger A. et al. (Ectopic D-type cyclin expression induces not only DNA replication but also cell division in Arabidopsis trichomes. Proc Natl Acad Sci U S A. Apr. 30, 2002;99(9):6410-5).*
de Veylder L. et al. Genbank Accession No. AJ131636, Apr. 24, 1999.*
Vandepoele, Klass, et al., "Genome-Wide analysis of Core Cell Cycle Genes in Arabidopsis", The Plant Cell, Apr. 2002, pp. 903-916, vol. 14, American Society of Plant Biologists.
Chen, Yun-Chia Sophia and McCormick, Sheila, "*sidecar pollen*, an *Arabidopsis thaliana* male gametophytic mutant with aberrant cell divisions during pollen development", Development, 1996, pp. 3243-3253, vol. 22, printed in Great Britain, The company of Biologists Limited 1996.
Yang, Ming, et al., "Characterization of a *cytokinesis* defective (cyd1) mutant of *Arabidopsis*", Journal of Experimental Botany, Sep. 1999, pp. 1437-1446, vol. 50, No. 338, Oxford University Press 1999.
Jacqmard, Annie, et al., "Cell Division and Morphological Changes in the Shoot Apex of *Arabidopsis thaliana* during Floral Transition", Annals of Botany, 2003, pp. 571-576, vol. 91, Annals of Botany Company 2003.
Freeman et al., "Helianthus tuberosus cyclin D1 (CycD1;1) mRNA," complete cds, Dec. 1, 2002 (GenBank Accession No. AY063460), pp. 402-445 and 477-589.
Kim et al., "Arabidopsis thaliana Atlg70210 mRNA," complete cds, Mar. 14, 2003 (GenBank Accession No. BT005315), pp. 395-423.
Joubes et al, "CDK-related protein kinases in plants," *Plant Molecular Biology*, 43 (5-6) pp. 607-620 (see PubMed abstract).
Kramer, et al., "Molecular Evolution of Genes Controlling Petal and Stamen Development: Duplication and Divergence Within the *Apetala3* and *Pistillata* MADS-Box Gene Lineages", Genestics (1998) pp. 765-783, vol. 149.
Hill, et al., "Discrete spatial and temporal *cis*-acting elements regulate transcription of the *Arabidopsis* floral homeotic gene *APETALA3*", Development, (1998), pp. 1711-1721, vol. 125.

* cited by examiner

*Primary Examiner*—Cynthia Collins
(74) *Attorney, Agent, or Firm*—Foley & Lardner LLP

(57) ABSTRACT

This application discloses methods for modulating plant growth and biomass comprising stably incorporating into the genome of the plant a genetic construct comprising a gene promoter that is active in wood-forming tissues, a polynucleotide sequence encoding polypeptide regulators of cell division and a gene termination sequence.

4 Claims, 12 Drawing Sheets
(8 of 12 Drawing Sheet(s) Filed in Color)

Figure 9

MIKWHDLYAVLVAVVPLYVAMILAYGSVRWWRIFSPDQCSGINRFVAIFAVPLLSFHFISTNDPYRMNL
RFIAADTLQKLLLLLLLALWANLHRRGSLDWSITVFSLSTLPNTLVMGIPLLGAMYGTEASNLMVQVVV
LQCIIWYTLLLFLFEYRGAKILIMEQFPETAASIVSFNVDPDVVSLDGRNFLETDAEVGQDGKLHVTVR
KSNASRRSFGLGPGGGGSFSGMTPRPSNLSGVEIYSLSSSRNLTPRGSNSDFYSIMGVPRLSNFGPSDA
YSVQSSRGPTPRPSNFDENLQPSPKFGFYPAQVASAPYPAPIPDFASAFAKSGKPNQQQQQPAPAPPEQ
QSNGAAKANSYDAKELHMFVWSSSASPVSEVGGLHVFGSGDFGAPDNQSRRADHSVKEIRMMVADNNQP
NGETKTAPETTGFTGQDQFNFVAKADERDEGTGGEKEAAGPDRPNKLCASSSAGEPGGYGGGDDAGNDK
QMPPASVMTRLILIMVWRKLIRNPNTYSSLIGIIWSLIAFRWDVGMPEIVDKSIHILSDAGLGMAMFSL
GLFMALQPKLIACGNSVATFAMAVRFLVGPAAMAIASAAIGLRGPLLHIAIVQAALPQGIVPFVFAKEY
NVHPAVLSTMVIFGMLIALPITLVYYILLGL

Figure 10

MITGSDFYHVMTAMVPLYVAMILAYGSVRWWRIFTPDQCSGINRFVALFAVPLLSFHFISSNNPFTMNL
RFLAADSLQKLLILLALALWSHLSRRGSLDWSITLFSLSTLPNTLVMGIPLLRGMYGPYSGDLMVQIVV
LQCIIWYTLMLFLFEFRAARTLISNQFPGTAAASIISIRVDPDVVSACTDPRQSLETEAEVGSDGKLRV
TVRRSSASRSDIFKPAAWLSPRPSNLTNAEIYSLQSSRNPTPRGSSFNHAELYSVAA*GLGGGGRGSNFG*
*SADVYGLSAPFGPTPRPSNYEEDKPKFPYGSGGSTAGSYPAPNPGMFSPKNNGGSGGKRANVQGGKRGA*
*EDGGGGG*RRDLHMFVWSSSTSPVSDVFGNNHDLPTGATHEKVDQNHIKEGDQLERDEFSFRNRRPENVE
AGGGDAMPPTSVMTRLILIMVWRKLIRNPNTYSSLIGITWSLVSFRWHIEMPAIIAKSISILSDAGLGM
AMFSLGLFMALQPKIIACGNSVATFAMAVRFLTGPAVMAAASLVIGLRGDLLRVAIVQAALPQGIVPFV
FAKEYGLHPDILSTAVIFGMLIALPITLVYYIFLGI

Figure 11

MGSKEICRNELRIAVRQLSDRCLYSASKWAAEQLVGIELDPVKFTPSNTRFQRGSSSIRRRFRTNEIMS
TPIAGVSYVSTPVMEEDDIVDGDFYLLAKSYFDCREYRRAAHVLRDQYGKKAVFLRCYALYLAGENRKD
EENIELEGPLGKSDAVNKELVSLERELSMLRKNGSIDPFGLYLYGLVLKEKGSEHLARNLLVESVNSYP
WNWSAWSELQSLCTTIDILHSLPLNNHWMKDFFLAGAYQELRMHNESLAKYEYLQGTFSFSNYIQAQIA
KAQYSLREFEQVEVIFEELLRNDPYRVEDMDMYSNVLYAKECFSALSYLAHRVFMTDKYRPESCCIIGN
YYSLKGQHEKSVMYFRRALKLNKNCLSAWTLMGHEYVEMKNTPAAVDAYRRAVDINPCDYRAWYGLGQA
YEMMGMPFYALHYFRKSVFLQPSDSRLWIAMAQCYETEQLHMLEESIKCYRRAANCNDREAIALHKLAK
LHCELGRLEEAAFYYKKDLERMEAEERDGPNMVEALLFLATHGKDQKRFEEAEVYCTRLLDYTGPEKET
AKSLLRGMRMAQSGFPSMSAEHFPP

Figure 12

MDQIE[YSEKYYDDTYEYRHVELPP]DVARLLPKNRLLTENEWRGIGVQQSRGWVHYAIHCSEPHIMLFRR
PLNYEQNHQHPEPHIMLFRRPLNCQPNHQPQAHHPT

Figure 13

MPQIQ[YSEKYTDDTYEYRHVVLPP]ETAKLLPKNRLLNENEWRAIGVQQSRGWVHYAIHRPEPHIMLFRR
PLNYQQNQQQQAGAQSQPMGLKAQ

Figure 14

MGCVCAKQSDILGEPESPKVKGSNLASSRWSVSSETKQLPQHSDSGILHHQHYYHPRDESDEAKLKESN
YGGSKRRTRQGRDPADLDMGIFVRTPSSQSEAELVAAGWPAWMAAFAGEAIHGWIPRRAESFEKLYKIG
QGTYSNVYKARDLDNGKIVALKKVRFDSLDAESVRFMAREILVLRKLDHPNIVKLEGLVTSEVSSSLYL
VFEYMEHDLAGLAACPGIKFTEPQVKCYMQQLLQGLDHCHRHGVLHRDIKGSNLLIDNGGILKIADFGL
ATFFYPDQKQLLTSRVVTLWYRPPELLLGATDYGVAVDIWSAGCILAELLAGKPILPGRTEVEQLHKIF
KLCGSPSEDYWKESKLPHATIFKPQHPYKSCIAEAFKDFSPSALALLETLLAIEPGHRGEASGALKSEF
FTTEPLSCDPSSLPKYPPSKEFDAKLRAQETRRQRDVGVRGHGSEAARRTSRLSRAGPTPNEGAELTAL
TQKQHSTSHATSNIGSEKPSTKKEDYTAGLHIDPPRPVNHSYETTGVSRAYDAIRGVAYSGPLSQTHVS
GSTSGKKPKRDHVKGLSGQSSLQPSKPFIVSDSRSERIYEKSHVTDLSNHSRLAVGRNRDTTDPHKSLS
TLMQQIQDGTLDGIDIGTHEYARAPVSSTKQKSAQLQRPSTLKYVDNVQLQNTRVGSRQSDERPANKES
DMVSHRQGQRIHCSGPLLHPSANIEDLLQKHEQQIQQAVRRAHHGKREALSNKSSLPGKKPVDHRAWVS
SGKGNKESPYFKGKGNKELSDLKGGPTAKVTNFRQKVM

Figure 15

MATSGNKNINAKLVLLGDVGAGKSSLVLRFVKGQFVEFQESTIGAAFFSQTLAVNDATVKFEIWDTAGQ
ERYHSLAPMYYRGAAAAIIVYDMTNLASFERAKKWVQELQAQGNPNMVMALAGNKADLLDARKVTAEEA
QTYAQEHGLFFMETSAKTAANVNDIFYEIAKRLPRAQPAPNPSGMVLMDRPAERTAAASCCS

Figure 16

MSEIRRKLVIVGDGACGKTCLLIVFSKGTFPEVYVPTVFENYVADVVVDGKRVELALWDTAGQEDYDRL
RPLSYPDSHVILICFAVDSPDSLDNVQEKWISEVLHFCSGLPIILVGCKKDLRHDPKTVDELRRTSQRP
VTSQEGDSVRQKIGATRYLECSAKTGEGVREVFEQATRLALLSQKGGKGGKKGKCTVL

Figure 17

MSYDYLFKYIIIGDTGVGKSCLLLQFTDKRFQPVHDLTIGVEFGARMVTIDGRPIKLQIWDTAGQESFR
SITRSYYRGAAGALLVYDITRRDTFNHLASWLEDARQHANPNMTIMLIGNKSDLSHRRAVTKEEGEQFA
KENGLLFLEASARTAQNVEEAFVKTAAQILQNIQDGVFDVSNETSGIKVGYGRPQGQAGARDGAVAQRG
GCCS

Figure 18

MVDSFDEECDYLFKAVLTGDSAVGKSNLLSRFARKEFQLDSKPTIGVEFAYRNVKVADKLIKAQIWDTA
GQERFRAITSSYYRGALGALLVYDITRRVTFENVKKWLRELRDFGNPDMVVVLVGNKSDLSNSREVDLE
EGKDFAEAENLCFMETSALENLNVEEAFLEMITRIHEITSQKSLEAKNNEITSSLHGPKQVIQIDEVTA
TKKSYCCSI

Figure 19

MSGPGAIRRKLVIVGDGACGKTSLLCVFAMGEFPKEYEPTIFENYVAEIRLDGKPVQLALWDTAGQEEY
ERLRPLSYSKAHVILIAFAIDTPDSLENVSVKWIEEVRNICGPQTPVILVGCKADLRPASGSSADGRQY
VTRQRAQAVAQEIGARAYKECSALNNQGVDDVFEAATRASMIVREVKPEADEEHRGGCCVLC

Figure 20

MAMVQRQGHDPSSPQEQEDGPSSFLSDDALYCEEGRFEEDDGGGGGQVDGIPLFPSQPADRQQDSPWAD
EDGEEKEEEAELQSLFSKERGARPELAKDDGGAVAARREAVEWMLMVRGVYGFSALTAVLAVDYLDRF
LAGFRLQRDNRPWMTQLVAVACLALAAKVEETDVPLLVELQEVGDARYVFEAKTVQRMELLVLSTLGWE
MHPVTPLSFVHHVARRLGASPHHGEFTHWAFLRRCERLLVAAVSDARSLKHLPSVLAAAAMLRVIEEVE
PFRSSEYKAQLLSALHMSQEMVEDCCRFILGIAETAGDAVTSSLDSFLKRKRRCGHLSPRSPSGVIDAS
FSCDDESNDSWATDPPSDPDDNDDLNPLPKKSRSSSPSSSPSSVPDKVLDLPFMNRIFEGIVNGSPI

Figure 21

MSVSISNCFSDLLCQEDSSGVLSGESLGCSSDLDSPACVEESIAVFIKDERHFVPDYDCLSRFQSPSLD
AAARLDSVAWILKVQAYYGFQPLTAYLSVNYLDRFLCSRRLPQTNGWPLQLLSVACLSLAAKMEEPLVP
ALLDLQVEGAKYIFEPRTICRMELLVLRVLDWRLRSVTPFNFIAFFACKLDPSGDFMGFLISRATEIII
SNIREVIFLEYWPSCIAAAALLCAANEVPNLSVVNPEHAESWCSGLRKENIIGCYRLMQEIVLDSCRIE
SPKILPQFRVTVRTRMRSSDLSPYSSSSSSSSSPNKRRKLNQSLWVDDDKDNPEE

Figure 22

MSISSSEDCFIDSHLLCDEDSSDILSGESPEYSSDLESPASSEDSIASFIEDERHFVPGIDYLSRFHSQ
SLDSSARADSVAWILKVQAYYGFQPLTAYLSVNYLDRFLYSRRLPETNGWPLQLLSVACLSLAAKMEEP
LVPSFLDLQIEGAKYIFEPRTIRRMELLVLATLDWRLRSVTPFSFIGFFAYKVDPTGTFSSFLISRSTE
IILSNIRDASFLEYWPSCIAAAALLCAANEIPNLTLLNPEHAESWCNGLSKDKIVGCYRLMQPSTSESG
RRKPPKVIPQLRVRIRAGLRYSNSSSSSSSTRLGYKRRKLNNCLWVEEDDKENSKFRAEE

Figure 23

MSVSISNCFSNLLCQEDSSGVFSGESPGCSSDLESPACVEESISVFIKNERHFVPDYDCFSRFQSPSLD
AAARLDSIAWILKVQAYYGFQPLTAYLSVNYLDRFLCSRRLPQSNGWPLQLLSVACLSLAAKMEEPLVP
ALLDLQVEGAKYIFEPRTICRMELLVLRVLDWRLRSVTPFNFIAFFAYKLDPSGDFIEFLISRATEIIL
SHIREVIFLEYWPSCIAAAALLCAANEVQSLSVVNPEHAESWCNGLRKENIMGCYRLMQEIVLDNTRRK
SPKILPQYRVTVRTRMRSSDLSSSYSSSSSSSSSSPNKRRKLNQTHLWVHEDKGNNTEE

Figure 24

MAPSFDLAVTNLLCAEENCIFDDNDDDECLVAPYVLTSNGFQSWRHGGGHGGDGLPFTSDECLIEMVEK
ETHHLPVDGYLMKLQNGELDVGARKDAVDWIEQVSARFNFGPLCTYLAVNYMDRFLSAYTLPKGKAWTM
QLLAVACLSLAAKLEETEVPISLDLQVGGSKFVFEARTIERMELLVLTTLGWRMQAVTPFSFIDHYLCK
IHHDDKTSIARSIHLLLNIIQGIEFLEFKPSEIAAAVAISVAGEGEETAIPLLIQQKLHMERVVKCIKL
VKEMSGKTEEEESRSMSEGPQSPSGVLNVRCLSYKSNESTAVGSCANSSSHHNSSNGSKRRRLNRPCEV
EL

Figure 25

MALPDDEAQVQEIETQSYVLDALFCEDLCCDEDFDGNGTVEDSDYWETLRKDQPFLAINLLEKDPLWED
DEELQSLISKEEQTHVCNASVTSDGYLIQARNEALSWIFSVKHYYAFSAFTSLLAVNYFDRFVSNVRFQ
RDKPWMSQLAAVACLSLAAKVEETQVPLLLDLQVVESKFLFEAKTIQRMELLVLSALQWKMHPVTPFSF
LRHIIRRLPLKDHMLWELLGRFQSHLLSIIADHRFLCYLPSVLATATILHIINEIEPCNFLEYQNELLS
VLKINKNHLDECYKVILDSLGSNGSVNSYQMCGLGSPRDVMDGYFISDSSNDSWPMVPSISP

Figure 26

MAMHRYEPADDEAQTHLISLDSLFCEEEKWEEEEEDEDELEQTHQAHVFSLDVLEEDLFGEDERLLSLL
SKETEQLKQSNLKLEPLLMDPSVSAARSSSVEWMLKVKSHYGFSSLTAILAVAYFDRFLSSFHFRSDKP
WMNQLVAVTCLSLAAKVEEVEVPLLLDLQVEDAKFVFEAKTIQRMELLVLSTLQWRMHLVTSYSYLDNI
VRRLGLKTNLHLEFFKRSENLLLSLLSDSRFVGYLPSVLASATMMNIIEQIEPHKSMEHQDHLLGVLKM
SKDKVLGCYNLVVEHSKACSNGLYHSNNPHKRKYEHHQAPDSPNGVIDAGFSSDSSNDSWALRAAASVC
SSPEPSFKKNKTEEPRMLYHSLNRRVCLDIVGSPS

Figure 27

MAMHRFEQSDHEAQTHLISLDSLYCEEEKWEDGEDGVDDEIEQAHEINQTHLFSLGFFEENLFEEDERL
RSLLSKETEQLEQSNLDLEALLMDPSVSAARSSAVEWMLKVKSHYGFSTLTAIMAVSYFDRFLLSFHYK
SDKPWMNQLVAVTCLSLAAKVEEIHVPLLLDLQVEDAEYVFEAKTIQRMELLVLSTLQWRMHFVTPFSF
LDHIVKRLGFKANLQLEFLRCSEHLLLSMLSDSRFVGYLPSVLATATMMKVIDHIEPHESLEHQDQLLG
VLKMSKEKVQCCYNLVVEHSKAYGNNGFYHLNNPYKRKHEHHHQAPYSPSGVIDAGFSSDSSNDSWALR
ASSSVCSSPESSFKKTKTEEPNLKFHPLNRVFLDIVGSPS

METHODS FOR MODULATING PLANT GROWTH AND BIOMASS

CROSS-REFERENCE TO RELATED APPLICATIONS

This application claims priority to U.S. Provisional Patent Application No. 60/490,846, filed Jul. 28, 2003, and U.S. Provisional Patent Application No. 60/502,573, filed Sep. 12, 2003.

FIELD OF THE INVENTION

This invention relates to isolated plant polynucleotides encoding cell cycle proteins and their methods of use for genetically manipulating plant growth and form.

BACKGROUND

The cell cycle plays an essential role in the regulation of growth and development of eukaryotes. While there are similarities in the core molecular machinery of cell cycling in animals, plants and yeast, there are aspects of cell cycle regulation that are unique to plants.

The cells of a plant are surrounded by rigid cell walls and, as a consequence, are relatively immobile compared with animal cells and yeast. Plant environmental cues such as light, temperature, nutritional and osmotic stresses, gravity, and wounding play significant roles in initiating and controlling plant growth, and the cell division cycle is responsive to these cues. Cell division, cell expansion and cell death all play important roles in plant growth and architecture. All of the cells of a plant arise from meristematic tissues which form in the early embryo and continue to proliferate and participate in organ formation during the lifetime of the plant. Mature non-proliferative differentiated plant cells remain totipotent and can be induced to resume proliferation and regenerate entire plants under appropriate culture conditions.

Two cell cycles, the cell division cycle and the endoreduplication cycle, are operative in plants and each plays specific roles in the development of plant form. The plant division cycle involves cell growth, DNA replication and mitosis, and is subject to environmental controls (e.g., plant hormones, nutrients and light) which control the rate and orientation of cell division in response to changes in the environment, and local and global pattern controls, which are involved in morphogenesis (Meijer and Murray, *Curr. Opin. Plant Biol.* 4:44-49 (2001)). The endoreduplication cycle is a foreshortened cell cycle in which cell growth and DNA synthesis continue in the absence of mitosis. Many plant species exhibit endoploidy (i.e., greater than diploid genomic DNA content) (see Kondorosi et al., *Curr. Opin. Plant Biol.* 3:488-492 (2000) (review)). In some plants, endoploidy is restricted to certain cells or tissues, whereas in others, it is exhibited in all or most cell types. Plant cells can exit the mitotic cycle and enter the endocycle in a regulated manner (Cebolla et al., *EMBO J.* 18: 4476-4484 (1999)). Endocycling is common in differentiated plant cells and is closely linked to cell differentiation and control of cell size (Nagl, W. *Endopolyploidy and Polyteny in Differentiation and Evolution: Towards an Understanding of Quantitative and Qualitative Variation of Nuclear DNA in Ontogeny and Phylogeny* (North-Holland, N.Y., 1978)). Endocycling is implicated in the regulation of gene expression in functionally specialized cells.

The basic features of cell cycle regulation are common to all eukaryotes. The cell division cycle is divided into four distinct phases: S phase (DNA synthesis), M phase (mitosis), G1 (the gap before S phase) and G2 (the gap after S phase). These events are repeated in the sequence G1, S, G2 and M for each round of cell division.

The cell cycle is driven by the formation of protein complexes containing cyclins and cyclin-dependent protein kinases (CDK) which regulate the G1-to-S and G2-to-M transitions (Mironov et al., *Plant Cell* 11: 509-521 (1999); Forsburg and Nurse, *Annu. Rev. Cell Biol.* 7: 277-256 (1991); Norbury and Nurse, *Annu. Rev. Biochem.* 61: 441-470 (1992); Nasmyth, *Trends in Genetics* 12: 405-412 (1996)). These are the key checkpoints for controlling cell cycle progression. The binding of cyclin to CDK is necessary for protein kinase activity and for determining target specificity (Nigg, *BioEssays* 17: 471-480 (1995); Morgan, *Nature* 374: 131-134 (1995)). Several classes of plant CDKs have been identified (see Tables 1 and 2 in Mironov et al., 1999)). These can be distinguished by differences in their transcription patterns during the cell cycle, their cyclin binding motifs, and their biological activities. Different cyclin-CDK complexes control different stages of cell-cycle progression. D-type cyclins induce CDK activity after stimulation by growth regulators and transduce extracellular signals for stimulation of cell division (Riou-Khamlichi et al., *Science* 283:1541-1544 (1999); Fuerst et al., *Plant Physiol.* 112: 1023-1033 (1996); De Veylder et al., *Planta* 208:452-462 (1999)). The activity of CDKs is positively regulated by CDK-activating kinase (CAK) and negatively regulated by CDK inhibitors (CKIs) (Inze et al., *Plant Cell* 11:991-994 (1999); Umeda et al., *Proc. Natl. Acad. Sci. USA* 97:13396-13400 (2000); Wang et al., Plant J. 15:501-510 (1998); Wang et al., *Nature* 386:451-452 (1997)).

CDKs phosphorylate a wide range of substrates including retinoblastoma (Rb) proteins that are repressors of cell cycle transcription factors of the E2F family. Rb acts by binding to and negatively regulating E2F transcription factors that are required for transcription of genes involved in DNA replication and progression of the cell cycle (Inze et al., (1999) Ibid.; Dynlacht, *Nature* 389:149-153 (1997); De Jager and Murray, *Plant Mol. Biol.* 41:295-299 (1999)). Rb is inactive when phosphorylated by a CDK. Plant D cyclins have been shown to be able to bind retinoblastoma-related proteins (Nakagami et al., *Plant J.* 18:243-252 (1999); Ach et al., *Mol. Cell. Biol.* 17:5077-5086 (1997)) and also together with Cdc2 phosphorylate a Rb-related protein (Nakagami et al., Ibid.). It is proposed that progression through S phase is controlled by cyclin A kinases, and that entry of cells from G2 into mitosis is controlled by the expression of B-type cyclins and activation of cyclin B-CDK complexes. During M phase, mitotic cyclins are degraded by anaphase-promoting complex (APC) and the kinase complexes deactivated thereby facilitating cells exit from mitosis. Down-regulation of mitotic cyclins and/or inhibition of mitotic CDK/cyclin complexes prior to the M-phase transition point induces endoreduplication. Overexpression of a prereplicative complex involved in initiation of DNA replication in S-phase has been shown to induce endoreduplication in leaf cells (reviewed by Meijer and Murray, *Curr. Opin. Plant Biology* 4:44-49 (2001); Meeting Report, "Cross-Talk" between Cell division Cycle and Development in Plants", *The Plant Cell* 14:11-16 (2002)).

In addition to the core cell cycle genes described above, other genes have been implicated as regulators of cell division and cell expansion. These genes include the peptidyl prolyl cis/trans isomerases (PPIases) (Vittorioso et al., Mol. Cell. Biol. 18:3034-3043, 1998), G-protein (Ullah et al., 2001, *Science* 292:2066-2069), MAP kinase (Jouannic et al., 2001, *Plant J.* 26:637-649) and histone acetyltransferase (Howe et al., *Genes Dev.* 15:3144-3154 (2001)). Systematic analysis of the genes in chromosome III of *C. elegans* using RNAi technology has identified 133 genes that are required for proper cell division in the worm embryos (Gonczy et al., 2000, *Nature* 408:331-336). An analysis of 6000 yeast gene deletion lines has identified 500 genes involved in cell division and cell size control (Jorgensen et al., 2002, *Science* 297:395-400).

Peptidyl prolyl cis/trans isomerases (PPIases) catalyze the energetically unfavorable and intrinsically slow process of cis/trans isomerization of peptide bonds to amino-terminal to a proline (Hunter, 1998, *Cell* 92:141-143). Of the three structurally distinct families of PPIases that have been identified thus far, there is evidence that the highly conserved Pin1-type proteins (Lu et al., *Nature* 380:544-547 (1996)) are essential for cell survival.

As an essential mitotic regulator in budding yeast and HeLa cells, Pin1 binds to a defined subset of phosphoproteins, many of which are also recognized by the mitosis- and phospho-specific monoclonal antibody MPM-2 (Yaffe et al., 1997, *Science* 278:1957-1960)). Furthermore, Pin1 regulates the functions of its binding proteins, including inhibiting the mitosis-promoting activity of Cdc25C (Shen et al., 1998, *Genes Dev.* 12: 706-720). Depletion or mutations of Pin1 induce premature mitotic entry and mitotic 20 arrest in yeast, HeLa cells, and *Xenopus* egg extracts (Lu et al., 1996, *Nature* 380:544-547; Hani et al., 1999, *J. Biol. Chem.* 274:108-116; Winkler et al., 2000, *Science* 287: 1644-1647; Crenshaw et al., 1998, *EMBO J.* 17:1315-1327; Shen et al., 1998, ibid.). Pin1 is also required for the replication checkpoint in *Xenopus* extracts (Winkler et al., 2000, ibid.).

Recently, plant homologs of the Pin1-type PPIases have been reported. Plant Pin1 homologs, such as AtPin1 of *Arabidopsis* (Landrieu et al., 2000, *J. Biol. Chem.* 275: 10577-10581) and MdPin1 of apple (Yao et al., 2001, *J. Biol. Chem.* 276:13517-13523), lack an $NH_2$-terminal WW domain but have significant homology to the PPIase domain of Pin1. In the standard protease-coupled PPIase assay, MdPin1 exhibits the same phosphorylation-specific substrate specificity, as is the case for human Pin1. Interestingly, like Pin1, both MdPin1 and AtPin1 are able to rescue the lethal mitotic phenotype of a temperature-sensitive mutation in the Pin1 homologue ESS1/PTF1 gene in *S. cerevisiae* (Yao et al., 2001, *J. Biol. Chem.* 276:13517-13523). However, it has not been described whether AtPin1 has any role in plant cell cycle progression and plant development.

The genetic manipulation of cell cycle genes in plants holds great promise for engineering improvements in traits of agronomic importance, such as wood growth and quality, fruit size and crop yield. The growth of fruit, wood and most plant organs reflect changes in cell proliferation (cell division) and expansion (endoreduplication). Wood, the xylem tissue of trees, is derived from cells generated by the cambial meristem through cell division. The cells derived from cambium undergo a significant increase in size before they differentiate into mature xylem cells with thick secondary cell walls. Endoreduplication is responsible for this increase in cell volume.

The growth of a fruit after anthesis starts by stimulation of cell divisions in the tissues forming the fruit flesh. The cell division activity is usually restricted to an initial period of fruit development, followed by cell expansions that make the greatest contribution to the final fruit size. The length of cell division phase during fruit development varies among plant species, for example, it is seven to ten days in tomato and approximately four weeks in apple. During cell expansion in fruit tissue, there are repeated cycles of DNA synthesis without intervening cell divisions (endoreduplications) resulting in endopolyploid cells.

The relation between cell division and plant development is very complex and still not well understood (Hemerly et al., 1999, *BioEssays* 21: 29-37). In order to reliably predict the effects of transgenic modification of plants with cell cycle regulatory genes, a better understanding of how cell cycle regulation is integrated with morphogenesis and plant adaptation to environmental changes.

Nevertheless, experiments have been reported which suggest the possibility of modulating plant growth by transgenic expression of cell cycle genes without adverse effects on plant development and morphogenesis. For example, transgenic tobacco plants that express the *Arabidopsis* CDC2a gene carrying a dominant negative mutation, which reduces the number of cell divisions, contained fewer cells but exhibited normal morphogenesis (Hemerly et al., 1995, *EMBO J.* 14:3925-3936). Increased expression of Cyc1At under the control of Cdc2aAt promoter in transgenic *Arabidopsis* plants produces plants with longer roots containing an increased number of cells (Doerner et al., 1996, *Nature* 280:520-523). Transgenic tobacco plants that over-express a D-type cyclin gene (cycD2At) show elevated overall growth rates, an increased rate of leaf initiation and accelerated development at all stages from seedling to maturity, but normal cell size. Cells within the shoot apical meristem had a faster division rate due to a reduction in the length of the G1 phase of the cell cycle (Cockcroft et al., *Nature* 405: 575-579 (2000)).

SUMMARY OF THE INVENTION

The present invention provides isolated polynucleotide sequences from plants that encode polypeptides involved in the regulation of cell size and cell proliferation. The polynucleotide sequences are provided in SEQ ID NO: 1-12, 16-22, 46-47 and 59 of the Sequence Listing. The predicted polypeptide sequences encoded by SEQ ID NO. 1-12, 16-22, 46-47 and 59 are respectively SEQ ID NO: 27-45, 48-49 and 60 of the Sequence Listing. The polynucleotide sequences can be used to modulate plant phenotypes and to produce modified plants with novel or improved traits, such as changes in: plant height and biomass; size or numbers of leaves; length and thickness of shoots; length, thickness and branching of roots; seed production per plant; flowering; numbers and sizes of cells in tissues, including wood-forming tissues; and development of plant reproductive organs. In addition, it is expected that certain of the sequences can be used to increase the transformation efficiency and regeneration of transgenic plants.

The present invention also provides recombinant genetic constructs comprising one or more of the inventive polynucleotide sequences and transgenic plant cells comprising these constructs. Certain of the constructs are recombinant expression cassettes in which the expression of the inventive sequence is controlled by a plant-functional promoter. Transgenic host cells comprising an expression construct can be used to regenerate transgenic plants that express the inventive polynucleotide sequences.

In another of its aspects, the invention provides methods of modifying a plant phenotype by introducing an isolated polynucleotide sequence identified herein as encoding a cell cycle regulator into the plant for expression in the plant. These methods involve transforming the plant with one or more genetic constructs comprising one or more polynucleotide sequences selected from the group consisting of sequences identified as SEQ ID NO. 1-13, 16-23, 26, 46-47 and 59, and expressing the sequences under the control of a constitutive or regulatable promoter (e.g., a tissue- or organ-specific promoter or an inducible promoter). In certain preferred embodiments, the transformed cell type or tissue is involved in wood formation, plant reproduction, the formation of storage organs or fruit production.

In one of the preferred embodiments, combinations of cell cycle genes that encode proteins of multiprotein complexes are expressed together in a developing plant to enhance cell proliferation and plant growth beyond what is achievable by expressing a single gene.

In still another preferred embodiment, a plant Pin1 gene is expressed under the control of the AP3 promoter, or a homologous promoter, preferably a promoter that is active early in the development of male and/or female reproductive tissues, such that plant reproductive development is modified. Presently preferred sequences are selected from the group consisting of sequences recited in SEQ ID NO: 23, 26, 46, and 47 of the Sequence Listing.

In another preferred embodiment, the expression of a cell cycle gene or genes is used to facilitate plant regeneration, increase transformation efficiency, and provide positive selection means for identifying transformants.

In yet another of its aspects, the invention provides a method for increasing the yield of a product of a biosynthetic pathway that is operative in a plant tissue of interest, comprising stably transforming the genome of the plant with one or more of the polynucleotide sequences disclosed herein. In one embodiment, the plant is cotransformed with an isolated AMP 1 or AMP 1-related D cyclin sequence whose expression results in an amplification of cell number and a sequence that encodes a transcriptional regulator or a biosynthetic enzyme involved in the pathway. Preferably, transgene expression is controlled by a promoter that is selectively active in the tissue where the pathway is operative. In a particularly preferred embodiment, a CycD polynucleotide sequence is expressed in plant xylem in combination with a sequence encoding an enzyme involved the production of cell wall materials, such as lignin and high crystalline cellulose in wood.

The invention also encompasses methods of producing plants with novel phenotypes and plants produced by these methods.

In yet another aspect, the present invention provides isolated sequences of cell cycle polypeptides from *Eucalyptus, Pine, Lolium* and *Cucurbit* species. The polypeptides can be used to screen for antagonists and agonists of biological functions of cell cycle proteins (e.g., protein-protein interactions, enzymatic activity) and for producing specific antibodies that are useful for expression analysis, purification of cell cycle proteins and multiprotein complexes thereof, and for screening expression libraries.

BRIEF DESCRIPTION OF FIGURES

The patent or application file contains at least one drawing executed in color. Copies of this patent or patent application publication with color drawings will be provided by the Office upon request and payment of necessary fee.

FIG. 9. Amino acid sequence given in SEQ ID NO: 27. The conserved auxin carrier domain is underlined.

FIG. 10. Amino acid sequence given in SEQ ID NO: 28. The conserved auxin carrier domain is underlined. A Gly-rich region is in bold/italics.

FIG. 11. Amino acid sequence given in SEQ ID NO: 29. The conserved tetratricopeptide repeats (TPR) are underlined.

FIG. 12. Amino acid sequence given in SEQ ID NO: 30. The conserved cyclin-dependent kinase domain is underlined and the cyclin-dependent kinases regulatory subunits signature 1 is boxed.

FIG. 13. Amino acid sequence given in SEQ ID NO: 31. The conserved cyclin-dependent kinase domain is underlined and the cyclin-dependent kinases regulatory subunits signature 1 is boxed.

FIG. 14. Amino acid sequence given in SEQ ID NO: 32. The conserved eukaryotic serine/threonine protein kinase domain is underlined and the serine/threonine protein kinases active-site signature is boxed.

FIG. 15. Amino acid sequence given in SEQ ID NO: 33. The conserved Ras GTPase superfamily is underlined.

FIG. 16. Amino acid sequence given in SEQ ID NO: 34. The conserved Ras GTPase superfamily is underlined.

FIG. 17. Amino acid sequence given in SEQ ID NO: 35. The conserved Ras GTPase superfamily is underlined.

FIG. 18. Amino acid sequence given in SEQ ID NO: 36. The conserved Ras GTPase superfamily is underlined.

FIG. 19. Amino acid sequence given in SEQ ID NO: 37. The conserved Ras GTPase superfamily is underlined.

FIG. 20. Amino acid sequence given in SEQ ID NO: 38. The conserved cyclin domain is underlined.

FIG. 21. Amino acid sequence given in SEQ ID NO: 39. The conserved N-and C-terminal domains are underlined.

FIG. 22. Amino acid sequence given in SEQ ID NO: 40. The conserved N-and C-terminal domains are underlined.

FIG. 23. Amino acid sequence given in SEQ ID NO: 41. The conserved N-and C-terminal domains are underlined.

FIG. 24. Amino acid sequence given in SEQ ID NO: 42. The conserved N-and C-terminal domains are underlined.

FIG. 25. Amino acid sequence given in SEQ ID NO: 43. The conserved N-and C-terminal domains are underlined.

FIG. 26. Amino acid sequence given in SEQ ID NO: 44. The conserved N-and C-terminal domains are underlined.

FIG. 27. Amino acid sequence given in SEQ ID NO: 45. The conserved N-and C-terminal domains are underlined.

DETAILED DESCRIPTION

Figure 1:
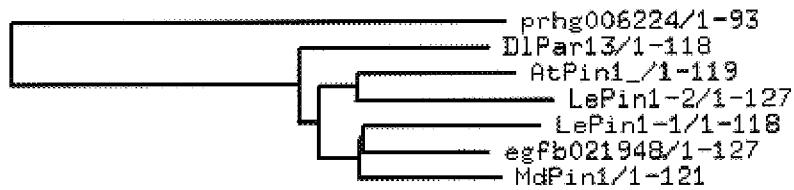
FIG. 1. Alignment of amino acid sequences (A) and a phylogenetic tree of plant Pin1 genes (B). The species and GENBANK accession numbers for these genes are described in Table 2. The SEQ ID NOS. of plant Pin1 genes shown in this Figure are provided in Tables 2 and 3, and in the Sequence Listing. The full-length amino acid sequences of these genes were aligned together using the CLUSTAL W (v1.75) multiple sequence alignment program. The tree was made based on this alignment using the Belvu program.

The polynucleotides of the present invention encode polypeptides that regulate cell size and cell reproduction. The polynucleotides can be used to modulate plant growth and architecture to produce modified plants with novel or improved traits, for example, plants with modifications in height and biomass; size or numbers of leaves; length and thickness of shoots; length, thickness and branching of roots; seed production per plant; flowering; numbers and sizes of cells in tissues, including wood-forming tissues; and development of plant reproductive organs. In addition, it is expected that certain of the sequences can be used to increase the transformation efficiency and regeneration of transgenic plants.

The present invention thus provides methods for modulating the polynucleotide and/or polypeptide content and composition of a plant, such methods involving stably incorporating into the genome of the organism a genetic construct comprising one or more polynucleotides of the present invention.

In related aspects, methods for producing a plant having an altered genotype or phenotype is provided, such methods comprising transforming a plant cell with a genetic construct of the present invention to provide a transgenic cell, and cultivating the transgenic cell under conditions conducive to regeneration and mature plant growth. Plants having an altered genotype or phenotype as a consequence of modulation of the level or content of a polynucleotide or polypeptide of the present invention compared to a wild-type organism, as well as components (seeds, etc.) of such plants, and the progeny of such plants, are contemplated by and encompassed within the present invention.

The isolated polynucleotides of the present invention also have utility in genome mapping, in physical mapping, and in positional cloning of genes. Additionally, the polynucleotide sequences identified as SEQ ID NOS: 1-12, 16-22, 46-47 and 59 and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be employed to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix Inc. (Santa Clara, Calif.).

In one of its aspects, the present invention provides isolated polynucleotides comprising a sequence selected from the group consisting of: (a) SEQ ID NO: 1-12, 16-22, 46-47 and 59; (b) complements of SEQ ID NO: 1-12, 16-22, 46-47, and 59; (c) reverse complements of SEQ ID NO: 1-12, 16-22, 46-47 and 59; (d) reverse sequences of SEQ ID NO: 1-12, 16-22, 46-47 and 59; (e) sequences encoding a polypeptide sequence selected from the group consisting of SEQ ID NO: 27-45, 48-49 and 60; (f) sequences that differ from the sequences recited above in (a)-(d) due to degeneracy of the genetic code; and variant sequences having at least 75%, 80%, 90%, 95% or 98% identity to a sequence of (a)-(d) above, the percentage identity being determined as described below.

The word "polynucleotide(s)," as used herein, means a polymeric collection of nucleotides, and includes DNA and corresponding RNA molecules and both single and double stranded molecules, including HnRNA and mRNA molecules, sense and anti-sense strands of DNA and RNA molecules, and comprehends cDNA, genomic DNA, and wholly or partially synthesized polynucleotides.

A polynucleotide of the present invention may be an entire gene or any portion thereof. As used herein, a "gene" is a DNA sequence that codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., *Methods in Enzymol.* 254(23): 363-375, 1995 and Kawasaki et al., *Artific. Organs* 20(8): 836-848, 1996.

Polynucleotides that comprise complements of such polynucleotide sequences, reverse complements of such polynucleotide sequences, or reverse sequences of such polynucleotide sequences, together with variants of such sequences, are also provided.

The definition of the terms "complement(s)," "reverse complement(s)," and "reverse sequence(s)," as used herein, is best illustrated by the following example. For the sequence 5' AGGACC 3', the complement, reverse complement, and reverse sequence are as follows:

```
complement          3' TCCTGG 5'
reverse complement  3' GGTCCT 5'
reverse sequence    5' CCAGGA 3'.
```

Preferably, sequences that are complements of a specifically recited polynucleotide sequence are complementary over the entire length of the specific polynucleotide sequence.

As used herein, the term "x-mer," with reference to a specific value of "x," refers to a polynucleotide comprising at least a specified number ("x") of contiguous residues of: any of the polynucleotides provided in SEQ ID NOS: 1-12, 16-22, 46-47 and 59. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NOS: 1-12, 16-22, 46-47 and 59, or their variants. Similarly, polypeptides of the present invention comprehend polypeptides comprising at least a specified number of contiguous residues (x-mers) of any of the polypeptides identified as SEQ ID NOS: 27-45, 48-49 and 60. According to preferred embodiments, the value of x is at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer, a 250-mer; or a 300-mer, 400-mer, 500-mer or 600-mer of a polynucleotide provided in SEQ ID NOS: 1-12, 16-22, 46-47 and 59, or a variant of one of the polynucleotides corresponding to the polynucleotides provided in SEQ ID NOS: 1-12, 16-22, 46-47 and 59. Polypeptides of the present invention include polypeptides comprising a 20-mer, a 40-mer, a 60-mer, an 80-mer, a 100-mer, a 120-mer, a 150-mer, a 180-mer, a 220-mer, a 250-mer; or a 300-mer, 400-mer, 500-mer or 600-mer of a polypeptide provided in SEQ ID NOS: 27-45, 48-49 and 60, or a variant thereof.

RNA sequences, reverse sequences, complementary sequences, anti-sense sequences and the like, corresponding to the polynucleotides of the present invention, may be routinely ascertained and obtained using the cDNA sequences identified as SEQ ID NOS: SEQ ID NOS: 1-12, 16-22, 46-47 and 59.

The polynucleotides sequences of the present invention, SEQ ID NO: 1-12, 16-22, 46-47 and 59, can be isolated by high throughput sequencing of cDNA libraries prepared from E. grandis, P. radiata, Lolium perenne and Cucurbits as described in Example 1 below. These sequences comprise full-length open reading frames which encode polypeptides that are involved in plant cell proliferation and growth, and non-translated regions of mRNA.

Alternatively, oligonucleotide probes and primers based on the sequences provided in SEQ ID NOS: 1-12, 16-22, 46-47 and 59 can be synthesized as detailed below, and used to identify positive clones in either cDNA or genomic DNA libraries from Eucalyptus, Pine, Lolium and Cucurbit tissue cells by means of hybridization or polymerase chain reaction (PCR) techniques. Hybridization and PCR techniques suitable for use with such oligonucleotide probes are well known in the art (see, for example, Mullis et al., Cold Spring Harbor Symp. Quant. Biol., 51:263, 1987; Erlich, ed., PCR technology, Stockton Press: NY, 1989; and Sambrook et al., eds., Molecular cloning: a laboratory manual, 2nd ed., CSHL Press: Cold Spring Harbor, N.Y., 1989). In addition to DNA-DNA hybridization, DNA-RNA or RNA-RNA hybridization assays are also possible. In the first case, the mRNA from expressed genes would then be detected instead of genomic DNA or cDNA derived from mRNA of the sample. In the second case, RNA probes could be used. Artificial analogs of DNA hybridizing specifically to target sequences could also be employed. Positive clones can be analyzed by using restriction enzyme digestion, DNA sequencing or the like.

The polynucleotides of the present invention may also, or alternatively, be synthesized using techniques that are well known in the art. The polynucleotides may be synthesized, for example, using automated oligonucleotide synthesizers (e.g., Beckman Oligo 1000M DNA Synthesizer; Beckman Coulter Ltd., Fullerton, Calif.) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Oligonucleotide probes and primers complementary to and/or corresponding to SEQ ID NOS: 1-12, 16-22, 46-47 and 59 and variants of those sequences, are also comprehended by the present invention. Such oligonucleotide probes and primers are substantially complementary to the polynucleotide of interest over a certain portion of the polynucleotide. An oligonucleotide probe or primer is described as "corresponding to" a polynucleotide of the present invention, including one of the sequences set out as SEQ ID NOS: 1-12, 16-22, 46-47 and 59 or a variant thereof, if the oligonucleotide probe or primer, or its complement, is contained within one of the sequences set out as SEQ ID NOS: 1-12, 16-22, 46-47 and 59 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length, preferably from about 10 to 50 base pairs in length, and more preferably from about 15 to 40 base pairs in length. The probes can be easily selected using procedures well known in the art, taking into account DNA-DNA hybridization stringencies, annealing and melting temperatures, potential for formation of loops, and other factors that are well known in the art. Preferred techniques for designing PCR primers are disclosed in Dieffenbach and Dyksler, PCR Primer: a laboratory manual, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

The isolated polynucleotides of the present invention also have utility in genome mapping, in physical mapping, and in positional cloning of genes.

The polynucleotides identified as SEQ ID NOS: 1-12, 16-22, 46-47 and 59 were isolated from cDNA clones and represent sequences that are expressed in the tissue from which the cDNA was prepared. Identification of genomic DNA and heterologous species DNA can be accomplished by standard DNA/DNA hybridization techniques, under appropriately stringent conditions, using all or part of a polynucleotide sequence as a probe to screen an appropriate library. Alternatively, PCR techniques using oligonucleotide primers that are designed based on known genomic DNA, cDNA and protein sequences can be used to amplify and identify genomic and cDNA sequences.

In another aspect, the present invention provides isolated polypeptides encoded by the above polynucleotides. As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide that comprises a partial isolated polynucleotide sequence provided herein. In specific embodiments, the inventive polypeptides comprise an amino acid sequence selected from the group consisting of SEQ ID NO: 27-45, 48-49 and 60, as well as variants of such sequences.

Thus, in a related aspect, the present invention provides variant polypeptides comprising a sequence having at least 75%, 80%, 90%, 95% or 98% identity to a sequence of SEQ ID NO: 27-45, 48-49 and 60, or functional fragment thereof.

The polynucleotides and polypeptides of the present invention have demonstrated similarity to the following polypeptides that are known to be involved in growth regulation pathways. The terms "cell cycle regulator" and "cell cycle regulatory gene" are used herein to refer generically to polynucleotide sequences that regulate cell size and/or cell proliferation, regardless of whether they function within the "cell division cycle", the "endoreduplication cycle", or in a related growth regulation pathway.

TABLE 1

| Polynucleotide SEQ ID NO: | Polypeptide SEQ ID NO: | Polypeptide Identity | Comments |
| --- | --- | --- | --- |
| 1, 2 | 27, 28 | Auxin transport | These molecules belong to the auxin transport protein family and contain a conserved auxin carrier domain. Members of the family are integral membrane proteins involved in auxin transport and transcriptional regulation of cell cycle machinery. |
| 3 | 29 | CDC23 | The molecule contains conserved tetratricopeptide repeats (TPR). |
| 4, 5 | 30, 31 | CKS1 | CDK subunit proteins (CKS) contain the conserved cyclin-dependent kinases regulatory subunit domain. Within this domain, the conserved cyclin-dependent kinases regulatory subunits signature 1 is present. CKS proteins are involved in mediating the interaction of CDKs with substrates and other regulatory proteins by acting as docking factors (Vandepoele et al., Plant Cell 14:903-916, 2002) |
| 6 | 32 | CRK1 Protein | CDC2-related kinase 1 (CRK1) proteins contain the conserved motif of eukaryotic protein kinases, which includes a conserved serine/threonine protein kinases active-site signature. The protein is involved in ATP binding and protein phosphorylation. |
| 7-11 | 33-37 | GTPase | GTPases belong to the Ras GTPase superfamily and contains the Ras GTPase superfamily conserved domain. |
| 12, 16-22, 59 | 38, 39-45, 60 | Cyclin D | Cyclin family members contain a conserved cyclin domain that is present in cyclins and retinoblastoma. It is a protein recognition domain that plays a role in cell-cycle and transcription control. |
| 46, 47 | 48, 49 | Pin1 | Peptidyl prolyl cis/trans isomerases (PPIase) play an important role in cell cycle regulation. Pin1 belongs to the PPIase family and is involved in mediating the protein-protein interactions. A PPiC-type peptidyl-prolyl cis-trans isomerase domain is present containing a conserved PPiC-type peptidyl-prolyl cis-trans isomerase signature. |

Polypeptide sequences were identified in part by comparisons with sequences in the EMBL nucleotide sequence database and the SwissProt protein sequence database. Conserved domains shown in FIGS. 9-27 were identified with InterProScan software Release v3.1, Nov. 6, 2001. The current InterPro database integrates PROSITE, PRINTS, Pfam, ProDom, SMART and TIGRFAMs databases. InterPro data is distributed in XML format and it is freely available under the InterPro Consortium copyright.

Polypeptides of the present invention may be produced recombinantly by inserting a polynucleotide sequence of the present invention encoding the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide molecule that encodes a recombinant polypeptide. Suitable host cells include prokaryotes, yeast, and higher eukaryotic cells. Preferably, the host cells employed are plant, *E. Coli*, insect, yeast, or a mammalian cell line such as COS or CHO. The polynucleotide sequences expressed in this manner may encode naturally occurring polypeptides, portions of naturally occurring polypeptides, or other variants thereof. The expressed polypeptides may be used in various assays known in the art to determine their biological activity. Such polypeptides may also be used to raise antibodies, to isolate corresponding interacting proteins or other compounds, and to quantitatively determine levels of interacting proteins or other compounds.

In a related aspect, polypeptides are provided that comprise at least a functional portion of a polypeptide having an amino acid sequence selected from the group consisting of sequences provided in SEQ ID NO: 27-45, 48-49 and 60 and variants thereof. As used herein, a "functional portion" of a polypeptide is a portion which is essential for mediating a biological function of the polypeptide, such as for example, a binding site required for protein-protein interactions, an active site of an enzyme (e.g., a GTPase or a kinase), a conserved protein recognition domain such as the domains that are described in Table 1 and shown in FIGS. 9-27 of this application, and the like. Functional portions of a polypeptide may be known in the art or identified by those of ordinary skill in the art using methods known in the art. Such methods include genetic analysis of mutants; in vitro mutagenesis of the polynucleotide sequence that encodes the polypeptide and subsequent expression analysis of the mutated sequence in a plant; testing of polypeptide fragments or mutant polypeptides for retention of biological activity using in vitro assays well known to those of skill in the art.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85: 2149-2146, 1963. Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, *Proc. Natl. Acad. Sci. USA* 82: 488-492, 1985). Sections of DNA sequences may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 75%, more preferably at least 80%, more preferably at least 90%, more preferably yet at least 95% and most preferably, at least 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100. See General Methods below for additional details.

Polynucleotides and polypeptides having a specified percentage identity to a polynucleotide or polypeptide identified in one of SEQ ID NO: 1-12, 16-22, 46-47, 59, 27-45, 48-49 and 60 thus share a high degree of sequence similarity. Variant polynucleotides and polypeptides preferably have additional structural and/or functional features in common with the polynucleotide and polypeptide sequences of the present invention. For example, polynucleotides having a specified degree of identity to, or capable of hybridizing to, a polynucleotide of the present invention preferably additionally have at least one of the following features: (1) an open reading frame, or partial open reading frame, encoding a polypeptide, or a functional portion of a polypeptide, having substantially the same functional properties as the polypeptide, or functional portion thereof, encoded by a polynucleotide in a recited SEQ ID NO. 1-12, 16-22, 46-47 and 59; or (2) they encode polypeptides having identifiable conserved domains in common.

According to one embodiment, "variant" polynucleotides and polypeptides, with reference to each of the polynucleotides and polypeptides of the present invention, preferably comprise sequences having the same number or fewer nucleotides or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being related to the polynucleotide or polypeptide of the present invention, measured as having an E value of 0.01 or less using the BLASTN or BLASTX algorithms set at the default parameters. According to a preferred embodiment, a variant polynucleotide is a sequence having the same number or fewer nucleic acids than a polynucleotide of the present invention that has at least a 99% probability of being related to the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being related as the polypeptide of the present invention, measured as having an E value of 0.01 or less using the BLASTP algorithm set at the default parameters.

The present invention also encompasses variant polynucleotides that differ from the disclosed sequences as a consequence of the discrepancy of the genetic code, but encode a polypeptide having a similar biological activity to a polypeptide encoded by a polynucleotide of the present invention.

Additionally, polynucleotides comprising sequences that differ from the polynucleotide sequences recited in SEQ ID NO: 1-12, 16-22, 46-47 and 59, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NO: 27-45, 48-49 and 60 as a result of amino acid substitutions, insertions, and/or deletions totaling less than 10% of the total sequence length are contemplated by and encompassed within the present invention, provided the variant polypeptide has activity in a flowering pathway.

In another aspect, the present invention provides recombinant genetic constructs comprising, in the 5'-3' direction, a gene promoter sequence; an open reading frame coding for at least a functional portion of a polypeptide of the present invention; and a gene termination sequence. The open reading frame may be orientated in either a sense or anti-sense direction. For applications where amplification of enzyme activity is desired, the open reading frame may be inserted in the construct in a sense orientation, such that transformation of a target organism with the construct will lead to an increase in the number of copies of the gene and therefore an increase in the amount of enzyme. When down-regulation of enzyme activity is desired, the open reading frame may be inserted in the construct in an anti-sense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, regulation may be achieved by inserting appropriate sequences or subsequences (e.g., DNA or RNA) in ribozyme constructs.

Genetic constructs comprising a non-coding region of a gene coding for a polypeptide of the present invention, or a nucleotide sequence complementary to a non-coding region, together with a gene promoter sequence and a gene termination sequence, are also provided. As used herein the term "non-coding region" includes both transcribed sequences that are not translated, and non-transcribed sequences within about 2000 base pairs 5' or 3' of the translated sequences or open reading frames. Examples of non-coding regions that may be usefully employed in the inventive constructs include introns and 5'-non-coding leader sequences. Transformation of a target plant with such a genetic construct may lead to a reduction in the amount of enzyme synthesized by the plant by the process of cosuppression, in a manner similar to that discussed, for example, by Napoli et al., *Plant Cell* 2:279-290, 1990; and de Carvalho Niebel et al., *Plant Cell* 7:347-358, 1995.

The genetic constructs of the present invention further comprise a gene promoter sequence and a gene termination sequence, operably linked to the polynucleotide to be transcribed, which control expression of the gene. The gene promoter sequence is generally positioned at the 5' end of the polynucleotide to be transcribed, and is employed to initiate transcription of the polynucleotide. Gene promoter sequences are generally found in the 5' non-coding region of a gene but they may exist in introns (Luehrsen, *Mol. Gen. Genet.* 225:81-93, 1991). When the construct includes an open reading frame in a sense orientation, the gene promoter sequence also initiates translation of the open reading frame. For genetic constructs comprising either an open reading frame in an anti-sense orientation or a non-coding region, the gene promoter sequence consists only of a transcription initiation site having a RNA polymerase binding site.

A variety of gene promoter sequences that may be usefully employed in the genetic constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or anti-sense RNA only in the tissue of interest. With genetic constructs employing inducible gene promoter sequences, the rate of RNA polymerase binding and initiation can be modulated by external physical or chemical stimuli, such as light, heat, anaerobic stress, alteration in nutrient conditions and the like. Temporally regulated promoters can be employed to effect modulation of the rate of RNA polymerase binding and initiation at a specific time during development of a transformed cell.

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original gene or from the target species to be transformed.

Other regulatory sequences may be included in the construct, such as transcriptional and translational enhancers.

The genetic constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds., *Methods for Plant Molecular Biology*, Academic Press Inc.: San Diego, Calif., 1988). Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., *Molecular cloning: a laboratory manual*, CSHL Press: Cold Spring Harbor, N.Y., 1989. The genetic construct of the present invention may be linked to a vector having at least one replication system, for example, *E. coli*, whereby after each manipulation, the resulting construct can be cloned and sequenced and the correctness of the manipulation determined.

Additional methodological details and references are provided in General Methods below.

The expression of polynucleotide sequences in target cells may be controlled by choice of the promoter sequence, or by selecting the number of functional copies or the site of integration of the polynucleotides incorporated into the genome of the target organism. A target plant may be transformed with more than one construct of the present invention, thereby modulating the growth, architecture, biomass and chemical composition of the plant by affecting the activity of more than one polypeptide, affecting polypeptide activity in more than one tissue or affecting polypeptide activity at more than one expression time. Similarly, a construct may be assembled containing more than one open reading frame coding for a polypeptide encoded by a polynucleotide of the present invention or more than one non-coding region of a gene coding for such polypeptide. The polynucleotides of the present invention may also be employed in combination with other known sequences encoding polypeptides involved in various metabolic and biosynthetic pathways. In this manner, more than one pathway may be modulated to produce a plant having an altered phenotype.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acid Res.* 12:8711-8721, 1984. Targets for the introduction of the DNA constructs of the present invention include tissues, such as leaf tissue, procambium, cambium, and xylem, disseminated cells, protoplasts, seeds, embryos, meristematic regions; cotyledons, hypocotyls, and the like. In certain preferred embodiments, the transformed cell type or tissue is involved in wood formation, plant reproduction, flowering, the formation of storage organs or fruit production. Transformation techniques which may be usefully employed in the inventive methods include those taught by Ellis et al., *Plant Cell Reports,* 8:16-20, 1989, Wilson et al., *Plant Cell Reports* 7:704-707, 1989; Tautorus et al., *Theor. Appl. Genet.* 78:531-536, 1989; and Ishida et al., *Nat. Biotechnol.* 14:745-750, 1996.

Plants which may be transformed using the inventive constructs include both monocotyledonous angiosperms (e.g., grasses, corn, grains, oat, wheat and barley) and dicotyledonous angiosperms (e.g., *Arabidopsis*, tobacco, legumes, alfalfa, oaks, *eucalyptus*, maple), and gymnosperms (e.g., Scots pine; see Aronen, *Finnish Forest Res. Papers*, Vol. 595, 1996), white spruce (Ellis et al., *Biotechnology* 11:84-89, 1993), larch (Huang et al., *In Vitro Cell* 27:201-207, 1991), and *Eucalyptus* (U.S. Provisional Patent Application No. 60/508,944, which is incorporated by reference herein in its entirety). See also references disclosed below in General Methods.

In a preferred embodiment, the inventive genetic constructs are employed to transform trees, shrubs and woody plants. Woody plants are herein defined as a tree or shrub whose stem lives for a number of years and increases in diameter each year by the addition of woody tissue. Preferably the woody plant is selected from the group consisting of *eucalyptus* and *pine* species, most preferably from the group consisting of *Eucalyptus grandis* and *Pinus radiata*. Other preferred species include Poplar, sugarcane, forage grasses and *Salix* spp. Other species which may be usefully transformed with the genetic constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana*; other gymnosperms, such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Juniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata*; and *Eucalypts*, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni*; and hybrids of any of these species.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. The resulting transformed plants may be reproduced sexually or asexually, using methods well known in the art, to give successive generations of transgenic plants.

Polynucleotides of the present invention may also be used to specifically suppress gene expression by methods that operate post-transcriptionally to block the synthesis of products of targeted genes, such as RNA interference (RNAi), and quelling. For a review of techniques of gene suppression see *Science*, 288:1370-1372, 2000. Exemplary gene silencing methods are also provided in WO 99/49029 and WO 99/53050. Posttranscriptional gene silencing is brought about by a sequence-specific RNA degradation process that results in the rapid degradation of transcripts of sequence-related genes. Studies have provided evidence that double-stranded RNA may act as a mediator of sequence-specific gene silencing (see, e.g., review by Montgomery and Fire, *Trends in Genetics,* 14: 255-258, 1998). Gene constructs that produce transcripts with self-complementary regions are particularly efficient at gene silencing. A unique feature of this posttranscriptional gene silencing pathway is that silencing is not limited to the cells where it is initiated. The gene-silencing effects may be disseminated to other parts of an organism and even transmitted through the germ line to several generations.

The polynucleotides of the present invention may be employed to generate gene silencing constructs and or gene-specific self-complementary RNA sequences that can be delivered by conventional art-known methods to plant tissues. Within genetic constructs, sense and antisense sequences can be placed in regions flanking an intron sequence in proper splicing orientation with donor and acceptor splicing sites, such that intron sequences are removed during processing of the transcript and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Specific ribonucleases bind to and cleave the double-stranded RNA, thereby initiating the cascade of events leading to degradation of specific mRNA gene sequences, and silencing specific genes. In a preferred embodiment, gene silencing RNA sequence constructs comprise tandem inverted- or direct-repeat sequences. Gene silencing constructs comprising the polynucleotides of the present invention, or portions thereof, are useful for creating genetically modified plants with desired phenotypes as well as for characterizing genes (e.g., in high-throughput screening of sequences), and studying their functions in intact organisms.

In another of its aspects, the invention provides methods of modifying a plant phenotype by introducing an isolated polynucleotide sequence identified herein as encoding a cell cycle regulator into the plant for expression in the plant. These methods involve transforming the plant with one or more genetic constructs comprising one or more polynucleotide sequences selected from the group consisting of sequences identified as SEQ ID NO. 1-13, 16-23, 26, 46 and 47 and 59, and expressing the sequences under the control of a constitutive or regulatable promoter (e.g., a tissue- or organ-specific promoter or an inducible promoter). In certain preferred embodiments, the transformed cell type or tissue is involved in wood formation, plant reproduction, the formation of storage organs or fruit production.

In a related aspect, the invention provides methods for modulating the cell division cycle in a plant, such methods including stably incorporating into the genome of the target plant a genetic construct comprising one or a combination of polynucleotide sequences of the present invention or an inventive polynucleotide sequence in combination with a known polynucleotide.

In a preferred embodiment, the construct comprises a cell cycle regulatory gene which, when expressed in the plant, alters the rate and/or extent of cell division throughout the plant, or in particular plant tissues or organs thereof, as compared with an unmodified plant (i.e., a plant that is not transgenically transformed with the cell cycle regulatory gene).

In another preferred embodiment, multiple cell cycle genes are expressed simultaneously to enhance cell proliferation over and above what is achieved by expressing a single gene. In particular, we envisage that over-expression of two or more genes encoding proteins of the same multiprotein complex (e.g. cyclin and CDK, E2F and DP, Cdc18/Cdc16 and Cdt1, and others) should give a higher level of enhancement in cell division, therefore a more profound improvement in plant growth, than the expression of a gene encoding one of the proteins of the complex. Without wishing to be bound by theory, we hypothesize that if the protein encoded by the gene forms part of a multiprotein assembly, the overexpression of that gene alone might not increase cell division unless the endogenous level of the expressed protein is the limiting factor in forming a functional complex. Thus, in certain instances, the levels of interacting proteins could limit the amount of the complex that forms and the extent of enhancement of cell division.

Multiprotein assemblies are an integral part of cell cycle regulation. The number and types of interactions between cell cycle proteins is potentially large (see, e.g., Kohn, *Molecular Biology of the Cell* 10:2703-2734 (1999), and the molecular interactions of individual cell cycle proteins may be competitive, cooperative or independent of one another. The formation, stability and activity of multiprotein assemblies are subject to multiple levels of regulation (e.g., gene transcription, covalent protein modification, controlled protein degradation, spatial and temporal localization and other processes (see, e.g., Pines, *Nature Cell Biology* 1:E73-79 (1999)). Complexes may exist in alternative states which are functionally different and interconvertible by covalent modifications.

Functional testing of candidate gene combinations can be carried out by stable or transient expression analysis in plant cells and tissues. The effects of the gene combinations on cell cycle progression can be assessed using cell and protoplast suspensions, or callus cultures or sections prepared from plant tissues of wild type and transformed plants which express the gene or genes of interest. Methods for analyzing cell division include measurement of mitotic index, DNA synthesis, and growth fraction analysis. Such methods are published and well known to those of skill in the art (see, e.g., G. P. Studzinski (Ed), Cell Growth and Apoptosis, A Practical Approach, IRL Press at Oxford University Press, 2995; R. Wieder, Chapter 1 in G. P. Studzinski (Ed.), Cell Growth, Differentiation and Senescence, Oxford University Press, 1999; and Jacqmard et al., *Ann. Botany* 91: 571-576 (2003) and references cited therein).

Cell cycle genes may be useful for increasing the efficiency of plant transformation and for regenerating transformed plants in hormone free medium. The effect of expressing different classes of cyclin genes on regeneration efficiency of shoots in hormone free media was tested in *N. benthamiana* leaf explants transformed with one of the following cell cycle genes: the *Arabidopsis* cyclin D4;1 (hereafter referred to as AMP1), AtCycD3;1 or AtCycD2;1. The explants were co-cultivated, then placed on media containing kanamycin (50 mg/l) but without hormone. Control explants were not co-cultivated and were placed on medium without kanamycin and without hormone.

The preliminary experiments summarized below indicate that by day 40 after co-cultivation, approximately 30% of the explants in medium without hormone regenerated shoots, whereas only one of the control explants regenerated a shoot on hormone-free medium. These results provide support for the suggestion that these genes and their orthologs may be useful as positive selection markers for transformed cells and may obviate or reduce the need for hormones during plant regeneration in culture.

| Construct code | Gene name | Medium | No. Explants | No. shoots regenerated | Regeneration efficiency |
|---|---|---|---|---|---|
| K10164 | AMP1 | kan, hormone free | 65 | 22 | 33.85% |
| K10167 | AtCycD3;1 | kan, hormone free | 65 | 19 | 29.23% |
| K10169 | AtCycD2;1 | kan, hormone free | 58 | 19 | 32.76% |
| Nil construct | Nil | hormone free | 45 | 1 | 2.22% |

Our approach differs from the uses of maize CycD in the maize transformation system. In that system, the overexpression of the CycD gene of maize reportedly increases transformation efficiency, and can be used to identify transgenic calli in the absence of additional selective markers (see U.S. Pat. No. 6,518,487).

In maize, somatic embryogenetic callus cells are used as the starting material for transformation. At the selection stage, the transformed cells are just required to divide (multiply) in order to form new calli which can be distinguished from the old non-transformed callus cells. The new calli are then transferred to a new medium for embryogenesis and plant production. A reliable somatic embryogenesis system is not available for many plant species. Most plant transformation systems employ organogenesis regeneration systems. In the case of N. benthamiana and Eucalyptus, leaf tissues are used as starting material for transformation. At the selection stage, the transformed cells are required both to divide and differentiate into shoot primordium for regeneration.

In organogenesis regeneration systems, transformation efficiency and regeneration of shoots should be increased by AMP1 overexpression in cells that are cultured in the presence of gibberellin (GA). Cells transformed with AMP1 are highly competent for division but are not very well expanded. GA can be used to promote cell expansion. While GA by itself is unlikely to promote regeneration from non-transformed cells, a combination of overexpression of AMP1 in the presence of GA should render the AMP1 transformed cells competent for both cell division and differentiation to regenerate shoots.

The present invention encompasses methods of using known plant Pin 1 genes, and novel tree homologs of Pin1 genes, such as those identified in FIG. 1 as egfb021948, a *Eucalyptus grandis* Pin 1 gene (SEQ ID NO: 46), and prhg006224, a Pin1-related gene from *Pinus radiata* (SEQ ID NO: 47), to modify floral development, eliminate pollen formation, and produce other traits of commercial importance in trees and other species of plants in which floral development patterns are conserved.

The specific biological roles of plant Pin1 homologs are poorly understood, and their potential uses for transgenic modification of plants have not been reported. The proposal that plant Pin1 homologs of animal and yeast Pin1 genes may act as cell cycle regulators was made by Yao et al., based on studies which showed that the Pin1 homologs from apple and *Arabidopsis* (MdPin1 and AtPin1) can rescue the lethal mitotic phenotype of a temperature sensitive (ts) Pin1 homolog in *S. cerevisiae*, and on Northern blot analysis of MdPin1 transcripts showing a correlation of MdPin1 gene transcription with cell division during apple fruit growth and in dividing apple suspension cell cultures (Yao et al., *J. Biol. Chem.* 276: 13571-13523 (2001)). To our knowledge, the effects of Pin1 expression in other plants have not been previously reported.

The results of experiments described below in Example 3 suggest that AtPin1 may interact with AP3, and possibly with other gene products as well, to control petal and stamen development (Example 3). The % identity of the *Pine* and *Eucalyptus* amino acid and nucleotide sequences to AtPin1 and several other known Pin1 sequences is shown below in Table 2 and Table 3 respectively. It is believed that these sequences can be used to modify floral development, eliminate pollen formation, and produce other traits of commercial importance in trees and other species of plants in which floral development patterns are conserved. Tree promoter homologs of AP3 have been identified which are expressed in petals and stamens of *Arabidopsis* (see, e.g., Molecular Biology of Woody Plants (S. M. Jain and S. C. Minocha (Eds.), vol. 1, 135-153, Kluwer Academic Publishers, 2000)). These promoters may be useful for transgenic expression of the above *Pine* and *Eucalyptus* Pin1 polynucleotide sequences and their variants in forestry species to produce trees that are unable to produce pollen. The engineering of reproductive sterility in plantation trees, for example, is of considerable practical utility in forestry biotechnology, e.g., for preventing the introduction of transgenes into native tree populations, and for general compliance with genetic modification regulatory guidelines.

TABLE 2

The % amino acid sequence identity of plant Pin1 homologs

| Gene code | Species | SEQ ID NO: PROT | GeneBank AC # | No. AA | 1 | 2 | 3 | 4 | 5 | 6 | 7 |
|---|---|---|---|---|---|---|---|---|---|---|---|
| AtPin1 | *Arabidopsis thaliana* | 50 | AAD20122 | 119 | 1 | 79 | 26 | 72 | 76 | 75 | 78 |
| egfb021948 | *Eucalyptus grandis* | 48 | | 127 | 2 | | 34 | 75 | 83 | 81 | 74 |
| prhg006224 | *Pinus radiata* | 49 | | 93 | 3 | | | 37 | 29 | 26 | 29 |
| DlPar13 | *Digitalis lanata* | 54 | AJ133755 | 118 | 4 | | | | 77 | 73 | 72 |
| MdPin1 | *Malus domestica* | 52 | AF290200 | 121 | 5 | | | | | 79 | 72 |
| LePin1-1 | *Lycopersicon esculentum* | 53 | AW621939 | 118 | 6 | | | | | | 71 |
| LePin1-2 | *Lycopersicon esculentum* | 51 | AW945046 | 127 | 7 | | | | | | |

TABLE 3

The % nucleotide sequence identity in the coding region of plant Pin1 homologs

| Gene code | Species | SEQ ID No. DNA | GeneBank AC # | No. bp | 1 | 2 | 3 | 4 | 5 | 6 | 7 |
|---|---|---|---|---|---|---|---|---|---|---|---|
| AtPin1 | Arabidopsis thaliana | 26 | AAD20122 | 360 | 1 | 72 | 11 | 68 | 70 | 74 | 72 |
| egfb021948 | Eucalyptus grandis | 46 | | 384 | 2 | | 24 | 71 | 75 | 75 | 68 |
| prhg006224 | Pinus radiata | 47 | | 282 | 3 | | | 13 | 13 | 14 | 14 |
| DlPar13 | Digitalis lanata | 58 | AJ133755 | 357 | 4 | | | | 74 | 72 | 72 |
| MdPin1 | Malus domestica | 56 | AF290200 | 366 | 5 | | | | | 76 | 71 |
| LePin1-1 | Lycopersicon esculentum | 57 | AW621939 | 357 | 6 | | | | | | 73 |
| LePin1-2 | Lycopersicon esculentum | 55 | AW945046 | 384 | 7 | | | | | | |

It is expected that additional functions of the AtPin1 gene will be revealed by over-expressing the gene in specific plant organs and tissues using tissue-specific promoters. See, e.g., General Methods.

Experiments described in Example 4 below suggest that AtPin1 protein is essential for plant cell survival. When RNAi constructs were used to transform Arabidopsis plants, transgenic plants were not recovered. Thus it would appear that knockout of AtPin1 expression is lethal.

Figure 3:
FIG. 3. *Nicotiana benthamiana* plants transformed with an RNAi silencing construct of AtPin1, JY618, were very small (left) or medium (middle) in size compared to plants transformed with an empty control vector pART29 (right).

Surprisingly, when similar experiments were carried out in Nicotiana benthamiana plants, transgenic plants were produced and showed phenotypes consistent with reduced cell division. That is, the plants were either very small or were of medium size with very small leaves, compared with normal plants (FIG. 3). Since the AtPin1 gene is not 100% homologous to the Pin1 gene in N. benthamiana (NbPin1), the expression of the AtPin1 RNAi construct in transgenic plants may have produced a partial downregulation of NbPin1 expression that allowed plant cell survival. Although the NbPin1 gene is not cloned yet, the homology of NbPin1 and AtPin1 genes is estimated to be in the range of 70-80% on the basis of the sequence homology among Pin1 genes from a number of species including tomato, which is closely related to Nicotiana benthamiana (Table 3).

In another of its aspects, the invention provides methods of producing a plant with a novel growth phenotype by expressing a genomic fragment of a cell cycle regulatory gene sequence, identified herein as SEQ ID NO. 13, in the plant. As discussed previously, the relation between cell division and plant development is complex and not well understood. More often than not, the effects of expressing a known cell cycle regulator on cell division, growth and morphology of specific tissues and organs cannot be predicted in advance of experimentation, yet this knowledge is essential for producing genetically modified plants with new or improved characteristics.

The experiments described below were carried out with a genomic DNA fragment that contains the full ORF encoding the protein for a D-type cyclin of Arabidopsis (AtCycD4;1). The cDNA for this cyclin was isolated by De Veylder et al. who found by in situ hybridization experiments that the gene was expressed during vascular tissue development, embryogenesis and formation of lateral root primordia (De Veylder et al., Planta 208:453-462 (1999) and International Patent Application WO99/22002). These workers suggested that the association of expression with vascular tissue in roots may be correlated with cambial activity. Schnittger et al. used a cDNA fragment and a trichome-specific promoter to overexpress AtCycD3;1 and AtCycD4;1 in endoreduplicating Arabidopsis trichomes and reported that whereas AtCycD3;1 expression unexpectedly produced multicellular trichomes, trichomes expressing AtCycD4;1 were morphologically normal (Schnittger et al., Proc. Natl. Acad. Sci. USA 99: 6410-6415 (2002).

The studies described herein were carried out by transforming Arabidopsis thaliana plants with the genomic DNA fragment identified in the Sequence Listing as SEQ ID NO: 13. The fragment was cloned into pART7 between the 35S promoter and OCS terminator in the sense orientation, and the expression construct was cloned into the binary vector pART27 for transformation of Agrobacterium tumefaciens. Agrobacterium-mediated transformation of Arabidopsis thaliana produced transgenic plants which overexpressed the cyclin D4; 1 molecule. Additional methodological details are provided in Examples 6 and 7 below. As the transgenic plants showed dramatic amplification in cell division, we refer to the gene as AMPLIO1 (AMP1), and to plants transformed with SEQ ID NO: 13 as AMP1 transgenic plants.

Figure 4:
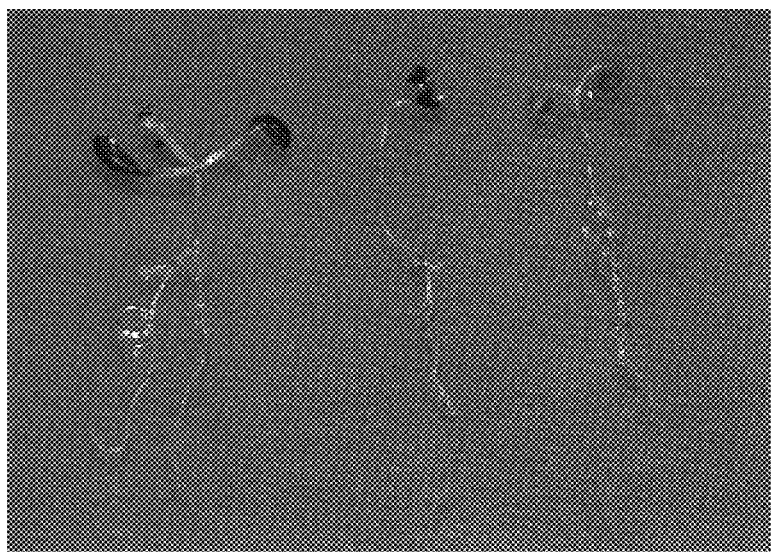
FIG. 4. Phenotypic changes in *Arabidopsis* plants over-expressing AMP1. Hypocotyls of AMP1 T1 transgenic plants are 2-3× longer (middle and right) than plants transformed with an empty vector pART27 (left).
Figure 5:
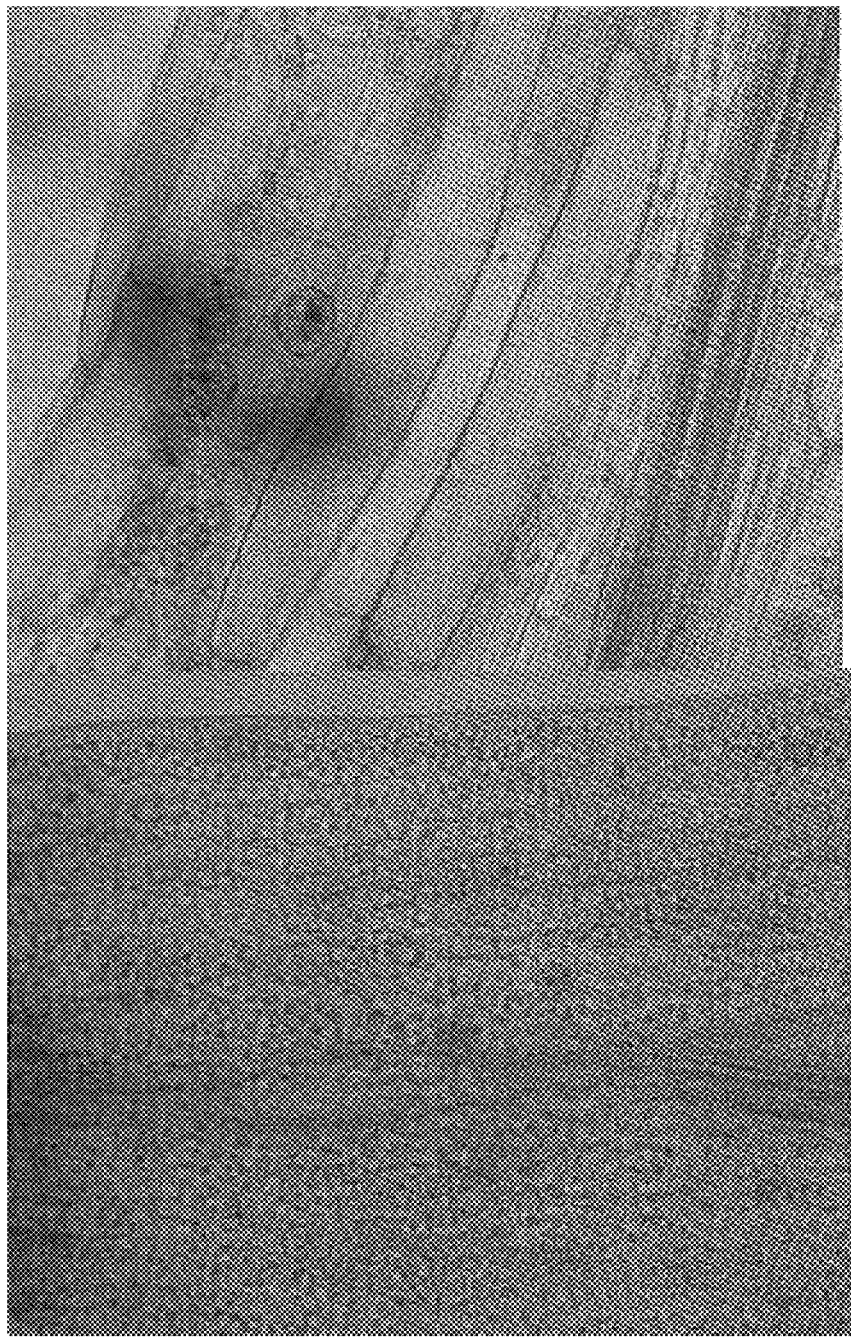
FIG. 5. Phenotypic changes in hypocotyls of *Arabidopsis* plants over-expressing AMP1. AMP1 transgenic hypocotyl (right panel) contains many small cells when compared to the control hypocotyl (left). The cells are smaller in size and the number of cell layers is increased in the AMP 1 hypocotyls.

All AMP1 T1 transgenic plants contained hypocotyls that were at least twice to three times longer than those of control plants that were transformed with an empty vector pART27 containing no gene of interest (FIG. 4). The hypocotyls were whole-mounted onto a microscope slide, stained with toluidine blue, and examined by light microscopy. The results are shown in FIG. 5. It can be seen that the AMP1 transgenic hypocotyl contained many small cells when compared to the control hypocotyl. From the central vascular tissue to the epidermal cell layer, there were 8 cell layers in the control hypocotyls while there were 14 cell layers in the AMP1 hypocotyls. The AMP1 hypocotyl cells were approximately 10% of the length of the control cells. Based on comparative sizes of control and AMP1 cells and the number of radial cell layers, we estimate that the AMP1 hypocotyls contain at least 50 times more cells than the control hypocotyls.

Figure 6:
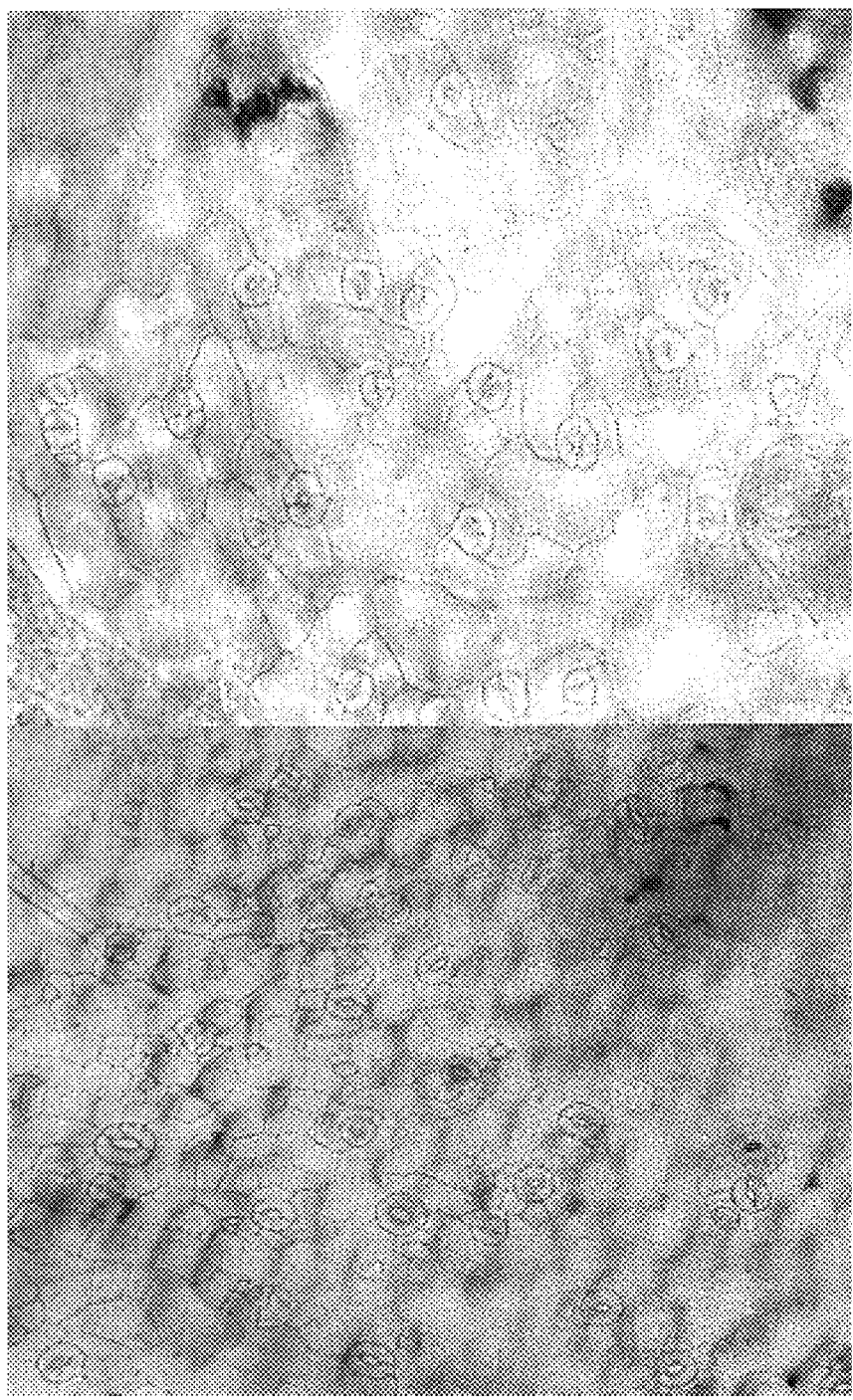
FIG. 6. Phenotypic changes in leaves of *Arabidopsis* plants over-expressing AMP1. Epidermal cell size in leaf of AMP1 transgenic plants (bottom) is much smaller than those in control plant (top).

Cell number and cell size in other organs of AMP1 transgenic plants were also examined and compared with control plant organs. AMP1 transgenic leaves contained more epidermal cells and stomata than the control leaves. Although the stomata size was not changed, the epidermal cell size was much smaller in AMP1 transgenic plants than in the control plants (FIG. 6). Roots from AMP1 transgenic plants and the control plants were stained with 0.1% toluidine blue and 1 µg/l DAPI (4',6-diamidino-2-phenylidole). There were more cells and smaller cells in the root tips and vascular tissues of AMP1 transgenic plants than in the control plants.

Figure 7:
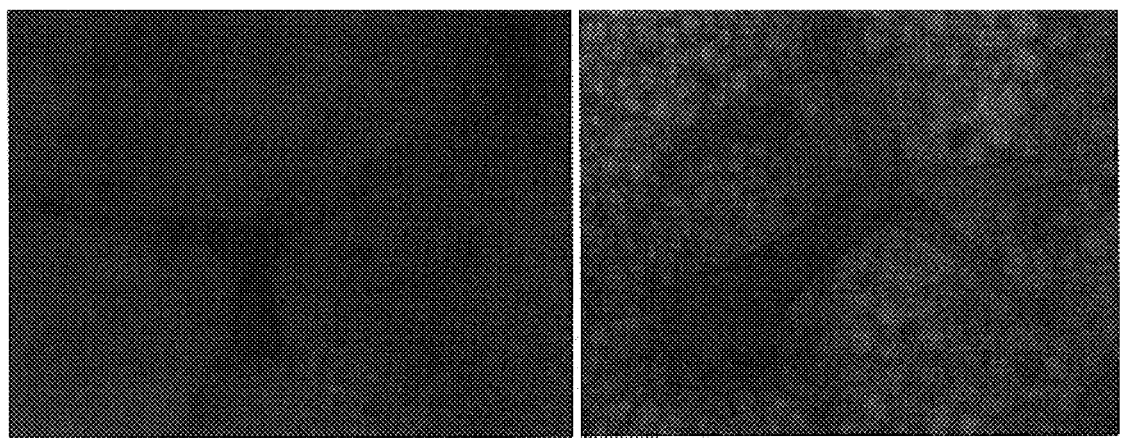
FIG. 7. Trichomes of AMP1 *Arabidopsis* transgenic plants consist of multiple cells and nuclei (left) while trichomes of control plants contain a single cell and nucleus (right).

In contrast to what was reported by Schnittger et al., Proc. Natl. Acad. Sci. USA 99: 6410-6415 (2002), we were surprised to find that trichomes of the AMP1 transgenic plants consisted of multiple (more than 10) cells and nuclei. Trichomes of the control plants were unicellular and each trichome contained only a single nucleus (FIG. 7). It is possible that differences in the sequences (genomic vs cDNA) that were used may account for the differences between our results and those reported by Schnittger et al.

Figure 8:
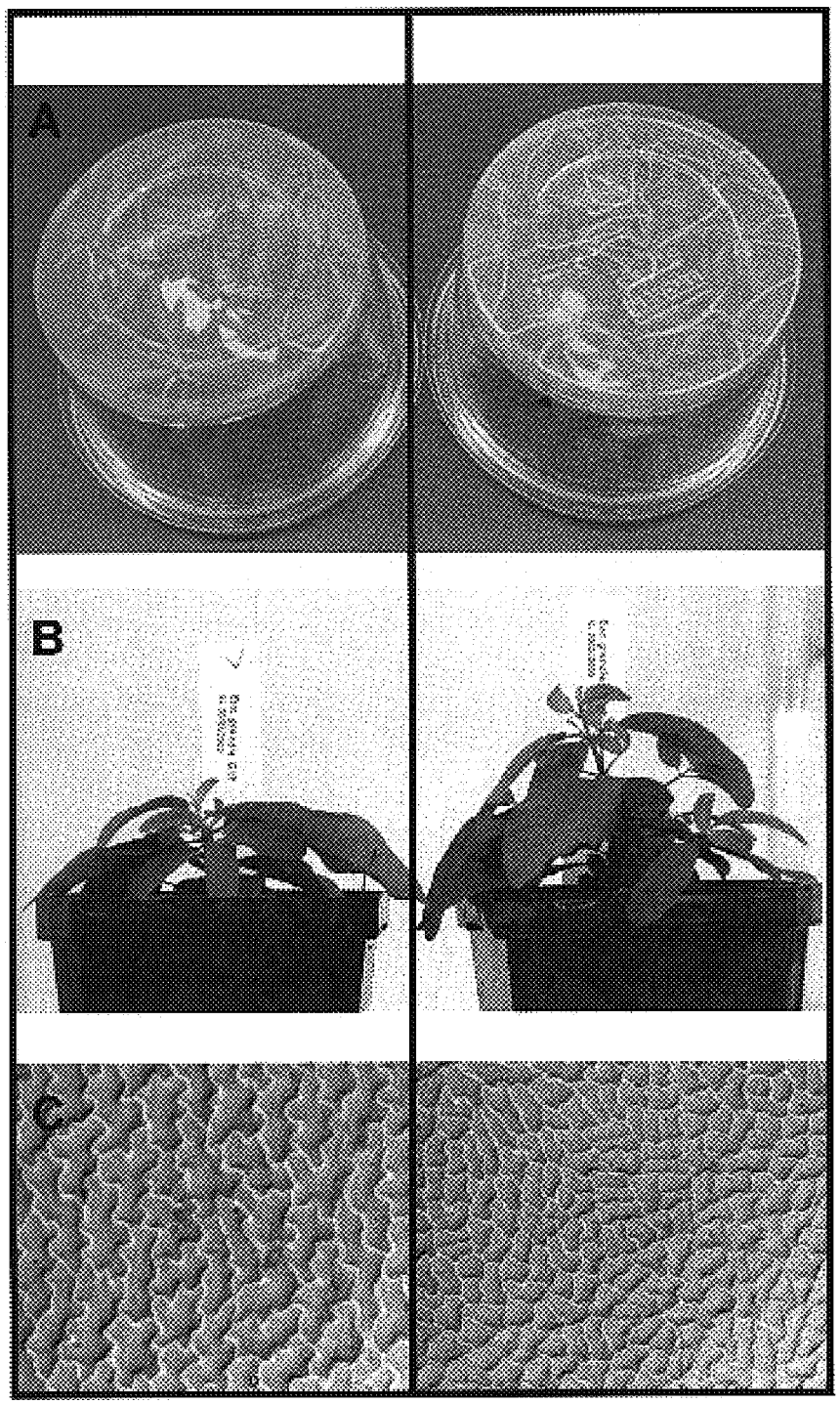
FIG. 8. Phenotypic changes in *Eucalyptus grandis* transgenic plants over-expressing AMP1. The plants transformed with AMP1 construct (on the right) produced longer roots in tissue medium (A), grew faster in soil (B) and contained more and smaller cells (c) than the control plants transformed with the pART69 construct (on the left).
Figure 28:
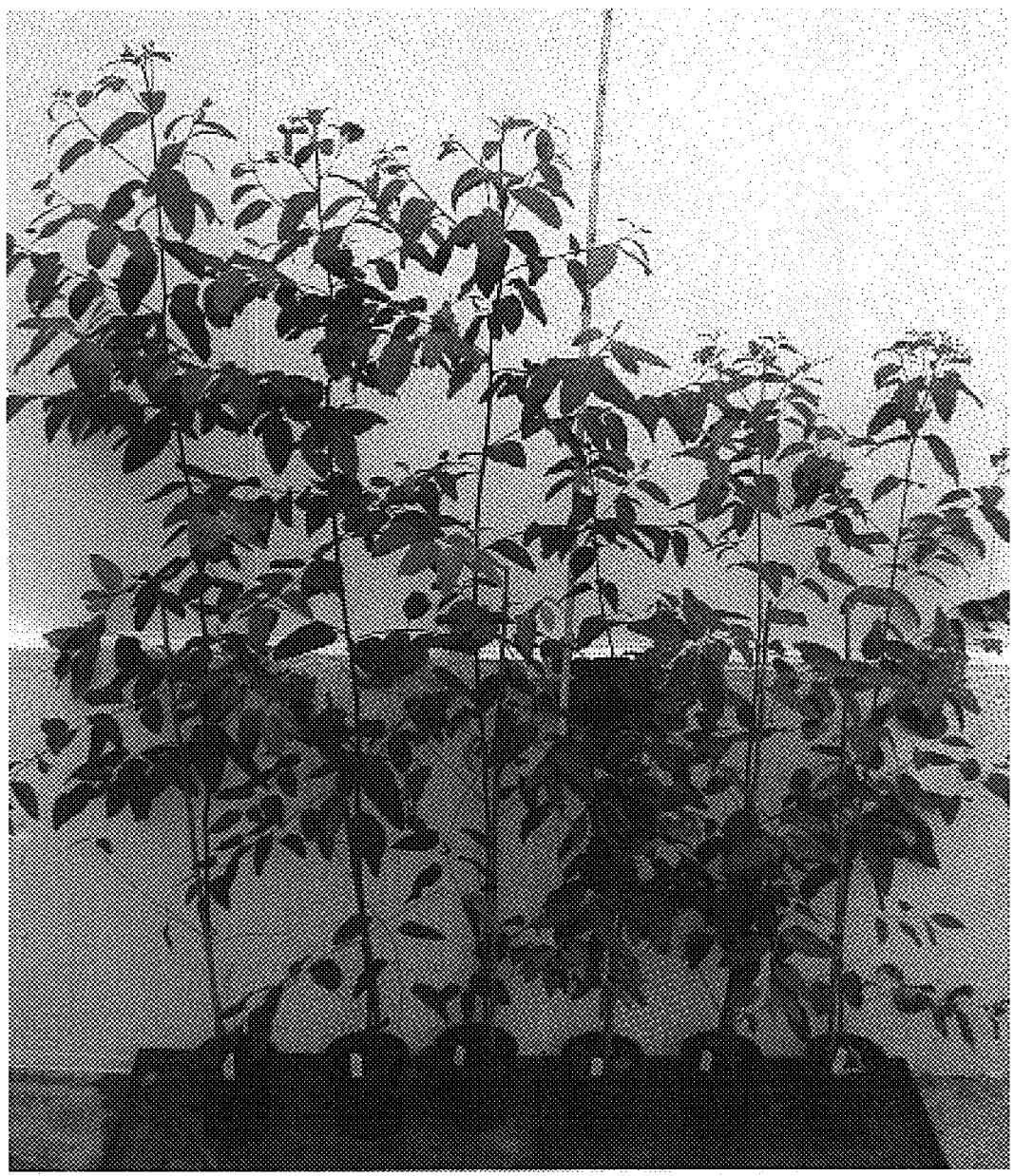
FIG. 28. This figure shows changes in height of three AMP1 *Eucalyptus* plants (left side) compared with three pART 69 control plants (right side) after four months growth in a glasshouse.

The AMP1 over-expression construct was also transferred into *Eucalyptus grandis* plants using an *Agrobacterium*-mediated transformation system developed by Genesis. Twelve independently transformed plants were regenerated. These plants have shown very interesting phenotypes relating to commercial applications. First, they produced root early and produced longer roots than the control plants transformed with the empty construct pART69 (FIG. 8A). Secondly, AMP1 plants grow faster and taller than the control plant in soil (FIG. 8B). Finally, AMP1 plants contain many smaller cells than the control plants in the leaf epidermal cell layer (FIG. 8C). Experiments described in Example 6 and results shown in FIG. 28 indicate that the height and stem diameter of AMP1 Eucalyptus plants are increased by comparison with control plants.

Other experiments carried out with *N. benthamiana* plants showed that when AMP1 or AtCycD2;1 is expressed in the cambium of mature plants, the production of new xylem cells continues and cell number increases in the radial direction. Xylem fiber cells close to the cambium form secondary cell walls. The width of the fiber cell walls remains unchanged with increased cell number, although the diameter of the xylem fiber decreases as the size of the lumen decreases. There is only a small decrease in fiber cell length, circa 15% decrease on average. There are no gross changes in stem and leaf morphology. By comparison, GUS control plants showed no changes in cell number or length (data not shown).

In plants that expressed AMP1 constitutively, increased cell number was accompanied by greatly reduced cell length, and gross changes in plant morphology were observed.

These results suggest that AMP1 and D cyclins related to AMP1, such as those disclosed herein from *Pine, Eucalyptus* and *Cucurbits*, when expressed in wood forming tissues may be useful for increasing biomass, wood density and wood strength in tree and shrub species.

With appropriately selected tissue specific and/or inducible promoters, AMP1 and D cyclins related to AMP 1 may be useful for selectively enhancing cell division in other plant tissues and at specified developmental stages.

In a preferred embodiment of the invention, the sequences identified herein as AMP1 and AMP 1-related D cyclins are selectively expressed in a cell type or tissue that participates in a specified plant developmental process, e.g., wood development or flower development. These sequences may also be used to specifically increase cell number or cell density of vascular and non-vascular tissues in plants such as trees, shrubs, sugarcane, grasses and cereals. By increasing the cell density or number there will be an increase in cell wall yield that is easily converted into pulp and paper, ethanol or another biopolymer for commercial use.

In yet another of its aspects, the invention provides a method for increasing the yield of a product of a biosynthetic pathway that is operative in a plant tissue of interest. The method comprises stably transforming the genome of the plant with one or more of the polynucleotide sequences disclosed herein. Preferably, the expression of the sequence or sequences will be under the control of a promoter that is selectively active in the tissue where the pathway is operative. In one preferred embodiment, the plant is cotransformed with a polynucleotide sequence whose expression results in an amplification of cell number and a sequence that encodes a transcriptional regulator or an enzyme involved in the biosynthetic pathway. Preferably, an increase in the level of expression of the transcriptional regulator or the enzyme will increase the throughput of the pathway to increase the yield of a product of the pathway. In a particularly preferred embodiment, a CycD polynucleotide sequence is expressed in plant xylem in combination with a sequence encoding an enzyme involved in wood development. For example, a cellulose synthase gene, preferably a CesA gene, can be used in this embodiment to increase the amount of highly crystalline cellulose produced by a woody plant (see Example 7 below). Non-limiting examples of enzymes involved in the production of wood components include: cellulose synthase, hexose pyrophosphorylase, sucrose synthase (cellulose production); beta glucosidase, hexose pyrophosphorylase, sucrose phosphate synthase, xyloglucan endotransglycosylase, arabinan synthase, xylan synthase (hemicellulose production); 4-coumarate CoA ligase, cinnamoyl-CoA reductase, coniferin beta-glucosidase, coniferyl alcohol dehydrogenase, mannitol dehydrogenase, coniferyl-alcohol glucosyltransferase, laccase, ferrulate 5-monooxygenase, para-coumarate 3-monooxygenase, trans-cinnamate 4-monooxygenase, caffeate O-methyltransferase, caffeoyl-CoA O-methyltransferase, peroxidase (lignin production); hexose pyrophosphorylase, pectinesterase, polygalacturonase (pectin production); alpha amylase, hexose pyrophosphorylase, starch branching enzyme, starch synthase, phenylalanine ammonia-lyase (starch production); terpenoid synthases, oxidosqualene (terpenoid production); dirigent, expansin, arabinogalactan, extensin, yieldin (cell wall proteins).

The invention also provides plants with novel phenotypes that are produced by use of the methods disclosed herein, including plants showing changes in growth rate, height, stem diameter, length of hypocotyls, length and branching of roots, increased biomass, increased numbers of secondary xylem cells, decreased fiber cell diameter and lumen size, changes in leaves, rosette, bolts, flowering, floral organs, silique, and seed production.

In addition to their uses for plant modification, the above-described polynucleotide sequences and portions thereof, can be used as probes and primers for the detection and quantification of expression of these genes and functionally related variants, and for identifying and isolating genes with similar functions in other plant species. These methods are well-known to those who are skilled in plant biotechnology and can be performed without undue experimentation.

The following Examples are presented to illustrate the practice of the invention, and are not intended to limit the scope of the invention as claimed.

EXAMPLE 1

Isolation and Characterization of cDNA Clones from *Eucalyptus arandis, Pinus radiata, Lolium perenne* and *Cucurbit* Species

*Eucalyptus grandis, Pinus radiata, Lolium perenne* and *cucurbit* cDNA expression libraries from tissues of whole seedlings, leaves at different developmental stages, vegetative buds, flowers, floral buds, roots, fruit at different developmental stages, seed, phloem, cambium, early wood, late wood, mature wood, vegetative stem and juvenile wood, were constructed and screened as follows.

mRNA was extracted from the plant tissue using the protocol of Chang et al. (*Plant Molecular Biology Reporter* 11:113-116, 1993) with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3 HCl) and extracted with chloroform: isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequences for positive clones were obtained using a Perkin Elmer/Applied Biosystems Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+vector.

The determined cDNA sequences were compared to known sequences in the EMBL database of 13 Apr. 2004 using the BLASTN algorithm of version 2.2.1 [Apr. 13, 2001] set to the preferred parameters described above. Multiple alignments of redundant sequences were used to build up reliable consensus sequences. Based on similarity to known sequences from other plant species, the isolated polynucleotides of the present invention were identified as encoding a specified enzyme, as shown in Table 1 above.

Using the procedures described above, sequences identified as SEQ ID NOS: 1-3, 7-10, 12 and 46 were isolated from the *Eucalyptus grandis* library; sequences identified as SEQ ID NOS: 4-6, 11 and 47 were isolated from the *Pinus radiata* library; SEQ ID NOS: 16, 17, 19, 20 and 21 were isolated from the *Cucurbita maxima* library; SEQ ID NO: 18 was isolated from the *Cucumis sativus* library, SEQ ID NO: 22 was isolated from the *Sicyos angulatus* library and SEQ ID NO: 59 was isolated from the *Lolium perenne* library.

FIGS. 9-20 show the positions of domains within the amino acid sequences of SEQ ID NOS: 27-38. These domains were determined with InterProScan software Release v3.1, Nov. 6, 2001. Additional domains were identified based on previous publications as referenced in the Figure descriptions. The InterPro database integrates PROSITE, PRINTS, Pfam, ProDom, SMART and TIGRFAMs databases, and the addition of others is scheduled. InterPro data is distributed in XML format and it is freely available under the InterPro Consortium copyright. The European Bioinformatics Institute (EBI) is a non-profit academic organization that forms part of the European Molecular Biology Laboratory (EMBL): Wellcome Trust Genome Campus, Hinxton, Cambridge, CB10 1SD UK.

EXAMPLE 2

Phenotypic Changes Produced by Overexpression of Genes in *Arabidopsis* Plants cDNA sequences containing complete open reading frames were cloned into genetic constructs for constitutive expression and phenotype analysis in *Arabidopsis* plants. The ORF sequences were cloned between a constitutive promoter (35S or pine super-ubiquitin promoter) and OCS terminator in the sense orientation to achieve over-expression and ectopic expression of the gene. The promoter-ORF-OCS cassette was then cloned into the binary vector pART27. The resulting gene constructs were transferred into *Arabidopsis thaliana* "Columbia" plants using the floral dipping in planta transformation procedures (Clough S J and Bent A., Floral dip: a simplified method for *Agrobacterium*-mediated transformation of *Arabidopsis thaliana*. Plant J. 16: 735-743 (1998)). The GUS reporter gene was cloned into the pART27 plasmid and served as a negative control. This control plasmid is referred to as pART69. T1 seeds were collected after floral dipping and were sown on medium plates containing kanamycin. A minimum of 12 T1 transgenic plants were produced and analyzed for each gene. Typically, 24 T1 plants were produced and analyzed.

A minimum phenotyping system was used to record gross morphology changes. Transgenic plants transformed with a test gene were compared to plants transformed with a control construct (pART27 or pART69) at all development stages. The earliest changes were observed at one week after germination when plants are grown on tissue culture plates, and included changes in hypocotyl length, root length, root branching pattern, root hair morphology and cotyledon size. Then, plants were transferred to rockwool and grown hydroponically in plant growth rooms to maturity. During these stages, growth rate, plant size, and floral traits were monitored weekly and all observed changes were recorded.

As shown in the Table below, the observed phenotypes fall into two groups.

In one group, overexpression of sequences with SEQ ID NOs: 1, 4, 5, 6, 9 and 10 produced large plants, increased root branching and long hypocotyls. These phenotypes may result from increased cell division and/or cell expansion. Sequences such as these are expected to be useful for increasing plant growth rate and biomass.

In a second group, overexpression of sequences with SEQ ID NOs. 2, 3, 7, 8 and 11 produced small plants and short roots. Sequences associated with these changes might encode repressors of cell division and cell expansion. If so, knockout or knockdown of the expression of these genes (e.g., by antisense or RNAi technologies) would be expected to enhance plant growth and biomass production.

TABLE

Summary of phenotype changes observed in plants transformed with over-expression constructs

| SEQ ID NO: DNA | SEQ ID NO PROTEIN | Gene family | Phenotype observed |
| --- | --- | --- | --- |
| 1 | 27 | Auxin transport | Long hypocotyls |
| 2 | 28 | Auxin transport | Small plants, short and less root hairs |
| 3 | 29 | CDC23 | Small plants |
| 4 | 30 | CKS1 | Long roots, more root branches |
| 5 | 31 | CKS1 | Long roots, more root branches |
| 6 | 32 | Kinase | Long hypocotyls |

TABLE-continued

Summary of phenotype changes observed in plants transformed with over-expression constructs

| SEQ ID NO: DNA | SEQ ID NO PROTEIN | Gene family | Phenotype observed |
| --- | --- | --- | --- |
| 7 | 33 | GTPASE | Small plants, short roots |
| 8 | 34 | GTPASE | Small plants, short roots, more root branches |
| 9 | 35 | GTPASE | Large plants, more root branches |
| 10 | 36 | GTPASE | More root branches |
| 11 | 37 | GTPASE | Small plants, short roots |

EXAMPLE 3

Role of AtPin1 in Petal and Stamen Development

The experiments described in this Example suggest that plant Pin1 homologs may be useful in controlling plant floral reproduction. For these experiments, sense and antisense constructs were prepared comprising the *Arabidopsis* AtPin1 gene (At2g18040; SEQ ID NO 23) under the control of the AP3 promoter. Genomic DNA was amplified using the primers given in SEQ ID NOS: 24 and 25, using standard amplification protocols. The amplified fragments were cloned into the binary vector pART69 that contains a nptII gene for kanamycin resistant and a GUS report gene, under the control of constitutive NOS and MAS promoter respectively. The sense construct is referred to as pJY602 and the antisense construct is pJY603. These two binary vectors were transferred into *Arabidopsis thaliana* Columbia plants using Clough and Bent floral dipping transformation protocols.

Figure 2:
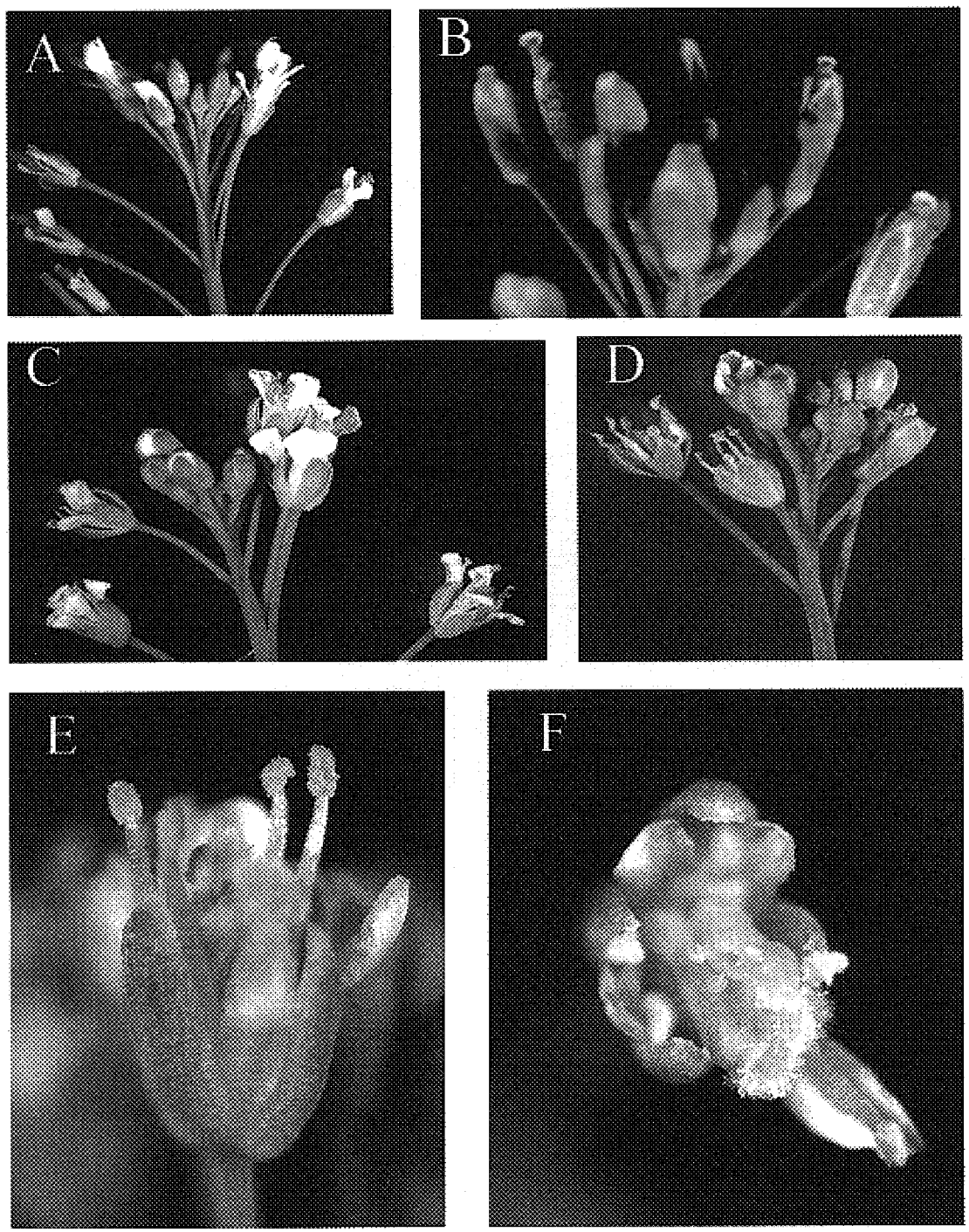
FIG. 2. *Arabidopsis* flower phenotypes. WT flowers show normal development of petals, stamens and carpels (A); Flowers of a pJY603 transgenic plant display no petals or stamens (B); Flowers of plants from cross (pJY603×35S::AP3) showing normal petals and normal stamens (C) or very small petals and normal stamens (D); Higher magnification of flower with small petals (E), and flower with small petals and poorly fused carpels (F).

Thirty-two percent (42/131) of transgenic lines of pJY602 and thirty-nine percent (39/99) of transgenic lines of pJY603 were phenotypically similar to ap3 mutants in that the petals were small and sepal-like, and stamens became carpeloids (FIG. 2, B). These ap3-like plants set seed when pollinated with pollen from WT plants, but set no seed without hand pollination.

The ap3-like phenotype appears to result from altered AtPin1 gene expression, rather than silencing of the endogenous AP3 promoter. If the phenotype were due to promoter silencing, 35S::AP3 should rescue both stamen and petal development.

Experiments were carried out in which multiple T2 plants from several transgenic lines were cross-pollinated with pollen from homozygous plants containing the 35S::AP3 transgene. The resulting *Arabidopsis* hybrid plants were planted in soil. The phenotypes obtained in the crosses are shown in FIG. 2.

The hybrid plants showed close to normal stamen development. That is, the anthers produced pollen grains; the number of stamens per flower was from 5 to 8; sepal development was normal. Carpels were not well fused. Sometimes 3 or 4 carpels were seen per flower. These phenotypes are similar to those of 35S::AP3 transgenic plants.

In most of the plants, however, abnormal petal development persisted. Many of the plants displayed very small petals which were often green, rather than white. White coloration, where present, appeared only on the tips of the small petals. These petals assembled to sepals. A small proportion of plants showed normal petals. It is possible that these plants lacked the AP3::AtPin1 transgene due to segregation, as the maternal plants used in crosses were not homozygous. PCR analysis can be used to verify this interpretation.

The finding that 35S::AP3 can only rescue stamen development in the AP3::AtPin1 transgene background, but not petal development, indicates that the ap3-like phenotype was not caused by promoter silencing, and that altered expression of the AtPin1 gene was most likely responsible. That stamen development, but not petal development, was rescued may relate to the greater strength of the AP3 promoter in petal primordia than in stamen primordia (Hill et al., 1998, *Development* 125:1711-1721). When the AP3 promoter was used to drive a cell division inhibit gene (ICK1) in transgenic *Brassica* plants, only petal development, but not stamen development, was inhibited (Zhou et al., 2002, *Planta* 215:248-257).

The results disclosed here suggest that AtPin1 may interact with AP3, and possibly with other gene products as well, to control petal and stamen development. It is known that the human Pin1 protein interacts with a defined subset of mitosis-specific proteins through binding to the phosphorylated serine or threonine at conserved Ser(Thr)-Pro sites (Lu et al., 1999, *Science* 283:1325-1328). It is also known that there is a conserved Ser(Thr)-Pro site in all AP3 protein sequences examined from 27 different species (Kramer et al., 1998, *Genetics* 149:765-783). This information supports our result that AtPin1 interacts with AP3 to control petal and stamen development. Tree promoter homologs of AP3 appear to function across plant species and should be useful in combination with tree Pin1 genes for modulating floral development in forestry trees.

EXAMPLE 4

Analysis of AtPin1 Function by RNAi Silencing

In our initial studies, AtPin1 was down-regulated in *Arabidopsis* by transforming the plants with an RNAI construct. The design of the construct was similar to that reported by Waterhouse et al. (Waterhouse et al., 1998, *Proc. Natl. Acad. Sci. USA* 95: 13959-13964). The cDNA sequence from AtPin1 (given in SEQ ID NO: 26) was cloned as an inverted repeat under the control of the constitutive 35S promoter and the OCS terminator. The 35S-cDNA-repeat-OCS cassette was then cloned into the pART27 plant transformation vector to result to final construct named as pJY618. The construct pJY618 was transformed into *Arabidopsis thaliana* "Columbia" plants using the floral dipping in planta transformation procedures (Clough S J and Bent A., Floral dip: a simplified method for *Agrobacterium*-mediated transformation of *Arabidopsis thaliana*. Plant J. 16:735-743 (1998)).

However, no transgenic plants were recovered after three repeated transformation experiments, which suggests that the AtPin1 gene is required for plant cell survival and that knockout of endogenous AtPin1 gene expression causes cell death.

We next introduced the RNAi silencing construct pJY618 into *N. benthamiana* plants using *Agrobacterium*-mediated leaf tissue transformation (Burow et al., 1990, *Plant Mol Biol Rep* 8:124-139). Since the AtPin1 is not 100% homologous to the Pin1 gene in *N. benthamiana*, we reasoned that the transcription of the sequence would produce a partial down-regulation of NbPin1 in transgenic *N. benthamiana* plants, thus reducing the problem of plant lethality. Transgenic *N. benthamiana* plants were produced in these experiments. As shown in FIG. 3, the plants showed a phenotype that is consistent with reduced cell division activity. By comparison with plants transformed with the empty control vector pART29 (FIG. 3, right), the plants transformed with the silencing vector were either very small (FIG. 3, left) or were of medium size with small leaves (FIG. 9, middle). These results suggest that plant Pin1 genes that are at least 70% homologous to an endogenous plant gene can be used for gene knockdown to reduce cell growth of shoots and leaves in plants.

EXAMPLE 5

Use of Nucleotide Sequences of Plant Pin1 Genes as Herbicides

The results described in Examples 3 and 4 above clearly demonstrated that AtPin1 gene is essential for plant cell survival. We propose to use sequences of plant Pin1 genes in combination with novel gene silencing technologies for weed control.

It is now well known that small interfering RNA (siRNA) with 21 to 23 nucleotides can trigger silencing of genes containing the same nucleotide sequences in plants and animals (Waterhouse et al., Nature 411:834-842, 2001). The silencing signal can spread systemically over the whole plants. The siRNA can be delivered into plant cells using a range of techniques, such as biolistics (Klahre et al., Proc. Natl. Acad. Sci. USA 99:11981-11986, 2002), Agrobacterium infiltration (Llave et al., Proc. Natl. Acad. Sci. USA 97:13401-13406, 2000) and viral infection (Gossele et al., Plant J. 32:859-866, 2002).

We propose to use the nucleotide sequence of the Pin1 gene of a weed species to generate siRNA. To reduce homology to the sequence of the Pin1 gene in a crop species, the siRNA sequence is preferably directed to non-conserved regions, such as 5' and 3' non-translated regions of the gene. This type of siRNA should only silence the weed Pin1 gene and cause weed death but not affect crop plants. This type of siRNA can be highly species specific and has advantages over herbicides currently available in the market.

Methods for selecting suitable regions in a mRNA target are disclosed in the art (see, for example, Vickers et al., J. Biol. Chem. 278:7108-7118, 2003; Elbashir et al Nature, 411, 494-498, 2001; Elbashir et al, Genes Dev., 15, 188-200, 2001). Preferably, selected target sequences are sensitive to down regulation by low concentrations of siRNA. Guidelines for the design of siNA include those provided in Ambion's Technical Bulletin #506 (available from Ambion Inc., Austin, Tex.)

The siRNA agent may be generated using in vitro transcription techniques and sprayed onto plants. The siRNA sequence may be cloned into a virus that is used to infect weeds and deliver the siRNA. Other means to generate and deliver the siRNA may also be used.

EXAMPLE 6

Production and Analysis of Transgenic-AMP1 Plants

A genomic DNA fragment that contains the full ORF encoding the protein for a AtCycD4;1 (SEQ ID NO: 13) was amplified using the primers given in SEQ ID NOS: 14 and 15, using standard amplification protocols. The amplified fragments were cloned into pART7 between the 35S promoter and OCS terminator in sense orientation to achieve over-expression and ectopic expression of the cyclin. The 35S-ORF-OCS cassette was then cloned into the binary vector pART27. The resulting gene construct (JY17) was transferred into Arabidopsis thaliana "Columbia" plants using the floral dipping in planta transformation procedures (Clough S J and Bent A., Floral dip: a simplified method for Agrobacterium-mediated transformation of Arabidopsis thaliana. Plant J. 16:735-743 (1998)). For an additional negative control, the GUS reporter gene was cloned into the pART27 plasmid. This control plasmid was called pART69. T1 seeds were collected after floral dipping and sown on medium plates containing kanamycin. More than 30 kanamycin resistant, T1 transgenic plants were identified from the first sow of 1 ml of T1 seed. The same construct was also transferred into N. benthamiana using the method as described by Burow et al., (Plant Mol. Biol. Rep. 8:124-139, 1990) and Eucalyptus grandis plants using an Agrobacterium-mediated plant transformation system developed by us and disclosed in U.S. Provisional Patent Application No. 60/508,944, filed Oct. 6, 2003. Twenty N. benthamiana and twelve E. grandis transgenic plants were regenerated from independently transformed cells and established in soil for growth rate and wood quality analysis.

All AMP1 T1 transgenic Arabidopsis plants showed longer hypocotyls, e.g., 2 to 3 times longer, than control plants that were transformed with an empty vector pART27 containing no gene of interest (FIG. 4). Examination under a microscope showed that AMP1 transgenic hypocotyls contain many small cells when compared to the control. From the central vascular tissue to the epidermal cell layer, there are 8 cell layers in the control hypocotyls while there are 14 cell layers in the AMP1 hypocotyls. The AMP1 hypocotyl cells are approximately 10% the length of the control cells (FIG. 5). AMP1 hypocotyls contain at least 50 times more cells than the control hypocotyls. The AMP1 transgenic hypocotyls are longer and have more cell layers in the radial direction, but have much smaller and shorter cells than the control hypocotyls.

Cell number and cell size in other organs were also examined. AMP1 transgenic leaves contained more epidermal cells and stomata than the control leaves. Although the stomata size was not changed, the epidermal cell size was much smaller in AMP1 transgenic plants than in the control plants (FIG. 6). Trichomes of the AMP1 transgenic plants consisted of multiple (more 10) cells and nuclei. Trichomes of the control plants had only a single cell and nuclei (FIG. 7). Roots from AMP1 transgenic plants and the control plants were stained with 01% toluidine blue and 1 µg/l DAPI. There were more cells and smaller cells in the root tips and vascular tissues of AMP1 transgenic plants than in the control plants.

The results show that AMP1 can enhance cell division in hypocotyls, leaves, trichomes and roots when it is expressed in transgenic plants under the control of the constitutive 35S promoter. Together with tissue specific and/or inducible promoters, AMP1 may be used to enhance cell division in many types of plant tissue and at different developmental stages.

Transgenic plants of N. benthamiana and E. grandis over-expressing AMP1 were also found to contain much more cells and smaller cells than control plants. After 4 months growth in a glasshouse, the height of Eucalyptus grandis plants transformed with the AMP1 overexpression construct was increased by about 20% compared to pART69 control plants. Ten plants of each of three AMP1 independent transgenic lines and two control lines grown in the same glasshouse unit were analyzed. These results indicate that AMP1 functions across species barriers and can potentially be used to manipulate cell number and cell size in a wide range of plant species.

These results suggest that trees and shrubs can be modified by overexpression of AMP1 and AMP1-related cyclins to increase the yield of cell wall materials, such as cellulose, and biomass to make them more suitable for biofuel uses. Additionally, these modified trees are expected to have improved wood qualities for construction purposes (e.g., increased wood density and strength).

EXAMPLE 7

Increasing the Level of a Product of a Biosynthetic Pathway in a Plant Tissue of Interest To improve wood development in tree species, AMP1 is cloned into binary vector under the control of several tissue specific promoters driving gene expression in cambium and developing xylem cells. These constructs are introduced into tree species using *Agrobacterium*-mediated transformation systems. Cell number and cell size in the cambium and developing xylem region in transgenic plants are compared to control plants. Tree height and trunk diameter are compared between AMP1 transgenic plants and control plants. It is expected that the AMP 1 transgenic trees will produce more wood and more cell wall material (eg. cellulose) than the control plants.

To further improve cellulose production, a cellulose synthase gene (CesA) is cloned into a binary vector under the control of a tissue specific promoter driving gene expression in developing xylem cells. This construct is co-transferred together with the 1S AMP1 gene construct described above into tree species (including *Eucalyptus* and willow) using *Agrobacterium*-mediated transformation systems. The presence and expression of both genes in a transgenic plant is analysed using PCR and RT-PCR techniques. Over-expression of AMP1 in cambium cells should increase the number of cells for xylem (wood) differentiation and over-expression of CesA in differentiating xylem cells should improve cellulose production in the secondary cell walls. The transgenic plants over-expressing both genes are expected to produce an extra amount of cellulose because the AMP1 increases the number of xylem cells and the CesA gene increases cellulose content in each xylem cell.

In like manner, AMP1 can be used in conjunction with other enzymatic and regulatory genes of a biosynthesis pathway to increase the levels of plant biochemicals.

General Methods

Genetic Transformation

The gene constructs of the present invention comprise one or more polynucleotide sequences for use in transforming bacterial and plant host organisms. Methods for constructing and using vectors are well known in the art and are described generally in Berger and Kimmel, *Guide to Molecular Cloning Techniques*, Meth. Enzymology, vol. 152, Academic Press, Inc., San Diego, Calif.; Sambrook et al., (1989) *Molecular Cloning-A Laboratory Manual* ($2^{nd}$ Ed), vol 1-3, Cold Spring Harbor Laboratory, NY; Current Protocols in Molecular Biology, (F. M. Ausubel et al., eds.) Current Protocols, Greene Publishing Association and John Wiley & Sons, Inc.

Methods for transforming plants and portions thereof with polynucleotides are described in Draper, J. et al., (1988) *Plant Genetic Transformation and Gene Expression. A Laboratory Manual.* Blackwell Sci. Pub. Oxford, p. 365; Potrykus, I. and Spangenburg, G. (1995) *Gene Transfer to Plants.* Springer-Verlag, Berlin.; and Gelvin S. B. et al., (1993) *Plant Molecular Biol. Manual.* Kluwer Acad. Pub. Dordrecht. An excellent review of transgenic plants, including transformation techniques, is provided in Galun E. and Breiman, A. (1997) *Transgenic Plants.* Imperial College Press, London. Plant vectors for expressing foreign genes in transgenic plants typically include promoters for driving the expression of one or more cloned ORFS, terminators and selectable genes. Examples of constitutive plant promoters include the CaMV 35S promoter, the nopaline synthase promoter and the octopine synthase promoter, the pine Superubiquitin promoter (see U.S. Pat. No. 6,380,459, which is incorporated by reference herein in its entirety) and the Ubi 1 promoter from maize. Specific plant promoters which are active in specific tissues, respond to internal developmental signals or external abiotic or biotic stresses are described in the scientific literature. Exemplary promoters and fusion promoters are described, e.g., in WO 02/00894, which is herein incorporated by reference. Promoters of genes that are preferentially active in procambium tissues, such as, for example, AtHB8 (Kang and Dengler, *Planta* 216: 212-219, 2002) and AtHB15 (Ohashi-Ito and Fukuda, *Plant Cell Physiol.* 44: 1350-1358, 2003) are useful for specific enhancement of wood development.

Terminators are found in the 3' untranslated ends of genes downstream of the translated sequence. Terminators are important determinants of mRNA stability and in some cases have been found to have spatial regulatory functions. Examples of terminators that are commonly used in constructs include the PI-II terminator region of potato, the octopine synthase 3' terminator and the nopaline synthase 3' terminator.

Overexpression of transgenes can be used to produce gain of function phenotypes, expression of dominant negative mutations can produce loss of function phenotypes, and sense and antisense suppression of gene expression and RNAi can be used to produce transgenic lines with loss-of-function or reduced function phenotypes. RNAi reduces or eliminates specific gene functions by targeting for degradation the transcription products of genes with dsRNA homologous to the introduced sequence (reviewed by Sharp, P., (1999) *Genes & Development* 13: 139-41). RNAi can be produced by introducing double-stranded or single stranded RNA into plant cells, or by transforming the plants with RNAi expression constructs. Representative examples of RNAi silencing methods can be found in the following patent applications: WO98/36083; WO99/15682; WO/98/53083; WO99/49029; WO99/53050; WO01/77350; WO01/94603;WO02/00894; WO01/75164; and WO01/68836.

Analysis of Related Sequences

Sequences that are homologous to those described in this application can be identified by computer-based methods, using public domain sequence alignment algorithms and sequence similarity search tools to search sequence databases (public domain databases include Genbank, EMBL, Swiss-Prot, PIR and others). See, e.g., Nucleic Acids Research, 29, 1-10 and 11-16 (2001) for online resources. Similarity searches retrieve and align sequences for comparison with a target sequence to be analyzed (i.e., a query sequence). The optimal alignment between local regions of the compared sequences is known as a local alignment. Sequence comparison algorithms use scoring matrices to assign an overall score to each of the alignments.

Polynucleotide and polypeptide sequences may be aligned, and percentage of identical residues in a specified region may be determined against other polynucleotide and polypeptide sequences, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN algorithm Version 2.0.11 [Jan. 20, 2000], set to the default parameters described in the documentation and distributed with the algorithm, are preferred for use in the determination of polynucleotide variants according to the present invention. The BLASTP algorithm, is preferred for use in the determination of polypeptide variants according to the present invention. The use of the BLAST family of algorithms, including BLASTN, BLASTP, and BLASTX, is described in the publication of Altschul, et al., "Gapped BLAST and PSI-BLAST: a new generation of protein database search programs," *Nucleic Acids Res.* 25: 3389-3402, 1997. The BLASTN software is available on the NCBI anonymous FTP server (ftp://ncbi.nlm.nih.gov) under /blast/executables/ and is available from the National Center for Biotechnology Information (NCBI), National Library of Medicine, Building 38A, Room 8N805, Bethesda, Md. 20894 USA.

The FASTA software package is available from the University of Virginia (University of Virginia, PO Box 9025, Charlottesville, Va. 22906-9025). Version 2.0u4, February 1996, set to the default parameters described in the documentation and distributed with the algorithm, may be used in the determination of variants according to the present invention. The use of the FASTA algorithm is described in Pearson and Lipman, "Improved Tools for Biological Sequence Analysis," *Proc. Natl. Acad. Sci. USA* 85: 2444-2448, 1988; and Pearson, "Rapid and Sensitive Sequence Comparison with FASTP and FASTA," *Methods in Enzymol.* 183: 63-98, 1990.

The following running parameters are preferred for determination of alignments and similarities using BLASTN that contribute to the E values and percentage identity for polynucleotide sequences: Unix running command: blastall -p blastn -d embldb -e 10 -G0 -E0 -F -r 1 -v 30 -b 30 -i queryseq -o results; the parameters are: -p Program Name [String]; -d Database [String]; -e Expectation value (E) [Real]; -F filter query sequence; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; and -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0 -E 0 -F -v 30 -b 30 -i queryseq -o results; the parameters are: -p Program Name [String]; -d Database [String]; -e Expectation value (E) [Real]; -F filter query sequence; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

Multiple sequence alignments of a group of related sequences can be carried out with PILEUP, which uses progressive, pairwise alignments. (Feng et al., *J. Mol. Evol.* 25: 351, 1987).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, *Nucleic Acids Res.* 22:3583-3589, 1994; Hofmann et al., *Nucleic Acids Res.* 27:215-219, 1999) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., *Nucleic Acids Res.* 30(1):235-238, 2002). Prosearch is a tool that can search SWISS-PROT and Tremble databases with a given sequence pattern or signature.

Proteins can be classified according to their sequence relatedness to other proteins in the same genome (paralogs) or a different genome (orthologs). Ortholog genes are genes that evolved by speciation from a common ancestral gene. These genes normally retain the same function as they evolve. Paralog genes are genes that are duplicated within a genome. These genes may acquire new specificities or modified functions which may be related to the original one. Phylogenetic analysis methods are reviewed in Tatusov et al., *Science* 278:631-637 (1997).

All of the references, publications and patents cited in this application are incorporated by reference in their entirety for all purposes as long as they are not inconsistent with the present disclosure. It should be understood that the invention is not limited to the embodiments and examples above, and that various modifications can be made without changing the scope of the invention.

SEQ ID NOS: 1-60 are set out in the attached Sequence Listing. The codes for nucleotide sequences used in the attached Sequence Listing, including the symbol "n," conform to WIPO Standard ST.25 (1998), Appendix 2, Table 1.

We claim:

1. A method for modulating plant growth and biomass, comprising stably incorporating into the genome of the plant a recombinant genetic construct comprising in the 5' to 3' direction: (a) a gene promoter sequence; (b) a polynucleotide sequence having SEQ ID NO: 13; and (c) a gene termination sequence.

2. The method of claim 1, wherein the plant is a tree or shrub.

3. The method of claim 2, wherein said recombinant genetic construct comprises a promoter that is selectively active in wood-forming tissues.

4. A method for producing a plant having improved wood properties, comprising: (a) transforming a plant cell with a recombinant genetic construct comprising: a promoter that is active in wood-forming tissues; a polynucleotide sequence having SEQ ID NO: 13; and a gene termination sequence; and (b) cultivating the transgenic cell under conditions conducive to regeneration and mature plant growth, wherein said plant exhibits one or more of the following changes compared with an unmodified plant: increased stem diameter, increased xylem fiber cell number, reduced fiber diameter and lumen size, increased yield of cell wall material, altered cell wall composition, increased wood density and increased wood strength.

* * * * *

SEQUENCE LISTING

```
<160> NUMBER OF SEQ ID NOS: 60

<210> SEQ ID NO 1
<211> LENGTH: 2571
<212> TYPE: DNA
<213> ORGANISM: Eucalyptus grandis

<400> SEQUENCE: 1
ctctcatggt tctctccttg cttcgtcttc ttcaccaaaa tccaaacttt ccccacagaa        60
actccacttc gcagcaagcg aaaactctgc actgcacata gtacgcagta cagttcaatc       120
cctcgtcgct tctccgcctg cttgacgacc gccgccgccg ccgccatgat caagtggcac       180
gatctctacg cggtgctggt cgcggtggtg ccgctctacg tggcgatgat cctggcctac       240
ggctccgtgc ggtggtggag gatcttctcc cccgaccagt gctccggcat caaccgcttc       300
gtcgccatct tcgccgtccc gctcctctcg ttccacttca tctccaccaa cgaccccta        360 cgcatgaacc tccgcttcat cgccgccgac accctccaga agctcctcct cctcctcctc       420
ctcgccctct gggccaacct ccaccgccgc ggctccctgg actggtccat caccgtcttc       480
tccctctcca ccctccccaa caccctcgtc atgggcatcc ctctcctcgg cgccatgtac       540
ggcaccgaag ctagcaacct catggtccag gtggtcgtgc tgcagtgcat catctggtac       600
accctcctcc tcttcctctt cgagtaccgg ggcgcgaaga tcctcatcat ggagcagttc       660
cccgagaccg ccgcgtccat cgtgtccttc aatgtcgacc cggacgtcgt ctccctcgac       720
ggccggaact tcctcgagac cgacgcggag gtcggccaag acgggaagct gcacgtcacg       780
gtgaggaagt cgaacgcgtc gcggcggtcc ttcggcctgg ggcctggcgg tggcggctcg       840
ttctccggga tgacgccgcg gccttcgaac ctcagcggcg tggagatcta cagcctgagc       900
tcgtcgcgga acctgactcc gagggggttcc aactcggact tctactccat catgggcgtg       960
cctcggctct ccaacttcgg accctccgac gcgtactccg tccagtcctc ccggggcccg      1020
accccgaggc catcgaactt cgacgagaac ctgcagccgt ccccgaagtt cgggttctac      1080
ccggcccagg tcgcgtccgc cccgtacccg gctccgatcc ccgatttcgc atcagcattc      1140
gcgaagagcg gcaaacccaa ccagcaacag cagcagccgg cgccggcgcc gccggagcag      1200
caatctaacg gcgcggcaaa ggcaaacagt tacgacgcca aggagctcca catgttcgtg      1260
tggagctcca gcgcctcgcc ggtttcggaa gtcggcgggc tccacgtttt cggcagcggc      1320
gatttcgggg ctccggacaa tcaatccagg cgggccgatc acagcgtcaa ggagatccgg      1380
atgatggttg ccgataataa ccagcccaac ggcgagacca aaactgcccc ggaaacgacg      1440
ggatttactg gcaagatca gttcaacttc gtggctaaag cagacgaaag ggacgagggg      1500
accggaggag agaaggaggc ggccgggccc gaccggccca acaagctctg cgcgagctcc      1560
tccgccggag agcggggggg gtacggcggc ggcgacgacg ccgggaacga caagcagatg      1620
ccgccggcga gcgtgatgac ccgcctcatc ttgatcatgg tgtggaggaa gctgatccgg      1680
aaccccaaca cctactcgag cctcatcggc atcatctggt ccttgatcgc cttccggtgg      1740
gatgtgggaa tgcccgagat cgtcgacaag tccatccaca tactgtccga cgccgggctg      1800
ggaatggcca tgttcagctt gggtctgttc atggctcttc agcctaagct aattgcgtgc      1860
```

```
gggaactctg tcgccacgtt cgccatggcc gtcaggttcc tcgttggccc agctgcgatg    1920
gccatcgcct ccgccgctat cggattgcgc gggcccctac tccatatagc catcgtccag    1980
gcggcgcttc cccagggaat cgtcccgttc gtgtttgcca aggagtacaa cgttcatccg    2040
gccgttctca gcaccatggt catattcggg atgctgatag ccctgccaat cacgcttgtc    2100
tattacattc ttctaggact ataaaaagga ttcctcctaa atatattccc acccccctat    2160
acacgagtcg caaaggaagt gaatccgaag cataatccaa tccgacaatg gcgaaattga    2220
cgacaaatgg gagaggcgat tcggggaagc actcgtgagg atttcctggg attcttacac    2280
ggggaagaac gaagcgacaa ggggtgtaaa acgttaggcg aatcccccc ctggaaaata    2340 gggttcatgt ctccataaga ggccaattag agctggtctg aattggtttt ttattatttt    2400
tcttttgcaa gtgttgatta ttgagtaaga aagaatatat atatatagag agagaacacc    2460
tagctatgta gctagtctca atgttttcaa tggggacatg agggggtggg aaggaggttc    2520
tacataagat ataccttcca ttatattatt cctagattcc taaaaaaaaa a            2571
```

<210> SEQ ID NO 2
<211> LENGTH: 2121
<212> TYPE: DNA
<213> ORGANISM: Eucalyptus grandis

<400> SEQUENCE: 2

```
ctgaaacgcg tgccatttaa gcccctcctc ctcctcctca agttcaccat ccaaacgtct     60
ccctcttctt gatcaacccc gcgaggcacg atgatcacgg ggtcggactt ctaccatgtc    120
atgacggcga tggtgccgct gtacgtggcg atgatcctgg cctacggctc cgtccggtgg    180
tggcgcatct tcaccccgga ccagtgctcc ggcatcaacc gcttcgtcgc cctcttcgcg    240
gtccccctcc tctccttcca cttcatctcc tccaacaacc cttcaccat gaacctccgc    300 ttcctcgccg ccgactccct ccagaagctc ctcatcctcc tcgccctcgc cctctggtcc    360
cacctctccc gccgcggctc cctcgactgg tccatcaccc tcttctccct ctcaaccctc    420
ccaaacaccc tcgtcatggg catccccctc ctccgcggca tgtacggccc ctactccggt    480
gacctcatgg tccagatcgt cgtcctccag tgcatcatct ggtacactct tatgctcttc    540
ctgttcgagt tccgcgccgc ccgaaccctc atctccaacc agttccctgg cactgctgcc    600
gcgtccatca tctccatccg agttgatcct gacgtcgtct ccgcttgtac ggatccgcgg    660
cagtcccttg agaccgaggc tgaggtaggc agtgatggca agctccgtgt caccgtccgc    720
cgctccagcg cctcgcggtc agacatcttc aagcccgcgg catggctctc tccacggccg    780
tcaaacctga ccaatgctga gatctactca ctacagtcgt cgcggaaccc aacgccaaga    840
gggtccagct tcaaccatgc cgaactctac tccgttgctg cggggctcgg aggcggtggg    900
aggggatcaa acttcgggtc tgctgacgtg tacggcctat cagcaccgtt cgggccaacg    960
ccgaggccat caaattacga agaggataaa ccgaagttcc catatggcag cggaggcagc   1020
acggccggta gctaccccgc cccaaatcca gggatgttct caccaaagaa caacggtggg   1080
agcggaggga agagggcgaa tgtccaagga gggaagagag gagctgaaga tggtggtggt   1140
ggtggtcgga gggatcttca catgtttgtt tggagctcaa gtacttctcc agtttctgat   1200
gtgtttggga acaaccatga cttgcccacc ggtgcaactc atgagaaagt ggatcagaat   1260
catattaaag aaggtgatca gctggagaga gatgagttca gcttcaggaa cagaaggccg   1320
gagaatgtcg aagcgggtgg cggggatgcg atgccaccaa cgagtgtgat gacaaggctc   1380
```

-continued

```
atcttgatca tggtgtggag gaagctcatc cggaaccgta acacctactc cagcttgatc    1440
ggcatcactt ggtccctcgt ctccttcagg tggcacatcg agatgccgc aatcatagcc    1500 aagtccattt ccatactgtc agatgcagga cttggcatgg ccatgttcag ccttggtctg    1560
ttcatggcgt tgcaacccaa gatcatagct tgcgggaatt ccgtcgcaac ttttgctatg    1620
gccgtcagat tcctcaccgg tccggccgtc atggccgctg cctccctggt aatcggcctc    1680
aggggtgatc tcctccgcgt cgccatcgta caggcagctc ttcctcaggg gatcgtcccc    1740
ttcgtcttcg ccaaagaata cggcctacac ccggacattc ttagcacagc tgtcatattc    1800
gggatgttaa tcgccttgcc aattacactc gtctactaca ttttctgggg catctgaaga    1860
gcgaagaaaa accctagaat ctccgagaga tgatgaagaa tttggcttct taatttgatc    1920
gccagtccac aggatcctgc agagaccatg agaacaaat catagtgcaa atcaagcttt    1980
cttctccaat ggtattttta ggaaaattgt aaaatcatgg ttgtagttaa tagaaattat    2040
ctaccctgtt cttttgagct ataaagagaa atctaggagg agggaatgtt atcccactcc    2100
aaggtcaaag caaaaaaaaa a                                              2121

<210> SEQ ID NO 3
<211> LENGTH: 2174
<212> TYPE: DNA
<213> ORGANISM: Eucalyptus grandis

<400> SEQUENCE: 3
ccgacgacga cggagaaaga cagctgcttt tcctcctcgc cgccgacgac cgccgccgcc      60
gctccgtaga agcttcggca ccgcaagaac cgggacctca actgctttcc cacactgaat     120
gcggtcgcgc aggtcgtaga ttccgcgact cgagagagct tcgatgggtt cgaaggaaat     180
ctgccggaac gagctccgga ttgcagtccg ccagctcagc gatcgctgcc tctactctgc     240
ttccaaatgg gcagcggaac aactagtggg aatcgagcta gacccggtaa agttcacacc     300
ttcaaacacc agattccagc gtgggagctc cagtatccgc aggagattcc gcaccaatga     360
gatcatgtcg acgccaattg ctggggtgtc gtatgtgagt actccggtca tggaggaaga     420
tgacatagtt gatggtgact tttatcttct ggccaagtct tactttgact gccgtgagta     480
tcggagggct gctcatgtgc ttcgggatca gtatgggaag aaagctgtct tcctacgatg     540
ttatgctctt tatctggctg agaaaaccg gaaagacgaa gagaatatag aacttgaagg     600
gcccttaggt aagagtgatg ctgttaacaa ggaattggtt tctctggaga gggagttgtc     660
aatgctacgt aagaatgggt ccattgatcc ctttgggttg tacttgtatg gtcttgttct     720
taaagagaaa ggcagtgaac accttgcacg taaccttctt gtggaatctg tgaatagcta     780
tccttggaac tggagtgcat ggtcagagtt acaatccttg tgcactacaa tcgacatatt     840
acatagtcta cctctcaata atcattggat gaaggatttc tttcttgctg gtgcatatca     900
agaactcaga atgcacaacg agtccttagc aaaatatgag tatctgcaag gcaccttcag     960
cttcagtaat tacatacagg cacaaattgc aaaagcgcag tacagtctaa gggaatttga    1020
acaagtagaa gtgatatttg aagaactcct gagaaatgat ccttaccgag tggaggacat    1080
ggatatgtat tccaatgtac tctatgctaa ggaatgcttt tctgccttga gttatcttgc    1140
ccacagggta ttcatgactg ataagtacag gccagaatct tgttgtataa ttggaaatta    1200
ttatagcttg aaaggccaac atgagaagtc agttatgtat tttaggaggg cccttaaatt    1260
gaataagaat tgtttatctg cttggactct tatgggtcat gaatatgttg agatgaaaaa    1320
cactccagca gctgttgatg cctatcggcg agctgtagat ataaatccat gtgattaccg    1380
```

-continued

```
agcctggtat ggtttaggac aggcctatga gatgatgggg atgccttttct acgctcttca    1440 ttatttcaga aaatctgtat tcttgcagcc aagtgattct cgcttatgga ttgctatggc    1500
tcagtgttat gaaactgaac agcttcacat gctagaagag tcaatcaagt gttacaggag    1560
ggcagcgaat tgtaatgaca gggaagcaat tgctcttcac aagctagcaa agttgcattg    1620
tgaacttggg cgtttagaag aagctgcttt ttactacaaa aaggatctgg agcggatgga    1680
agctgaagag agggacggac ctaatatggt tgaagctttg cttttcttg ccacacacgg    1740 caaagaccaa aagagatttg aggaggcgga ggtgtattgc acacgtcttc ttgattatac    1800
tggcccggag aaagagactg caaagagtct actacgagga atgagaatgg cacaatctgg    1860
ttttccttca atgagtgctg agcatttttcc tccataacat tactgataaa tggagctgtg    1920
aaattttcga agcaggtgtg gcattgtgtt gaggatataa aaaaaatacg tgatctcctc    1980
ccaaaagatg acaaatcctt aaggctgcgc cagctgcttg ctgtaactct ctctgccaat    2040
tgactgcata cttttggaat agagaaagtg gccattggtt tcttaggtat atgagagatt    2100
ggtcaatttt tgacagtttg tgtcataatg tttcatttat gagaaaccat ctagaaaact    2160
ggagatttca tagt                                                      2174
```

<210> SEQ ID NO 4
<211> LENGTH: 820
<212> TYPE: DNA
<213> ORGANISM: Pinus radiata

<400> SEQUENCE: 4

```
cagcgtttta tctgatacac gaaggatttt taaatttgta agtgctcagt ttttgcaggc    60
ctgtaaaatg gatcaaatag agtattctga gaaatactac gacgtacct atgagtacag    120 gcatgttgag cttccgcctg atgttgcccg gctacttccc aagaatcgcc ttctaaccga    180
gaatgaatgg cgaggaatcg gggttcagca gtctcgtggg tgggtgcact atgctattca    240
ctgctctgaa ccacacatta tgttattcag aaggcctttg aattacgagc aaaaccacca    300
gcaccctgag ccacacatta tgttattcag aaggccgttg aactgccagc caaaccacca    360
gccacaagca catcatccaa cataggctgt ggggattcga gcctgatggt tatgcactgt    420
ggccagcaag atgttgaagt tttagctgag taatttgaaa gttcctttt tccttttcac    480 catagctatt atttgtgtac gtatttccca ggctatgtac agatttaaat tgaaatctag    540
ccatgactat gggccttgag atatgactat tgtatatgta tccctatct tgtgaattgt    600 gaaatttata tgttttttc ttctgcgaat ggttcaaaat tagacgaaca gaaattttgt    660
tcccagtaca gtaaagccca aatgcaagag ggcggacgca ggcgttgtgg gttacatcat    720
gtcatgtaat ttgtctgatc aagttctaag gctggcttgg tatcaatgaa cttttaactt    780
ctaattttga agacatacat ttattctttt aaaaaaaaaa                         820
```

<210> SEQ ID NO 5
<211> LENGTH: 751
<212> TYPE: DNA
<213> ORGANISM: Pinus radiata

<400> SEQUENCE: 5

```
ttcgcccaat ctcaggttct cgctcactaa ttttcgtttc aaagggtttt atcagagctt    60
tccaccgctg tttgcagggc atttcaagtt ctcagggcgg aattcgacct gtctgttatc    120
cgccagatca ttcaagcctt tagttcgctc gactaggatg cctcaaattc agtactcaga    180
```

-continued

| | |
|---|---|
| gaaatacact gatgatacct atgaatacag acatgtggtt ctccctccgg aaactgccaa | 240 |
| attgcttccc aagaaccgac ttctcaatga gaatgaatgg cgagccattg gagttcagca | 300 |
| gtctcgtgga tgggtgcact atgccattca tcgtcctgag ccacacatca tgttattcag | 360 |
| aagacctttg aattaccagc aaaaccagca gcaacaggct ggggctcaat ctcaacctat | 420 |
| gggtttgaaa gcccagtgag ttttattgtg ggttgttgaa agcagtttca atgttctgtt | 480 |
| tgaaactaat cagaataggt tctccagggt gtttgacttt tcctttgca ggtagttctg | 540 |
| cagttttagt atattagggt gatgactttc tttatcaagg ctagtctgtt gtttagttaa | 600 |
| tacggttgac aatgaatgtc tagtacatat ttttgtgaac tattatgaac tattgcttct | 660 |
| aaactgtaga agcctgttat ctttagactc gtggttatgt gaactacttt tacagtaaat | 720 |
| tgcacataac tgttaactgc taaaaaaaaa a | 751 |

<210> SEQ ID NO 6
<211> LENGTH: 3700
<212> TYPE: DNA
<213> ORGANISM: Pinus radiata

<400> SEQUENCE: 6

| | |
|---|---|
| ctcagatggg ctgcgtctgt gccaaacaat ccgacattct cggtgaacca gaatctccca | 60 |
| aggtcaaggg ttcgaatctc gcctccagca ggtggtcggt ctcctccgaa acaaaacaac | 120 |
| tgccgcaaca ttctgattct ggaatcctgc atcatcagca ttattaccac cctcgagacg | 180 |
| aatccgacga agccaaattg aaagagagca actatggtgg atcgaagagg agaacaaggc | 240 |
| agggaaggga tcccgctgac ttggatatgg gcatcttcgt ccgcactcct tccagccaat | 300 |
| cagaggccga gctggtggca gctggatggc cggcctggat ggcagctttt gcaggggagg | 360 |
| ccatccatgg ctggatccct cgcagggcgg agtccttcga gaaactgtac aagattggac | 420 |
| aagggactta cagtaatgtg tataaagctc gtgatcttga taatggaaaa attgttgccc | 480 |
| tgaagaaggt acgttttgac agtttggatg ctgaaagtgt gcgatttatg gcacgagaaa | 540 |
| tactggttt acgcaaactt gatcatccaa atattgtcaa attggaagga cttgttactt | 600 |
| cagaggtatc ctctagtctg taccttgtat ttgagtacat ggagcatgac cttgctggac | 660 |
| ttgctgcttg cccggggatc aagttcactg aaccacaggt taaatgttat atgcaacaat | 720 |
| tacttcaagg acttgatcac tgtcacagac atggtgtact ccatcgtgat atcaagggtt | 780 |
| caaacctttt aattgacaat ggaggcattt taaagatagc tgactttggt ctagcaactt | 840 |
| tcttttatcc tgatcagaaa cagctcctga caagtcgtgt tgtaacactt tggtaccggc | 900 |
| ctccagaact tttgcttggt gctacagatt atggagttgc tgtggatata tggagtgctg | 960 |
| gttgcatact tgctgaactg cttgctggca agcctatctt gcccggaaga acagaggtgg | 1020 |
| aacaactgca caaatatttt aaattgtgtg gatcaccatc tgaggactat tggaaggagt | 1080 |
| caaaattacc acatgcaacc atattcaagc cacaacaccc ttacaaaagt tgcattgctg | 1140 |
| aggctttcaa agatttctct ccatcagctt tggccttgtt agaaactctc cttgctatag | 1200 |
| aacctggtca tcgtgagaa gcaagtgggg cccttaagag tgaattcttt acaacggagc | 1260 |
| cgctttcttg tgatccatca agcttaccta ataccccgcc aagcaaagag tttgatgcaa | 1320 |
| aattgcgtgc tcaagaaaca agaaggcaaa gagatgtggg tgtgagaggt catggatctg | 1380 |
| aggcagcaag gagaacgtcc cgactatcta gagcaggtcc aacaccaaat gaaggtgctg | 1440 |
| aattaacagc attaactcag aagcagcatt cgacttctca tgcaacttca acattggaa | 1500 |
| gtgaaaaacc aagcactaag aaggaagatt acactgctgg attgcatatc gatcctccaa | 1560 |

```
ggcctgtcaa tcattcttat gaaacaactg gtgtttcacg tgcatatgat gcaattcgtg    1620
gggttgctta ttctggccca ttgtcacaga cacatgtaag tggttcaaca tcaggaaaga    1680
agccaaaaag agatcatgta aagggacttt caggtcaatc atctttgcaa ccatcaaaac    1740
cttttatagt ttctgactca agatcagaga gaatctatga aaaagccat gtaactgatt     1800 tgtcaaatca ttcaagacta gcagtaggaa gaaaccgtga tactacagac ccacacaaaa    1860
gtttgagtac tctgatgcaa caaatccagg atggtacatt agatggaata gatattggca    1920
cacatgaata tgcaagggct ccagtttctt caacaaagca aaaatcagct caattgcaaa    1980
gaccgtcaac attgaaatat gtagataatg ttcaacttca gaatacacgt gtaggaagtc    2040
gccaaagtga tgaaagacct gccaataaag aatctgatat ggtatctcat cgtcaggggc    2100
agagaattca ctgctcggga cctctgctgc acccatctgc caacattgaa gaccttttac    2160
aaaagcatga gcaacaaatc caacaggctg tacgcagagc acaccatggt aaacgtgaag    2220
ctctaagtaa caaatcatct ctccctggaa agaaaccagt ggaccataga gcttgggttt    2280
cttctggaaa aggaaacaaa gaatcaccat attttaaagg aaaagggaac aaagaattgt    2340
cagatcttaa agggggacca actgccaaag taacaaactt taggcagaag gtaatgtaaa    2400
gtatagctaa ggaaattgca gatgaaggga ttcagaaaga gaaccctcc agtcaggcac     2460 aaaaagatat gaacaaagaa aaatacttgc tacatgtctt ctaggtcata ttctggtctc    2520
tctagttgct gacgtcaatt tatgaatgga ttggttgatt tgggatggga gttttttatt    2580
ttctaagcac tgggttgct tcagcgggca aatcaataat cacgtaccttt ataaaatagg    2640 gtatcctcaa ttttttttc tttatttata actgcgaggg tttatgggat cttttaactc     2700
tgcagaaaac ttatacaggg agtttcaaac catcaggtaa gtcttttgca tttaagatta    2760
ttgatcacct tctaaagaag tcacaattgt cttgcaactg cccgttaaaa cgttgaagga    2820
ctatttggtt ttatctcgag atctctgtga tgcaacaact gactatatgg tcactcttaa    2880
gttgcagcga atgcgaatgg ctctagccac attgtaatga tctgtttcag tattttctgt    2940
acagtggaag aataaagtta tgccaaagtt ctttcaagaa cttccattag acttttgtat    3000
ttgttcatac atgattcgat agaataagaa atcatgcata agagactttc ttttaaggga    3060
aacatctatg cctggaagat tgagatgaag ggttctattt taatagatat gggattggtt    3120
gcaaatgtaa ggagccaggt tcttccattg gcctggagga ttttgtatgg gacccttaca    3180
tgctgctgat gaagacctat cacttggcta tgcttggcat taaaacgaac tgaaaagaga    3240
ggcggcactg aggagtcaag ccacatctga gaaaagactt taaattcagc atgcactcat    3300
tgtgaagatt gttattatgg gtgagtccta aatggttatg aacgctgtat ttgtctgcaa    3360
ggatagcgtt cttgacaagg gccaaatctt tccatgtttg gtttacagaa gtttgtatt     3420 taattttgtt cattgcattc tgttgcagtg tttcaattga atccgtgtca gaggaagcag    3480
cacaatatgt aggttttgtg gagttaatct tttagtttta ggaagcaaag ttttctacat    3540
ttcagagtag ggcttttccct ctacagtttt gagtgtagtg tgtttctttt atatcttgca   3600
atcaaagaaa tcatagctac tgattccatg ctatccatgg tatctacttc acgataataa    3660
aggtcttagt ccacaagttt gatgtggtat aaaaaaaaaa                          3700
```

<210> SEQ ID NO 7
<211> LENGTH: 1002
<212> TYPE: DNA
<213> ORGANISM: Eucalyptus grandis

<400> SEQUENCE: 7

```
aaggaagcaa ggaagaagaa gaagcgaaag gaaaacagct ccgttggttg ggaacgttcg      60
cccctcctcc tcctcctctc aatttcctcc gccgtcaacg cctccccctt ccgcctccgc     120
ctctccctcc gatcgccgcc gatcgccgcc cgccgatctc cgatcccgac cgatggccac     180
ctccggcaac aagaacatca atgccaaact ggtgcttctt ggagatgttg gagctggaaa     240
atctagctta gtactgcggt ttgttaaagg ccagttcgtt gaatttcagg aatccaccat     300
tggcgctgcc ttcttttctc agactttggc tgtaaatgat gcaactgtga agtttgagat     360
ctgggataca gctggccaag agagatacca cagcttggct cccatgtact atagaggagc     420
tgcggcagca atcattgtgt atgacatgac aaacctagca tcatttgagc gagccaaaaa     480
gtgggttcaa gaacttcagg cacagggtaa ccctaacatg ttatggctc tcgccggaaa      540
taaagcagat ttgttggatg cccggaaggt tacagctgag gaagcacaaa catatgccca     600
agaacacggt ctcttcttta tggaaacatc tgcaaaaact gctgcaaacg tcaatgacat     660
tttctatgaa atagctaaaa gactacccag agctcagcca gcaccgaacc cgtcgggaat     720
ggttctcatg gacagacctg ccgagaggac ggcagctgca tcgtgttgtt cttaaagtag     780
cctttgtctg tgctttctgt aaaagcccat gacgccttct cccccaaaaa gcatgatgaa     840
ttttcgtcac tcagatgttg tctctgccga aatatcgcgg aattgtacat gctatgttaa     900
tttaggcccc tcttatgcac agtgttatca agggcgtgtg atatataatc tttcatatat     960
aaatgtaatg actatggttt ggctcctata ttaaaaaaaa aa                       1002
```

<210> SEQ ID NO 8
<211> LENGTH: 986
<212> TYPE: DNA
<213> ORGANISM: Eucalyptus grandis

<400> SEQUENCE: 8

```
caaactcagc cccttccgcg cccagtcagc tctttcgcca gtctcagcac cctcggccgc      60
ctacccatca gccccagcct tcaacccctag accaccaaac ttccgcgtgc caaatatgtc    120
tgagatccgt cgcaagttgg tcatcgtcgg tgacggagcc tgcggaaaga cttgcctctt    180
gattgtattc tcaaagggta ccttccctga ggtctacgtc cccactgtgt ttgagaacta    240
cgttgcggac gtcgtcgtcg acgggaagcg ggtcgagctt gccctgtggg acactgccgg    300
gcaggaggac tacgaccggc tgcggccgtt gtcgtacccc gactcgcacg tgatcctgat    360
ctgcttcgct gtcgactcgc ccgactgcct cgacaacgtg caggagaagt ggatctcgga    420
ggtgctccac ttctgctcag gcctgcccat catcctcgtc ggctgcaaga aggacctccg    480
ccacgaccca aagaccgtcg acgagctcag gcgcacctcg cagcgcccgg tcaccagcca    540
ggagggcgac tcggtcaggc agaagatcgg cgcgacccgg tacctcgagt gctcggccaa    600
gacgggcgag ggcgtcaggg aggttttcga gcaggcaacc aggctcgcgc tcctctctca    660
gaagggtgga aagggtggga agaagggaaa gtgcaccgtc ctctaagcgg cacactctgc    720
ccttcttgac tctggctgtt cctggtgaac ccctcttgac cccccggcgg tggaggtggc    780
gtcagtcggg ctcgccgccc cagcctgact gctcgtccct cgccgtcctc gtttctcctc    840
ttcttttgtg gtacactgca ttcccccact ttcccacctt ttttaccccc ctcactagtt    900
tagctcgttg gctcctcggt ttctgacgtc tctcctcaat ttgacccccc cctgaaatga    960
cccctcgtgt ctccccaaaa aaaaaa                                         986
```

<210> SEQ ID NO 9
<211> LENGTH: 958
<212> TYPE: DNA
<213> ORGANISM: Eucalyptus grandis

<400> SEQUENCE: 9

```
gttcccacca tctctctctc tctctctctc tctctctcta attcgatcga ttcaggcccc      60
cccaccccg gcgctcctcc tcctcctccg cctccctgcg ccacctccgg ccggcggcga     120
cgtcgtctcc agacatgtcg tacgactacc tcttcaagta catcatcatc ggcgacaccg     180
gtgtgggcaa atcgtgcctg cttctgcaat tcacggacaa gaggttccag cccgtccatg     240
atctcaccat cggcgtcgag ttcggcgctc gcatggtcac catcgacggc aggccgatca     300
agcttcagat ttgggacacg gcaggacagg aatctttcag atccatcact agatcttact     360
atagaggagc agctggagca cttctagttt atgacatcac ccggagagat acttttaatc     420
atcttgcaag ctggttggag gatgctcggc agcatgcaaa tcccaacatg acaatcatgc     480
ttataggaaa caaatctgat ctatctcatc ggagggctgt caccaaagaa gaaggagaac     540
agtttgcaaa ggaaaatgga cttctatttt tggaggcatc tgcgagaaca gcacaaaatg     600
ttgaggaggc ttttgtaaag actgcggcac agatcctaca gaatatacaa gacggcgtgt     660
ttgatgtatc taatgagacg tcaggaatca aggtgggata tgggcgcct caaggtcaag      720
ccggtgcaag agatggagct gtagctcaga ggggtggctg ttgcagctga atgaggatag     780
cgcagcattg gcattggtgt tcttctacga tctgttcttc tccaatctgt taattctgat     840
cttggccctg aaattttcta tatgttctga tgctgcttta gataaatgtg aaatgtacag     900
atctgttcac acctgttcct cgatagctat catttgtaga cccagtcgac gcggccgc       958
```

<210> SEQ ID NO 10
<211> LENGTH: 869
<212> TYPE: DNA
<213> ORGANISM: Eucalyptus grandis

<400> SEQUENCE: 10

```
tttttataga ctacttccat taacgagaat ccttcctcca tcggcgtctc cttctccttg      60
tgcttcttgt tcttggtgag actcttggaa aagggatggt ggattcgttc gacgaagagt     120
gcgattactt gttcaaggcc gtcttgaccg gggactctgc cgtcgggaaa tcgaatctcc     180
tatcgaggtt cgcgaggaag gagttccagt tggattcgaa acccacgata ggcgtcgaat     240
tcgcatacag gaacgtcaag gtcgccgaca agctcatcaa agcccaaata tgggacactg     300
cagggcaaga aagatttcga gccatcacca gttcatacta tcgcggagca ctggggggcgc     360
tgctggttta cgacatcact cggcgagtga cgttcgagaa cgtgaagaaa tggctgcgcg     420
agctcagaga ctttgggaat cccgacatgg tggtggtcct ggtcgggaat aagtccgatc     480
tgagcaactc tagagaagtg gacctggaag aagggaagga ctttgcggag cagagaatc     540
tgtgcttcat ggaaacttct gctctggaga atctaaatgt cgaggaagca ttcttggaga     600
tgatcaccag aatccatgag atcacaagcc agaagagctt agaagccaag aacaatgaaa     660
taaccagtag ccttcacggt cctaagcagg tcattcagat tgatgaggtc actgctacta     720
aaaagtcata ctgttgctca atttaatccc aaccgttggg ggatttttg acgagtcagt     780
accaaattta tagttgccta ctgaccacat cttgattttt tttcccctga attcaagtcc     840
aatcagcttc ctctttgcga aaaaaaaaa                                       869
```

<210> SEQ ID NO 11

<211> LENGTH: 859
<212> TYPE: DNA
<213> ORGANISM: Pinus radiata

<400> SEQUENCE: 11

| | | | | | |
|---|---|---|---|---|---|
| cccctccctc | ccttccctct | ccacttctac | gtctctgaga | cacatatatc | cctcttctac | 60
| atatacgaat | cccaaccagt | ttacgagcga | gattatcatg | tctggacctg | gtgcgattcg | 120
| tcgaaaactc | gtgattgtcg | gtgatggcgc | gtgcggcaaa | acaagtctgc | tatgcgtatt | 180
| cgcgatgggc | gagttcccaa | agaatacga | accaactatt | ttcgaaaact | acgtagcaga | 240
| aattagacta | gacggcaaac | ctgtccaact | cgcgctctgg | gatacagctg | gtcaagaaga | 300
| atacgaacgt | cttcgaccgc | tatcctactc | caaagcacac | gttattctca | tcgcgtttgc | 360
| aatcgatacg | cccgactcgc | tggagaacgt | ttctgtcaag | tggatcgaag | aggttcgaaa | 420
| tatctgcggt | ccacaaaccc | ctgtgattct | cgtcggttgt | aaagccgatt | gcgacctgc | 480
| ttcggggagc | agtgcggatg | gacgacagta | tgtgacgcgt | caacgggcgc | aggctgttgc | 540
| tcaggagatt | ggcgcacgcg | cgtataaaga | atgttcagca | ctcaacaacc | agggcgtaga | 600
| cgacgtattc | gaggcagcca | cacgcgcgag | tatgatcgtg | cgcgaggtta | aacccgaggc | 660
| ggacgaggaa | caccgtgggg | ggtgttgtgt | gctttgttaa | actcctctcc | gctcgccgct | 720
| ttgggatccg | tatgttgtgt | atagtgcatc | tttcttcttt | tttcgttgat | ctttgtgtgt | 780
| gtgctttatt | ctcctttttt | ttcttttcta | tcatcagatt | gctatgatca | tgacatggtt | 840
| catccaccca | aaaaaaaaa | | | | | 859

<210> SEQ ID NO 12
<211> LENGTH: 1577
<212> TYPE: DNA
<213> ORGANISM: Eucalyptus grandis

<400> SEQUENCE: 12

| | | | | | |
|---|---|---|---|---|---|
| cacaatgacc | tgagggaggt | ctcgacagac | cacttcttct | ccgccaaaga | agaagatggc | 60
| gatggtacag | cgacaaggtc | acgacccatc | atcgccgcag | gagcaagaag | acggtccttc | 120
| ctccttcttg | tccgacgatg | ctctctactg | tgaagaaggc | agattcgaag | aagacgacgg | 180
| cggcggcggc | ggccaagttg | acggaattcc | actcttcccc | tcacagccgg | cggatcgaca | 240
| gcaagactcg | ccgtgggcag | acgaagacgg | cgaggagaag | gaggaggagg | aggcggagct | 300
| gcagtcgctc | ttctccaagg | agcgcggagc | gaggccggag | ctcgcgaaag | acgacgggg | 360
| cgccgtcgcg | gcgcggcggg | aggccgtgga | gtggatgctg | atggtgaggg | gcgtctacgg | 420
| gttctcggcg | ctcacggcgg | tgctggccgt | cgattacctc | gaccggttcc | tcgccgggtt | 480
| ccgcctgcag | cgggacaaca | ggccgtggat | gacgcagctg | gtggccgtcg | cgtgcctcgc | 540
| cctggccgcc | aaggtggagg | agaccgacgt | ccctctcctc | gtagaactcc | aagaggtcgg | 600
| ggacgcgagg | tacgtgttcg | aggcgaagac | ggtgcagcgg | atggagctcc | tggtgctgtc | 660
| gacgctcggg | tgggagatgc | acccggtgac | gccgctgtcg | ttcgtccacc | acgtcgccag | 720
| gaggctcggc | gcgagccccc | accatgggga | gttcacccac | tgggcgttcc | tccgccgctg | 780
| cgagcggctc | ctcgtcgccg | ccgtctccga | tgcgagatcg | ctgaagcatc | tcccgtcggt | 840
| cctggccgcg | gcggcgatgc | tgcgcgtcat | cgaggaggtc | gagccgtttc | gttcctcgga | 900
| gtacaaggcc | cagctcttga | gtgccctcca | catgagccag | gaaatggtgg | aagactgttg | 960
| cagattcatt | ctgggaatag | cagagaccgc | gggcgatgcc | gtgacctcgt | ccctcgacag | 1020
| cttcctgaag | cgcaagcgtc | gctgtggtca | ccttagcccg | aggagcccga | gcggggtcat | 1080

-continued

| | |
|---|---|
| cgacgcctcg ttcagctgcg acgacgagtc gaacgactcg tgggccaccg acccgccatc | 1140 |
| cgatccggac gacaacgacg atctgaaccc tctaccgaag aagagcaggt cgtcgtcgcc | 1200 |
| gtcctcctcc ccctcctcgg tgccagacaa ggtgttggac ttgcccttca tgaacaggat | 1260 |
| cttttgagggc atcgtcaacg gcagtcctat ctgatcgtcc ccctctctct ctctctctct | 1320 |
| ctctctctct ctctctctag aatttgtatc gacccttttc aattaaatca agtgaagaa | 1380 |
| aatgtgaagt gaaagatgag agctttgcgt tgaagaaacg ggaagggtct gcgcttacgt | 1440 |
| atgcatgtct ttttttggcg ctccctctcg gtctcttcaa tgatcttgaa gtgtcccttt | 1500 |
| cacttcagaa tttgcttcat gtatgggaca tggacaggag atatatatat tatgtcacca | 1560 |
| ttacaataaa aaaaaaa | 1577 |

<210> SEQ ID NO 13
<211> LENGTH: 2295
<212> TYPE: DNA
<213> ORGANISM: Arabidopsis thaliana

<400> SEQUENCE: 13

| | |
|---|---|
| acaatctaac gatacagttc cttttagatc gattaccaaa tacaaaggat caattttct | 60 |
| tacatgaaca ctctgttgta atggcagagg agaatctaga actgagtctt ttatgtacag | 120 |
| agagcaacgt tgatgatgag ggcatgattg ttgacgaaac tccgattgaa atttcgattc | 180 |
| ctcagatggg ttttttctcaa tcggagagtg aggagattat catggagatg gtggagaagg | 240 |
| agaagcagca tttgccaagt gatgattaca tcaagagact tagaagtgga gatttggatt | 300 |
| tgaatgttgg aagaagagat gccctcaatt ggatttggaa ggtctgattc tctatttgat | 360 |
| tttgatttct ggttttgaaa tttggatgtt gattggtttt gaatgatctg tataagctca | 420 |
| aattgtgaaa agcacaatcc ttttgatgaa tgatctgaac ataaagagtg tgttgctatg | 480 |
| tctattagat cagaggctta tgcagaacag atagagaggt tttgtcttaa atctgtaaat | 540 |
| ctgatgctca atttccgatc tttcacactt caattgacaa tagattcact tcagtctcag | 600 |
| agttttagat ctctaattga tcttttcttc tgttctgatt acaacaggct tgtgaagtac | 660 |
| accagtttgg accattgtgt ttttgcttag caatgaacta cttggatcga ttcttatcgg | 720 |
| ttcatgattt gcctgtaagt tcacattggt taaactaaaa gattgataat gttttagcc | 780 |
| attcatcatc aaaaagtctc atttttttcgc ttcttgattt gtgattcttc ttgtagagtg | 840 |
| gcaaaggttg gatattgcag ttgttggctg tggcttgttt atcattggca gccaaaattg | 900 |
| aagaaactga agttccaatg ttgatagatc ttcaggttct cctctaaact cgttaaattg | 960 |
| tcgagatgtt ctattcgacc cgacaatgtc ttgaatcgat tgcggtttga tcacatttcg | 1020 |
| gaacaggttg gagatcctca gtttgtgttt gaggctaaat cagtccaaag aatggagctt | 1080 |
| ttggtgttga acaaattgaa atggagattg agagcaataa ctccatgctc atacataaga | 1140 |
| tatttcctga gaaagatgag taaatgtgat caagaaccat ccaacacatt gatatctaga | 1200 |
| tcattacaag tgatagccag cacaaccaaa ggtgaaaaaa aaagtctttc ctttatgttt | 1260 |
| tatttttcttg accactttg ttttttgtgct ttttttgggtt ttgttgtttt tttcactttt | 1320 |
| gcttttatg attttggatt aaaatggtgg ttgtgtcgag tgagcaggta ttgacttttt | 1380 |
| ggagtttaga ccttctgaag ttgctgctgc tgtggcactt tctgtttctg gagaattgca | 1440 |
| gagagtacac tttgacaact cttccttctc tcctctttc tcactacttc aaaaggtaaa | 1500 |
| aaacaatcca ccaaacatct caaactcata aatctattgt ttttaatac caaacacaca | 1560 |

```
cacacatata aagcagcctt tggtggttca atttcaagga aatgccagtt gtggagaagt   1620
ttgaactcat taaagatgac acatttatgt gtatatatgt gtgtgcacta acttattcat   1680
tgcatacaca taatatgtgt aattataaat ccaaaaagta aaaaaaaaaa aaaaaaaaa    1740 aagagaaacc ggttaatggg tctgaatcct ttgacttcca aaactagtgg agagtagacc   1800
aaagaccact ttaaattata ttattctcta gctatgtgtc ttgtgactct ctctgtcaca   1860
cacacacatt cactgcacag cctctagtca catctaaaac caatctgccc ccacaaaaac   1920
atgtttgatt ctgatttgat cttgcaatcc aaaacatcag cctggtttcc attagttgtt   1980
tttctacacc agaaaaagct gaagagatct ttgtgtgttg tgtttgtgtt tgtgttcaag   2040
agacaaaaac aaaagtgtca agctttaaac tttgtggttc cttttattgc aggagagagt   2100
gaagaagata ggggaaatga tagagagtga tggctcagac ttatgttcac aaacacccaa   2160
tggggtttta gaagtatcgg cttgttgttt cagctttaag acccatgatt cttcttcttc   2220
ttatacacat ctttcttaaa aaaaaaactg ttttttttctt acattattat aatcagtatg   2280
atgtctgatg agagg                                                   2295

<210> SEQ ID NO 14
<211> LENGTH: 25
<212> TYPE: DNA
<213> ORGANISM: Artificial Sequence
<220> FEATURE:
<223> OTHER INFORMATION: Made in the lab

<400> SEQUENCE: 14
atgacaatct aacgatacag ttcct                                          25

<210> SEQ ID NO 15
<211> LENGTH: 25
<212> TYPE: DNA
<213> ORGANISM: Artificial Sequence
<220> FEATURE:
<223> OTHER INFORMATION: Made in the lab

<400> SEQUENCE: 15
aatcagtatg atgtctgatg agagg                                          25

<210> SEQ ID NO 16
<211> LENGTH: 1981
<212> TYPE: DNA
<213> ORGANISM: Cucurbita maxima

<400> SEQUENCE: 16
cttcaaccaa actactttt cttcactta aaccggcgtt agagattccg tccagttctc     60
cgatctcttc tccagcgact tttgaacctc tctcgtttgg aagatggcaa tagaatgagg   120
agccagaagt ggcgatcatg tccgtatcga tttccaactg cttctctgat ttgctctgcc   180
aggaggattc ctccggtgtc ttgtccggtg aatcgctggg atgttcttcc gacctcgact   240
ccccggcctg cgtcgaggaa tctatcgccg tcttcatcaa ggacgagcgt cacttcgtcc   300
ccgattacga ctgtttgtcg cgcttccaat tccgtcgct ggatgcggcc gctagattag   360
actctgttgc atggattctt aaggttcaag cctattatgg ttttcagccg ttgacggcgt   420
atctctccgt caactacttg gatcgattcc tttgttcacg gcgtttgccg caaactaatg   480
ggtggccttt gcaactactc tctgttgctt gcctctcact ggctgctaaa atggaggaac   540
ctctggttcc tgcttactg gatcttcagg ttgaggggc caaatatata tttgaaccca   600
gaacaatatg caggatggaa ttactggtgc tgagggtatt ggattggcgg ctgcgctctg   660
```

```
taacgccgtt caatttcatc gcattctttg cttgcaagct cgatccatct ggggatttca      720
tggggtttct tatttcaaga gccacagaaa ttataatatc aaatatccga gaggtaatct      780
ttctggagta ctggccatcg tgtatagcgg cggccgcctt gctttgtgca gcaaatgaag      840
tcccgaattt gtctgttgtg aatccagagc atgctgaatc atggtgcagt ggtctaagga      900
aagaaaatat catcggctgc taccggttaa tgcaagagat tgtgcttgat agttgccgga      960
tcgagtcccc caaaatccta cctcagttta gagtgacagt ccgcactaga atgagatcca     1020
gcgacttatc cccctactcc tcttcttcct catcttcgtc atcaccaaac aaaaggagaa     1080
aattaaatca gagcctctgg gtagatgatg acaaagataa ccccgaagaa tgaggagtcc     1140
caaataaaga ggtggcccaa cttttgtccaa aaaaaaaaaa agaagaagaa aaaaggtaga    1200
atcctcgata ttttttggga gggtttagat aataagttaa cataactaga atggtgagtg     1260
ttaattataa tagcatatag tgtaaaagaa tctcagagtt ggggatgagc tgggaggttt     1320
taataattta tttattttc ataatgttgg tgggcaattg ccattcatta atatggcttt      1380
gcagattccc aagggggaa atgggagggg tttgtttgat tttgaggaa atagcgagat       1440
tgttgaataa gtggagttca tagagcagtg gagtgggacc tattttgaga aatgatgaaa     1500
tgggcggtgg ccatatgggt ttcaagttcc aagtttgaag tcagagcaaa agtttcccat    1560
ctccaaccaa cttatttgc tccccaatgg atgggcagta aatagcttga caggtggcgc      1620
tccaatttac ggcttgaaa cggttgtgta tgcccacgct ttttggtgcg tggcatgctc      1680
ttgcgtgtgt gtgtgcgtgt atgtactgta cgtggtcgag ttctcgcccc ttcggctgga    1740
agtgcctctt tttttcaatg gcgttgagcc tactggagtt gttttcacaa ctatatgatc     1800
ttggtggtca tcgattgtg agttcattct ctttttctc ctcactttaa atttatttat       1860
ttttcacagc ctgagttagg tgggaaaaaa tcccaaagta tacgaaaggt ctttggggcc     1920
tttgagtgct tgtttgtatt tggtttcaat caatgtgatt aatttccact caaaaaaaaa    1980
a                                                                    1981

<210> SEQ ID NO 17
<211> LENGTH: 1179
<212> TYPE: DNA
<213> ORGANISM: Cucurbita maxima

<400> SEQUENCE: 17
ctccatctca tcgtcttcct cgctactcat acccacggtt ttttacctttt ttttctggtt     60
cacttgaagt ctccggcggt gtttccggcg gtctttcgga atccgatgag gatgacagtg    120
gctggaagag gatgaaggat actcagttcc tatcatgtcg atctcttctt ccgaagactg    180
ctttattgac tctcatttac tctgtgacga ggactcctcc gatattttgt ccggagagtc    240
gccagagtac tcctcggacc ttgaatcgcc tgccagtagt gaggattcta ttgccagttt    300
catagaggac gagaggcact tcgttcctgg gattgattac ttgtcgcgct tcactctca     360
atcgctcgat tcctccgcaa gagctgactc tgttgcatgg attctcaagg ttcaagcata    420
ttacggtttt caaccactca ctgcataccct ttccgtcaat tacttggatc gattccttta   480
ttctcgccgc ttgccggaaa caatggggtg gccattgcag cttctatcag tggcttgttt    540
gtcacttgca gctaaaatgg aggaaccact tgttccttcg ttcctggatc tccagatcga    600
aggagcaaaa tatatatttg aacctagaac aatacgtagg atggagcttc ttgtacttgc    660
aacattggat tggcggctcc gatccgtaac ccccttcagc ttcatcggat tcttcgccta    720
```

-continued

| | |
|---|---|
| caaagtcgat cccaccggaa cattttccag ttttctcatc tcacgctcca cagaaatcat | 780 |
| tctctccaat attcgagacg ctagctttct tgagtactgg ccttcctgca ttgctgccgc | 840 |
| agccttactt tgtgcggcaa atgaaatacc caatttgacc cttctcaatc ctgaacatgc | 900 |
| agagtcttgg tgcaatggac tcagtaaaga taaaattgtt gggtgttatc gactaatgca | 960 |
| gccatcaaca tcagagagtg gtcgtagaaa gcccccgaaa gtgataccgc aactccgagt | 1020 |
| gagaatccga gctgggttga ggtacagcaa ctcatcgtca tcgtcgtcat caacaaggtt | 1080 |
| aggttataaa aggaggaagt tgaataattg cttgtgggta gaagaagatg acaaagaaaa | 1140 |
| ttccaagttt agagcagagg aataaattta aaaaaaaaa | 1179 |

<210> SEQ ID NO 18
<211> LENGTH: 1954
<212> TYPE: DNA
<213> ORGANISM: Cucumis sativus

<400> SEQUENCE: 18

| | |
|---|---|
| aaaccacttt tttctttacc atcacacaca caccggcgtt aaatattccg tccacttctc | 60 |
| ccatctcttc tccaatctct ttcataaaaa atatggcaat agaatgagga gccagaagcg | 120 |
| gcgatcatgt ccgtatccat ttccaactgc ttctctaatt tactctgcca ggaagattct | 180 |
| tccggcgtct ctccggcga gtccccgggg tgttcttccg acctcgagtc tccagcctgc | 240 |
| gtcgaggaat ctatttccgt cttcatcaag aatgagcgtc acttcgtccc cgattacgac | 300 |
| tgtttctcgc gcttccaatc tccctcgctt gatgccgccg ctagactaga ctctattgca | 360 |
| tggattctta aggttcaagc atattacggt tttcagccgt taacagcgta tctctccgtc | 420 |
| aactatttgg atcgcttcct ttgttcacgc cgtttgccgc aatcaaatgg atggccattg | 480 |
| caacttctct ctgttgcttg tctctcactc gctgctaaaa tggaggaacc acttgttcct | 540 |
| gcattactag atcttcaggt tgaaggggct aaatatatat ttgaacccag aacaatatgc | 600 |
| aggatggaat tattggtcct gagggtatta gattggcggc tacgttcggt aacaccgttc | 660 |
| aatttcatag cattctttgc ctacaagctt gacccatctg gggatttcat tgagtttctt | 720 |
| atctcaagag caacagagat tatactgtca catatccgag aggtaatatt tctggagtac | 780 |
| tggccatctt gtattgcggc ggctgctttg ctttgtgctg caaatgaagt ccagagtttg | 840 |
| tctgttgtca atccagaaca tgctgaatca tggtgcaatg gtctaaggaa agaaaatatc | 900 |
| atgggctgct accggttaat gcaagagatt gtgcttgata taccgaag aaagtctccc | 960 |
| aaaatcttac ctcagtatag agtgacagtc cgcactagaa tgagatccag cgacttatct | 1020 |
| tcttcctact cttcttcttc ttcctcatct tcatcatcac caaacaaaag gagaaaatta | 1080 |
| aaccagaccc atctctgggt acatgaggat aagggtaaca cactgaaga atgatggggt | 1140 |
| ggtgatttca aaacataaag tagaatcctc gatattttt gggagggttt ttttttagat | 1200 |
| ggttaagtta acatttaact agaatggtgg tgcgtgttaa ttatagtaat aatatagtgt | 1260 |
| aatgagatct caaagtttga ggtgggctaa gagatttcaa ataatttttat ttatttatgg | 1320 |
| atcatgttgg tggcaatag ccattcattt aatggctttg cagattccca atgggaaggg | 1380 |
| aaactaaagg gaaagagaga agtttgtttg attttttaagg gaaatggcag agcgttgaat | 1440 |
| aagtggagtc catatggagt gtgaaaatag agaaagtttt gaattctgaa ttcaacagtg | 1500 |
| ggagtgggag tgggagtgga atgagagtgg gaccttatga aggagagagt tattgagaaa | 1560 |
| atgatgaatg gagcagtggc attatggttt caagttccaa gtttgaagtg attttgaatt | 1620 |
| ttggatcaaa agtttctcaa tcttcaacaa cgatattttg gtgataaaat tgataaaggt | 1680 |

```
gactccaatt ttacaacttt tggtgcgtgg catggcatgg gggatggcat gctcttgctt    1740
gtgtgtgtgt attgtatgag tggaactgcc cgccccttcg gctggaggaa gtgcctctgt    1800 ttttttttg ttcttgagtt tgtgtaagtt ttatttttat agctgaaggg gaaaaaaaaa     1860
tcccaattat acagaaaggt ctttggggcc tttgaatgct tgttgtatt ggttttgttc     1920 aatcaatgtg attaattttc attcaaaaaa aaaa                                1954
```

```
<210> SEQ ID NO 19
<211> LENGTH: 1491
<212> TYPE: DNA
<213> ORGANISM: Cucurbita maxima

<400> SEQUENCE: 19
aaaagcctcg ccttttttctc tccttcttaa tctccggcgg tcttttccgg cgccatcttg    60
caggaacggg ggcggaggga cggccagaaa tcgccgactt aaaaaaagtt gaaaagaatt    120
taaagaagac gaccaagaac aagcccatct gcctctgccc ctctgcaacg caatagcttt    180
tttgttctta tttcccaatc aatttctccg tctaaaaaga tcaacagcga ttttttttcca   240 cagtttattt gtaatcggct gtttctggcc tctgttccgc tctgcttttt gcttcaatgg    300
cgcctagttt tgaccttgca gttaccaatc ttttatgcgc tgaagaaaat tgtattttcg    360
atgataacga tgatgacgag tgtctggtcg ctccttatgt tcttacgagt aatgggtttc    420
agagttggcg ccacggcggt ggtcacggcg gcgatgggtt gccgtttaca agcgatgaat    480
gtttgattga aatggtggag aaggaaaccc accacttgcc tgttgatggg tatctcatga    540
aattgcaaaa cggcgagttg gatgtcgggg ctagaaaaga tgctgtcgat tggattgaac    600
aggtgagtgc tcgtttcaat tttggtcctc tctgcacata cttagcccgta aactacatgg    660 atcgattcct ctccgcttac actctaccaa aaggtaaagc ttggacaatg cagctactgg    720
cagtggcatg tctgtctctt gcagccaaat tggaggagac tgaagtccca atctcgttgg    780
atttacaggt gggtggatct aaatttgtgt ttgaagcaag aaccattgaa agaatggagc    840
ttttagtgtt gacaacattg gggtggagaa tgcaagccgt tacgccgttc tcgtttatcg    900
atcattacct ctgtaagatc catcacgacg acaagacatc gatcgcccgt tcgattcatt    960
tactattgaa cataattcaa gggatcgagt tcttggaatt caaaccatct gagattgcag    1020
cagcagtggc aatatcagta gctggagaag gtgaagagac agcaattcct cttctaattc    1080
agcagaaact ccacatggaa agagtagtga agtgcattaa gttagtgaag agatgtcgg    1140 ggaagacgga ggaggaggag tcgaggtcga tgtcggaggg gccgcagagc ccgagcgggg   1200
tattgaacgt gaggtgctta agctataaaa gcaatgaaag tacagcagtt gggtcatgtg    1260
caaattcttc ttcacatcat aacagttcaa atggttcaaa gaggaggaga ttgaacagac    1320
cctgtgaagt ggagctttag tttagaacaa ataaataaaa gggtgatggg aagtgtgatc    1380
ttccagtcct aaagtaaaatt ttttgtgagg attttgaaaa acaggataat tataatatat    1440
aaaaaatata tatatatata taaattttgg aattgtttaa taaaaaaaaa a             1491
```

```
<210> SEQ ID NO 20
<211> LENGTH: 1606
<212> TYPE: DNA
<213> ORGANISM: Cucurbita maxima

<400> SEQUENCE: 20
ctttgttgct tagcttcatt ctgggactgt gtctctctct ctctcctctg ctcaaaaatc    60
```

-continued

| | |
|---|---|
| tcattctcaa tctcaatcca atcgcccagt aacagatacg cctatggata tccctttctc | 120 |
| tttgaccact cccttttctt ctttcgcctt cccattcctc aaatgacata acccttcctc | 180 |
| ctccttttc ttccaacaaa acaccccat ggctctcccg gatgatgaag cccaggttca | 240 |
| ggagattgaa acccagtcct acgttctcga tgccctgttc tgtgaagacc tctgctgcga | 300 |
| cgaagatttc gatggaaatg ggaccgttga agatagcgat tactgggaaa ctctgagaaa | 360 |
| ggaccagcct tttctcgcta ttaatttgct ggaaaaagac ccactttggg aggatgatga | 420 |
| agaattgcag tctctaattt caaaagaaga gcaaacccat gtttgtaatg cttctgttac | 480 |
| ctctgatggg tatctaattc aggctcggaa tgaggcattg tcctggattt ttagtgttaa | 540 |
| acattactac gctttctctg ctttcacctc tcttcttgct gttaactact tcgatagatt | 600 |
| cgtttcaaat gtgaggttcc agagggacaa gccatggatg agtcagcttg cagctgttgc | 660 |
| ttgcctctcg ttggctgcca aagtggagga gacccaggtc ccccttctcc tggaccttca | 720 |
| agtggtagaa tccaagtttt tatttgaagc taagaccata cagagaatgg agctgctggt | 780 |
| gttgtctgcc cttcaatgga agatgcatcc agttactccc ttttcctttc ttcgtcacat | 840 |
| aatcaggagg ttgcctctga aggaccatat gctttgggag cttcttggga ggtttcagag | 900 |
| ccatctcctc tctataatag ctgatcatag attcttgtgc tacctgcctt ctgtcttggc | 960 |
| caccgctaca atattgcata tcattaatga gattgagcca tgtaatttct ggaataccaa | 1020 |
| gaatgagctc ctcagtgtac ttaaaattaa taagaatcat ctagatgaat gctacaaggt | 1080 |
| catccttgat tcacttggca gtaatggcag tgtcaatagc tatcaaatgt gtggactggg | 1140 |
| tagcccacgc gatgttatgg acggatactt catctctgac tcctcgaatg attcatggcc | 1200 |
| aatggtacca tccatctcac cgtagcctaa cactcattga gaaagcgcgc catttggcct | 1260 |
| atgaaatctc tcttgatgct cctacttcct accagccttc tgctgaagca atactcttga | 1320 |
| aattgttctg ggactctctt cacttttcac atgcattata taatatgatg tccaatttgt | 1380 |
| ttttgttgtc gttgcctatt ggggaaaaaa actggtgaga caaggaatca ttgctctgaa | 1440 |
| gatgtgtatt agttctttca ctggtggtgg ggagaaacaa gtgggattg aggagggggaa | 1500 |
| gatcttggtt gggtttctat gttgagttat gaatagtctt ttcatgtact ccatcttgga | 1560 |
| tatagtacta cttcaatttg agaccatatt atttgtaaaa aaaaaa | 1606 |

<210> SEQ ID NO 21
<211> LENGTH: 1608
<212> TYPE: DNA
<213> ORGANISM: Cucurbita maxima

<400> SEQUENCE: 21

| | |
|---|---|
| tttctctctc tctctctttc tcctctcctc tggttcttct tcaatcccct ttttctcagt | 60 |
| tccgccggac atggatggcc ctttgagctc ctcctttttc ctcttttgag tcctctaatc | 120 |
| caagcttcat tcgatggcaa tgcatcgcta tgagccagcc gacgatgaag cccaaaccca | 180 |
| tttgatttcg ctcgattctc tgttttgcga ggaggagaaa tgggaggagg aggaggagga | 240 |
| tgaagatgag ctagaacaga cccatcaagc ccatgttttt tctttggatg ttttggagga | 300 |
| agatctattt ggggaagatg aacgccttct ctccttgttg tctaaggaaa cagagcagct | 360 |
| gaaacagagc aatctcaagc ttgaacctct gttaatggat ccttctgtct ctgctgctcg | 420 |
| ttcttcatct gtggagtgga tgcttaaagt taaatcccat tatgggttct cgtctctcac | 480 |
| tgcaattttg gccgttgctt atttcgacag gttcctctcg agctttcatt ttagaagtga | 540 |
| caagccatgg atgaaccagc ttgtggctgt cacttgcctc tcgttggcgg ctaaagtgga | 600 |

```
ggaggttgaa gttcctctgc tacttgacct tcaagtggag gatgcgaaat ttgtgtttga    660
ggccaaaacc attcagcgaa tggagctttt agtgctgtca actcttcaat ggaggatgca    720
tttggttact tcgtattcat atcttgacaa cattgtaaga aggcttgggt taaagaccaa    780
tcttcatttg gagttcttca agcgttctga gaatctcctc ctttctcttc tctcagattc    840
aagatttgtg ggttatcttc catctgtctt ggcaagtgca acaatgatga acattataga    900
acagattgaa ccccataagt caatggagca ccaagatcat cttctgggtg ttcttaaaat    960
gagcaaggac aaagtgctag gctgttacaa tcttgtagtg gagcattcaa aggcatgtag   1020
caatggctta tatcattcca acaatcccca aagcggaag tacgaacatc atcaagctcc   1080
tgatagccca aatggtgtga ttgatgctgg tttcagttca gacagctcca atgattcatg   1140
ggcattgaga gcagcagcat cagtttgttc ttcacctgaa ccatctttca gaagaacaa   1200
aactgaagag ccaagaatgt tatatcattc tctgaacagg agggtctgtt tggacattgt   1260
tggcagccct tcttagttca taatccgccc ccctttcccc tccaaagaac taggaaatga   1320
ttatgtatgt gttataatgc tctgctccat ttctcacttt tgatatcaaa ttgcttgccc   1380
ataatgttct tggcattaga attggaaggt ggaaggaaga gcagtgatgg ggatttgatg   1440
ggaatgttca caagaacaga agtgaccaga aaaaaatggc attgcagagg agaagacaaa   1500
aagtatgcat ttctacttga tttcaaatca gatcactttc ctttttgttt tggaggaaac   1560
tctcaatatt attaaataaa gcacagcagt tcttggttaa aaaaaaaa              1608
```

<210> SEQ ID NO 22
<211> LENGTH: 1690
<212> TYPE: DNA
<213> ORGANISM: Sicyos angulatus

<400> SEQUENCE: 22

```
cttttccccca atctctctct ctctctctgt tttccccctt ttctctctgc acagttccgg     60
cggccatggc cggcgctctg agccgctccg tttcccccctt ctgagccccc tattcgaagc    120
ttcaatcgat ggccatgcat cggtttgaac aatctgacca tgaagctcaa acccatttga    180
tttcgctcga ttctctgtat tgcgaggagg agaaatggga agatggtgaa gatggtgtag    240
atgatgaaat tgaacaagcc catgaaataa accagaccca tctttttttct ttggggtttt    300
ttgaggaaaa tctctttgaa gaagatgagc ggcttcgatc cctgttgtct aaggaaacag    360
agcagctaga acagagcaat ctggaccttg aagctctgtt aatggatcct tctgtatctg    420
ccgctcgttc ttcggctgtg gagtggatgc tcaaagtcaa atcccattat gggttctcca    480
ctctcactgc aattatggcg gtttcttatt tcgacaggtt tctcttgagc tttcattata    540
agagtgacaa gccgtggatg aaccagcttg tggctgttac ttgtctatcg ctggcggcta    600
aggtggagga gattcatgtt cctcttctgt tggatcttca agttgaggat gctgagtatg    660
tgtttgaggc taaaactatt cagagaatgg agcttcttgt gctctcaact cttcaatgga    720
ggatgcattt tgtgacccca tttctttttc ttgatcatat tgtaaagagg cttggattta    780
aggccaatct tcagttggag tttttaaggt gttctgagca ccttctcctt tctatgctct    840
cagattcaag atttgttggt tatcttccat ctgtgttggc aactgcaaca atgatgaaag    900
ttatagatca tattgaacca catgagtcat tagaacacca agaccagctt tgggtgtcc    960
tcaaaatgag caaggaaaaa gtgcaatgtt gttacaatct tgttgtggag cattcaaagg   1020
cttatggcaa taatggcttt tatcatctca acaatcccta caagcgcaag catgaacatc   1080
```

```
atcaccaagc tccttatagc ccaagtggtg tgattgatgc tggtttcagc tcagacagct   1140
ccaatgattc ttgggcactg agagcatcat catcagtttg ttcatcacct gaatcttctt   1200
tcaagaagac caaaactgaa gagccaaacc tgaaatttca tcctcttaac agggtctttt   1260
tggacattgt tggcagccct tcttaataat tcttcattga tatgccctcc tcctttcctc   1320
ttcaaagtac taggaaatga taatgtttat aaatgctgct ccatttctca gttggggaaa   1380
cttttcttcc attgttgtct aattgcccat aatgcccttg cattagaat ggggaagaag    1440 gaagaagaga gcactgatgg agatttgatg ggaactttca caagaacaga agtgaccaga   1500
agaaatgggc attggagaag acaaaaaagt atgcagtctg gctttctact ctctaaaaaa   1560
actgtataca tttctgtcat ttcccatcct atttgatttc atatcatcat atcactttcc   1620
tttttgtttt ggacaaaact catatattat tattaaataa agcacagca tttcttttc     1680 aaaaaaaaa                                                           1690

<210> SEQ ID NO 23
<211> LENGTH: 1920
<212> TYPE: DNA
<213> ORGANISM: Arabidopsis thaliana

<400> SEQUENCE: 23
attgtaagtt tgggtgtgat ttttaaaaaa tcaaaagttc cagggttatt tcataaatac     60
cgaaagatcc gaggcggttt catcatatac tgggcgatcc gtggtggttt cgaatatacc    120
gaaagatccg ggagcatttt gaatctgctg aaagatctgg ggcgatttcg tagataccaa    180
aatatctgtg gtgatttcgt ctcacagttt caatcgtcga taatcattag ggtaaagcaa    240
aaatagtgaa gcagagccgc aaaaacactt ttcccaaaat caacgaagat agattccagat   300 cggaagcgaa agaacgattc ggtctcctcc acagatcgaa catcgaagga gaagaaagac    360
catcatcaca acaagcatcg aaagaagagc aagatggcgt cgagagacca agttaaggca    420
tcgcacattt tgattaagca tcaaggttct cggaggaaag cgtcgtggaa ggatccagaa    480
gggaagatta ttctgactac cactagagaa gccgccgttg agcagcttaa atcgatccgt    540
gaagatattg tctccggcaa ggcgaatttc gaagaagtgg cgactcgtgt ttctgactgt    600
agctctgcta aacgcggcgg tgatcttggt ttgttcttat ccctaatctc tagatcagcg    660
agtttaggtt taggatgatt gaacttaggg ttagatctag tggcaattaa gattttagga    720
aatgaagtta atctgtatag tctcaagtga tgtttgttga aggagtagaa agcttgttaa    780
ctggattcta ttggatctaa ctctttacag tgaaattgag cataatgatc atagcttaga    840
tcattagtga tgtttagaat ctcacagttc ttcctcgatg tgtttatagt catcactaat    900
gtttagaatc tatagtttct agcttgataa atctttagtt ggtgctcaga aattttacta    960
atctctagct tctatcatca ttaatgttta gcttcttcat attccttaat aaatctattc   1020
ttggctctcg ttaatctcac taatgtctgt ttagataatc accgatgttg agagtctaaa   1080
gtttatcttc cttgatgaat ctatatcggt gctcacaagt cttactattg tccacttaga   1140
tcaacatcga tgattagaaa ctaaagttta ttccttgatg tatctttagt tggtgctcgt   1200
aaatcttact actgtttgct tagagcataa ctatgtttat aatctaaagt gtattccttg   1260
atgaatccat aatcggtgct cataaatctt actaatgtcc acttagatca ctacccatgt   1320
tttcctcgtg atgatttata attggtgctc atcaagttta ctaacatctt cgtagatcat   1380
ctcccacata gagtttcttt cttgatgaat ctataatttg tgctcataaa tcttatgttg   1440
atttgtccat ccctgttcag gttcctttgg tagaggtcaa atgcagaaac catttgagga   1500
```

```
agcaacttac gcgctcaagg ttggagatat aagcgacatt gtcgatacag acagtggagt    1560
ccacatcatt aagagaacag cttgaccttga tctgatctga tagaaaatgt attgaaggtg    1620
```

```
agcaacttac gcgctcaagg ttggagatat aagcgacatt gtcgatacag acagtggagt   1560
ccacatcatt aagagaacag cttgaccttta tctgatctga tagaaaatgt attgaaggtg   1620
cctgcttcgt ttcccttctc ttcttgacca gaagaacata gaagaagaag aataagaaga   1680
atttaattca aggttattgt tattgtggtt ttgattctga atctgtctac gaatttgata   1740
caactcaaac atatgataaa atcagacaag ctatctcatt tcttcttaaa ggcttcataa   1800
gcactccctg tcgtagacag tgacttgtat aatcacattt cagtatcttt gtcatggtct   1860
tactgcaaca ttctggcatc ttgtgtgttg tcattttgct cttaaactct tgatagtctt   1920
```

<210> SEQ ID NO 24
<211> LENGTH: 22
<212> TYPE: DNA
<213> ORGANISM: Artificial Sequence
<220> FEATURE:
<223> OTHER INFORMATION: Made in the lab

<400> SEQUENCE: 24
cggtctcctc cacagatcga ac                                              22

<210> SEQ ID NO 25
<211> LENGTH: 21
<212> TYPE: DNA
<213> ORGANISM: Artificial Sequence
<220> FEATURE:
<223> OTHER INFORMATION: Made in the lab

<400> SEQUENCE: 25
cttcataagc actccctgtc g                                               21

<210> SEQ ID NO 26
<211> LENGTH: 662
<212> TYPE: DNA
<213> ORGANISM: Arabidopsis thaliana

<400> SEQUENCE: 26

```
cggtctcctc cacagatcga acatcgaagg agaagaaaga ccatcatcac aacaagcatc    60
gaaagaagag caagatggcg tcgagagacc aagttaaggc atcgcacatt ttgattaagc   120
atcaaggttc tcggaggaaa gcgtcgtgga aggatccaga agggaagatt attctgacta   180
ccactagaga agccgccgtt gagcagctta atcgatccg tgaagatatt gtctccggca    240
aggcgaattt cgaagaagtg gcgactcgtg tttctgactg tagctctgct aaacgcggcg   300
gtgatcttgg ttcctttggt agaggtcaaa tgcagaaacc atttgaggaa gcaacttacg   360
cgctcaaggt tggagatata agcgacattg tcgatacaga cagtggagtc cacatcatta   420
agagaacagc ttgaccttat ctgatctgat agaaaatgta ttgaaggtgc ctgcttcgtt   480
tcccttctct tcttgaccag aagaacatag aagaagaaga ataagaagaa tttaattcaa   540
ggttattgtt attgtggttt tgattctgaa tctgtctacg aatttgatac aactcaaaca   600
tatgataaaa tcagacaagc tatctcattt cttcttaaag gcttcataag cactccctgt   660
cg                                                                   662
```

<210> SEQ ID NO 27
<211> LENGTH: 652
<212> TYPE: PRT
<213> ORGANISM: Eucalyptus grandis

<400> SEQUENCE: 27

-continued

```
Met Ile Lys Trp His Asp Leu Tyr Ala Val Leu Val Ala Val Val Pro
 1               5                  10                  15

Leu Tyr Val Ala Met Ile Leu Ala Tyr Gly Ser Val Arg Trp Trp Arg
                20                  25                  30

Ile Phe Ser Pro Asp Gln Cys Ser Gly Ile Asn Arg Phe Val Ala Ile
            35                  40                  45

Phe Ala Val Pro Leu Leu Ser Phe His Phe Ile Ser Thr Asn Asp Pro
 50                  55                  60

Tyr Arg Met Asn Leu Arg Phe Ile Ala Ala Asp Thr Leu Gln Lys Leu
 65                  70                  75                  80

Leu Leu Leu Leu Leu Ala Leu Trp Ala Asn Leu His Arg Arg Gly
                85                  90                  95

Ser Leu Asp Trp Ser Ile Thr Val Phe Ser Leu Ser Thr Leu Pro Asn
            100                 105                 110

Thr Leu Val Met Gly Ile Pro Leu Leu Gly Ala Met Tyr Gly Thr Glu
            115                 120                 125

Ala Ser Asn Leu Met Val Gln Val Val Leu Gln Cys Ile Ile Trp
 130                 135                 140

Tyr Thr Leu Leu Leu Phe Leu Phe Glu Tyr Arg Gly Ala Lys Ile Leu
 145                 150                 155                 160

Ile Met Glu Gln Phe Pro Glu Thr Ala Ala Ser Ile Val Ser Phe Asn
            165                 170                 175

Val Asp Pro Asp Val Val Ser Leu Asp Gly Arg Asn Phe Leu Glu Thr
            180                 185                 190

Asp Ala Glu Val Gly Gln Asp Gly Lys Leu His Val Thr Val Arg Lys
            195                 200                 205

Ser Asn Ala Ser Arg Arg Ser Phe Gly Leu Gly Pro Gly Gly Gly
 210                 215                 220

Ser Phe Ser Gly Met Thr Pro Arg Pro Ser Asn Leu Ser Gly Val Glu
225                 230                 235                 240

Ile Tyr Ser Leu Ser Ser Arg Asn Leu Thr Pro Arg Gly Ser Asn
            245                 250                 255

Ser Asp Phe Tyr Ser Ile Met Gly Val Pro Arg Leu Ser Asn Phe Gly
            260                 265                 270

Pro Ser Asp Ala Tyr Ser Val Gln Ser Ser Arg Gly Pro Thr Pro Arg
            275                 280                 285

Pro Ser Asn Phe Asp Glu Asn Leu Gln Pro Ser Pro Lys Phe Gly Phe
            290                 295                 300

Tyr Pro Ala Gln Val Ala Ser Ala Pro Tyr Pro Ala Pro Ile Pro Asp
305                 310                 315                 320

Phe Ala Ser Ala Phe Ala Lys Ser Gly Lys Pro Asn Gln Gln Gln
            325                 330                 335

Gln Pro Ala Pro Ala Pro Pro Glu Gln Gln Ser Asn Gly Ala Ala Lys
            340                 345                 350

Ala Asn Ser Tyr Asp Ala Lys Glu Leu His Met Phe Val Trp Ser Ser
            355                 360                 365

Ser Ala Ser Pro Val Ser Glu Val Gly Gly Leu His Val Phe Gly Ser
            370                 375                 380

Gly Asp Phe Gly Ala Pro Asp Asn Gln Ser Arg Arg Ala Asp His Ser
385                 390                 395                 400

Val Lys Glu Ile Arg Met Met Val Ala Asp Asn Asn Gln Pro Asn Gly
            405                 410                 415

Glu Thr Lys Thr Ala Pro Glu Thr Thr Gly Phe Thr Gly Gln Asp Gln
```

-continued

```
                420                 425                 430
Phe Asn Phe Val Ala Lys Ala Asp Glu Arg Asp Glu Gly Thr Gly Gly
            435                 440                 445
Glu Lys Glu Ala Ala Gly Pro Asp Arg Pro Asn Lys Leu Cys Ala Ser
450                 455                 460
Ser Ser Ala Gly Glu Pro Gly Tyr Gly Gly Gly Asp Asp Ala Gly
465                 470                 475                 480
Asn Asp Lys Gln Met Pro Pro Ala Ser Val Met Thr Arg Leu Ile Leu
                485                 490                 495
Ile Met Val Trp Arg Lys Leu Ile Arg Asn Pro Asn Thr Tyr Ser Ser
            500                 505                 510
Leu Ile Gly Ile Ile Trp Ser Leu Ile Ala Phe Arg Trp Asp Val Gly
            515                 520                 525
Met Pro Glu Ile Val Asp Lys Ser Ile His Ile Leu Ser Asp Ala Gly
            530                 535                 540
Leu Gly Met Ala Met Phe Ser Leu Gly Leu Phe Met Ala Leu Gln Pro
545                 550                 555                 560
Lys Leu Ile Ala Cys Gly Asn Ser Val Ala Thr Phe Ala Met Ala Val
                565                 570                 575
Arg Phe Leu Val Gly Pro Ala Ala Met Ala Ile Ala Ser Ala Ala Ile
            580                 585                 590
Gly Leu Arg Gly Pro Leu Leu His Ile Ala Ile Val Gln Ala Ala Leu
            595                 600                 605
Pro Gln Gly Ile Val Pro Phe Val Phe Ala Lys Glu Tyr Asn Val His
            610                 615                 620
Pro Ala Val Leu Ser Thr Met Val Ile Phe Gly Met Leu Ile Ala Leu
625                 630                 635                 640
Pro Ile Thr Leu Val Tyr Tyr Ile Leu Leu Gly Leu
                        645                 650

<210> SEQ ID NO 28
<211> LENGTH: 588
<212> TYPE: PRT
<213> ORGANISM: Eucalyptus grandis

<400> SEQUENCE: 28

Met Ile Thr Gly Ser Asp Phe Tyr His Val Met Thr Ala Met Val Pro
1               5                   10                  15
Leu Tyr Val Ala Met Ile Leu Ala Tyr Gly Ser Val Arg Trp Trp Arg
            20                  25                  30
Ile Phe Thr Pro Asp Gln Cys Ser Gly Ile Asn Arg Phe Val Ala Leu
            35                  40                  45
Phe Ala Val Pro Leu Leu Ser Phe His Phe Ile Ser Ser Asn Asn Pro
        50                  55                  60
Phe Thr Met Asn Leu Arg Phe Leu Ala Ala Asp Ser Leu Gln Lys Leu
65                  70                  75                  80
Leu Ile Leu Leu Ala Leu Ala Leu Trp Ser His Leu Ser Arg Arg Gly
                85                  90                  95
Ser Leu Asp Trp Ser Ile Thr Leu Phe Ser Leu Ser Thr Leu Pro Asn
            100                 105                 110
Thr Leu Val Met Gly Ile Pro Leu Leu Arg Gly Met Tyr Gly Pro Tyr
            115                 120                 125
Ser Gly Asp Leu Met Val Gln Ile Val Val Leu Gln Cys Ile Ile Trp
        130                 135                 140
```

```
Tyr Thr Leu Met Leu Phe Leu Phe Glu Phe Arg Ala Ala Arg Thr Leu
145                 150                 155                 160

Ile Ser Asn Gln Phe Pro Gly Thr Ala Ala Ser Ile Ile Ser Ile
            165                 170                 175

Arg Val Asp Pro Asp Val Val Ser Ala Cys Thr Asp Pro Arg Gln Ser
            180                 185                 190

Leu Glu Thr Glu Ala Glu Val Gly Ser Asp Gly Lys Leu Arg Val Thr
            195                 200                 205

Val Arg Arg Ser Ser Ala Ser Arg Ser Asp Ile Phe Lys Pro Ala Ala
            210                 215                 220

Trp Leu Ser Pro Arg Pro Ser Asn Leu Thr Asn Ala Glu Ile Tyr Ser
225                 230                 235                 240

Leu Gln Ser Ser Arg Asn Pro Thr Pro Arg Gly Ser Ser Phe Asn His
            245                 250                 255

Ala Glu Leu Tyr Ser Val Ala Ala Gly Leu Gly Gly Gly Arg Gly
            260                 265                 270

Ser Asn Phe Gly Ser Ala Asp Val Tyr Gly Leu Ser Ala Pro Phe Gly
            275                 280                 285

Pro Thr Pro Arg Pro Ser Asn Tyr Glu Glu Asp Lys Pro Lys Phe Pro
290                 295                 300

Tyr Gly Ser Gly Gly Ser Thr Ala Gly Ser Tyr Pro Ala Pro Asn Pro
305                 310                 315                 320

Gly Met Phe Ser Pro Lys Asn Asn Gly Gly Ser Gly Gly Lys Arg Ala
                325                 330                 335

Asn Val Gln Gly Gly Lys Arg Gly Ala Glu Asp Gly Gly Gly Gly
            340                 345                 350

Arg Arg Asp Leu His Met Phe Val Trp Ser Ser Thr Ser Pro Val
            355                 360                 365

Ser Asp Val Phe Gly Asn Asn His Asp Leu Pro Thr Gly Ala Thr His
    370                 375                 380

Glu Lys Val Asp Gln Asn His Ile Lys Glu Gly Asp Gln Leu Glu Arg
385                 390                 395                 400

Asp Glu Phe Ser Phe Arg Asn Arg Arg Pro Glu Asn Val Glu Ala Gly
                405                 410                 415

Gly Gly Asp Ala Met Pro Pro Thr Ser Val Met Thr Arg Leu Ile Leu
            420                 425                 430

Ile Met Val Trp Arg Lys Leu Ile Arg Asn Pro Asn Thr Tyr Ser Ser
            435                 440                 445

Leu Ile Gly Ile Thr Trp Ser Leu Val Ser Phe Arg Trp His Ile Glu
    450                 455                 460

Met Pro Ala Ile Ile Ala Lys Ser Ile Ser Ile Leu Ser Asp Ala Gly
465                 470                 475                 480

Leu Gly Met Ala Met Phe Ser Leu Gly Leu Phe Met Ala Leu Gln Pro
            485                 490                 495

Lys Ile Ile Ala Cys Gly Asn Ser Val Ala Thr Phe Ala Met Ala Val
            500                 505                 510

Arg Phe Leu Thr Gly Pro Ala Val Met Ala Ala Ala Ser Leu Val Ile
            515                 520                 525

Gly Leu Arg Gly Asp Leu Leu Arg Val Ala Ile Val Gln Ala Ala Leu
            530                 535                 540

Pro Gln Gly Ile Val Pro Phe Val Phe Ala Lys Glu Tyr Gly Leu His
545                 550                 555                 560

Pro Asp Ile Leu Ser Thr Ala Val Ile Phe Gly Met Leu Ile Ala Leu
```

```
                565                 570                 575
Pro Ile Thr Leu Val Tyr Tyr Ile Phe Leu Gly Ile
            580                 585

<210> SEQ ID NO 29
<211> LENGTH: 577
<212> TYPE: PRT
<213> ORGANISM: Eucalyptus grandis

<400> SEQUENCE: 29

Met Gly Ser Lys Glu Ile Cys Arg Asn Glu Leu Arg Ile Ala Val Arg
 1               5                  10                  15

Gln Leu Ser Asp Arg Cys Leu Tyr Ser Ala Ser Lys Trp Ala Ala Glu
            20                  25                  30

Gln Leu Val Gly Ile Glu Leu Asp Pro Val Lys Phe Thr Pro Ser Asn
        35                  40                  45

Thr Arg Phe Gln Arg Gly Ser Ser Ile Arg Arg Phe Arg Thr
    50                  55                  60

Asn Glu Ile Met Ser Thr Pro Ile Ala Gly Val Ser Tyr Val Ser Thr
65                  70                  75                  80

Pro Val Met Glu Glu Asp Ile Val Asp Gly Asp Phe Tyr Leu Leu
                85                  90                  95

Ala Lys Ser Tyr Phe Asp Cys Arg Glu Tyr Arg Arg Ala Ala His Val
            100                 105                 110

Leu Arg Asp Gln Tyr Gly Lys Lys Ala Val Phe Leu Arg Cys Tyr Ala
        115                 120                 125

Leu Tyr Leu Ala Gly Glu Asn Arg Lys Asp Glu Glu Asn Ile Glu Leu
    130                 135                 140

Glu Gly Pro Leu Gly Lys Ser Asp Ala Val Asn Lys Glu Leu Val Ser
145                 150                 155                 160

Leu Glu Arg Glu Leu Ser Met Leu Arg Lys Asn Gly Ser Ile Asp Pro
                165                 170                 175

Phe Gly Leu Tyr Leu Tyr Gly Leu Val Leu Lys Glu Lys Gly Ser Glu
            180                 185                 190

His Leu Ala Arg Asn Leu Leu Val Glu Ser Val Asn Ser Tyr Pro Trp
        195                 200                 205

Asn Trp Ser Ala Trp Ser Glu Leu Gln Ser Leu Cys Thr Thr Ile Asp
    210                 215                 220

Ile Leu His Ser Leu Pro Leu Asn Asn His Trp Met Lys Asp Phe Phe
225                 230                 235                 240

Leu Ala Gly Ala Tyr Gln Glu Leu Arg Met His Asn Glu Ser Leu Ala
                245                 250                 255

Lys Tyr Glu Tyr Leu Gln Gly Thr Phe Ser Phe Ser Asn Tyr Ile Gln
            260                 265                 270

Ala Gln Ile Ala Lys Ala Gln Tyr Ser Leu Arg Glu Phe Glu Gln Val
        275                 280                 285

Glu Val Ile Phe Glu Glu Leu Leu Arg Asn Asp Pro Tyr Arg Val Glu
    290                 295                 300

Asp Met Asp Met Tyr Ser Asn Val Leu Tyr Ala Lys Glu Cys Phe Ser
305                 310                 315                 320

Ala Leu Ser Tyr Leu Ala His Arg Val Phe Met Thr Asp Lys Tyr Arg
                325                 330                 335

Pro Glu Ser Cys Cys Ile Ile Gly Asn Tyr Tyr Ser Leu Lys Gly Gln
            340                 345                 350
```

```
His Glu Lys Ser Val Met Tyr Phe Arg Arg Ala Leu Lys Leu Asn Lys
            355                 360                 365

Asn Cys Leu Ser Ala Trp Thr Leu Met Gly His Glu Tyr Val Glu Met
        370                 375                 380

Lys Asn Thr Pro Ala Ala Val Asp Ala Tyr Arg Arg Ala Val Asp Ile
385                 390                 395                 400

Asn Pro Cys Asp Tyr Arg Ala Trp Tyr Gly Leu Gly Gln Ala Tyr Glu
                405                 410                 415

Met Met Gly Met Pro Phe Tyr Ala Leu His Tyr Phe Arg Lys Ser Val
            420                 425                 430

Phe Leu Gln Pro Ser Asp Ser Arg Leu Trp Ile Ala Met Ala Gln Cys
        435                 440                 445

Tyr Glu Thr Glu Gln Leu His Met Leu Glu Glu Ser Ile Lys Cys Tyr
    450                 455                 460

Arg Arg Ala Ala Asn Cys Asn Asp Arg Glu Ala Ile Ala Leu His Lys
465                 470                 475                 480

Leu Ala Lys Leu His Cys Glu Leu Gly Arg Leu Glu Glu Ala Ala Phe
                485                 490                 495

Tyr Tyr Lys Lys Asp Leu Glu Arg Met Glu Ala Glu Glu Arg Asp Gly
            500                 505                 510

Pro Asn Met Val Glu Ala Leu Leu Phe Leu Ala Thr His Gly Lys Asp
        515                 520                 525

Gln Lys Arg Phe Glu Glu Ala Glu Val Tyr Cys Thr Arg Leu Leu Asp
    530                 535                 540

Tyr Thr Gly Pro Glu Lys Glu Thr Ala Lys Ser Leu Leu Arg Gly Met
545                 550                 555                 560

Arg Met Ala Gln Ser Gly Phe Pro Ser Met Ser Ala Glu His Phe Pro
                565                 570                 575

Pro

<210> SEQ ID NO 30
<211> LENGTH: 105
<212> TYPE: PRT
<213> ORGANISM: Pinus radiata

<400> SEQUENCE: 30

Met Asp Gln Ile Glu Tyr Ser Glu Lys Tyr Tyr Asp Asp Thr Tyr Glu
  1               5                  10                  15

Tyr Arg His Val Glu Leu Pro Pro Asp Val Ala Arg Leu Leu Pro Lys
                 20                  25                  30

Asn Arg Leu Leu Thr Glu Asn Glu Trp Arg Gly Ile Gly Val Gln Gln
             35                  40                  45

Ser Arg Gly Trp Val His Tyr Ala Ile His Cys Ser Glu Pro His Ile
     50                  55                  60

Met Leu Phe Arg Arg Pro Leu Asn Tyr Glu Gln Asn His Gln His Pro
 65                  70                  75                  80

Glu Pro His Ile Met Leu Phe Arg Arg Pro Leu Asn Cys Gln Pro Asn
                 85                  90                  95

His Gln Pro Gln Ala His His Pro Thr
             100                 105

<210> SEQ ID NO 31
<211> LENGTH: 93
<212> TYPE: PRT
<213> ORGANISM: Pinus radiata
```

```
<400> SEQUENCE: 31

Met Pro Gln Ile Gln Tyr Ser Glu Lys Tyr Thr Asp Asp Thr Tyr Glu
1               5                   10                  15

Tyr Arg His Val Val Leu Pro Pro Glu Thr Ala Lys Leu Leu Pro Lys
            20                  25                  30

Asn Arg Leu Leu Asn Glu Asn Glu Trp Arg Ala Ile Gly Val Gln Gln
        35                  40                  45

Ser Arg Gly Trp Val His Tyr Ala Ile His Arg Pro Glu Pro His Ile
    50                  55                  60

Met Leu Phe Arg Arg Pro Leu Asn Tyr Gln Gln Asn Gln Gln Gln Gln
65                  70                  75                  80

Ala Gly Ala Gln Ser Gln Pro Met Gly Leu Lys Ala Gln
                85                  90

<210> SEQ ID NO 32
<211> LENGTH: 797
<212> TYPE: PRT
<213> ORGANISM: Pinus radiata

<400> SEQUENCE: 32

Met Gly Cys Val Cys Ala Lys Gln Ser Asp Ile Leu Gly Glu Pro Glu
1               5                   10                  15

Ser Pro Lys Val Lys Gly Ser Asn Leu Ala Ser Ser Arg Trp Ser Val
            20                  25                  30

Ser Ser Glu Thr Lys Gln Leu Pro Gln His Ser Asp Ser Gly Ile Leu
        35                  40                  45

His His Gln His Tyr Tyr His Pro Arg Asp Glu Ser Asp Glu Ala Lys
    50                  55                  60

Leu Lys Glu Ser Asn Tyr Gly Gly Ser Lys Arg Thr Arg Gln Gly
65                  70                  75                  80

Arg Asp Pro Ala Asp Leu Asp Met Gly Ile Phe Val Arg Thr Pro Ser
                85                  90                  95

Ser Gln Ser Glu Ala Glu Leu Val Ala Ala Gly Trp Pro Ala Trp Met
            100                 105                 110

Ala Ala Phe Ala Gly Glu Ala Ile His Gly Trp Ile Pro Arg Arg Ala
        115                 120                 125

Glu Ser Phe Glu Lys Leu Tyr Lys Ile Gly Gln Gly Thr Tyr Ser Asn
    130                 135                 140

Val Tyr Lys Ala Arg Asp Leu Asp Asn Gly Lys Ile Val Ala Leu Lys
145                 150                 155                 160

Lys Val Arg Phe Asp Ser Leu Asp Ala Glu Ser Val Arg Phe Met Ala
                165                 170                 175

Arg Glu Ile Leu Val Leu Arg Lys Leu Asp His Pro Asn Ile Val Lys
            180                 185                 190

Leu Glu Gly Leu Val Thr Ser Glu Val Ser Ser Ser Leu Tyr Leu Val
        195                 200                 205

Phe Glu Tyr Met Glu His Asp Leu Ala Gly Leu Ala Ala Cys Pro Gly
    210                 215                 220

Ile Lys Phe Thr Glu Pro Gln Val Lys Cys Tyr Met Gln Gln Leu Leu
225                 230                 235                 240

Gln Gly Leu Asp His Cys His Arg His Gly Val Leu His Arg Asp Ile
                245                 250                 255

Lys Gly Ser Asn Leu Leu Ile Asp Asn Gly Gly Ile Leu Lys Ile Ala
            260                 265                 270
```

-continued

```
Asp Phe Gly Leu Ala Thr Phe Phe Tyr Pro Asp Gln Lys Gln Leu Leu
            275                 280                 285

Thr Ser Arg Val Val Thr Leu Trp Tyr Arg Pro Pro Glu Leu Leu Leu
    290                 295                 300

Gly Ala Thr Asp Tyr Gly Val Ala Val Asp Ile Trp Ser Ala Gly Cys
305                 310                 315                 320

Ile Leu Ala Glu Leu Leu Ala Gly Lys Pro Ile Leu Pro Gly Arg Thr
                325                 330                 335

Glu Val Glu Gln Leu His Lys Ile Phe Lys Leu Cys Gly Ser Pro Ser
            340                 345                 350

Glu Asp Tyr Trp Lys Glu Ser Lys Leu Pro His Ala Thr Ile Phe Lys
        355                 360                 365

Pro Gln His Pro Tyr Lys Ser Cys Ile Ala Glu Ala Phe Lys Asp Phe
    370                 375                 380

Ser Pro Ser Ala Leu Ala Leu Leu Glu Thr Leu Leu Ala Ile Glu Pro
385                 390                 395                 400

Gly His Arg Gly Glu Ala Ser Gly Ala Leu Lys Ser Glu Phe Phe Thr
                405                 410                 415

Thr Glu Pro Leu Ser Cys Asp Pro Ser Ser Leu Pro Lys Tyr Pro Pro
            420                 425                 430

Ser Lys Glu Phe Asp Ala Lys Leu Arg Ala Gln Glu Thr Arg Arg Gln
        435                 440                 445

Arg Asp Val Gly Val Arg Gly His Gly Ser Glu Ala Ala Arg Arg Thr
    450                 455                 460

Ser Arg Leu Ser Arg Ala Gly Pro Thr Pro Asn Glu Gly Ala Glu Leu
465                 470                 475                 480

Thr Ala Leu Thr Gln Lys Gln His Ser Thr Ser His Ala Thr Ser Asn
                485                 490                 495

Ile Gly Ser Glu Lys Pro Ser Thr Lys Lys Glu Asp Tyr Thr Ala Gly
            500                 505                 510

Leu His Ile Asp Pro Pro Arg Pro Val Asn His Ser Tyr Glu Thr Thr
        515                 520                 525

Gly Val Ser Arg Ala Tyr Asp Ala Ile Arg Gly Val Ala Tyr Ser Gly
    530                 535                 540

Pro Leu Ser Gln Thr His Val Ser Gly Ser Thr Ser Gly Lys Lys Pro
545                 550                 555                 560

Lys Arg Asp His Val Lys Gly Leu Ser Gly Gln Ser Ser Leu Gln Pro
                565                 570                 575

Ser Lys Pro Phe Ile Val Ser Asp Ser Arg Ser Glu Arg Ile Tyr Glu
            580                 585                 590

Lys Ser His Val Thr Asp Leu Ser Asn His Ser Arg Leu Ala Val Gly
        595                 600                 605

Arg Asn Arg Asp Thr Thr Asp Pro His Lys Ser Leu Ser Thr Leu Met
    610                 615                 620

Gln Gln Ile Gln Asp Gly Thr Leu Asp Gly Ile Asp Ile Gly Thr His
625                 630                 635                 640

Glu Tyr Ala Arg Ala Pro Val Ser Ser Thr Lys Gln Lys Ser Ala Gln
                645                 650                 655

Leu Gln Arg Pro Ser Thr Leu Lys Tyr Val Asp Asn Val Gln Leu Gln
            660                 665                 670

Asn Thr Arg Val Gly Ser Arg Gln Ser Asp Glu Arg Pro Ala Asn Lys
        675                 680                 685

Glu Ser Asp Met Val Ser His Arg Gln Gly Gln Arg Ile His Cys Ser
```

```
                690              695              700
Gly Pro Leu Leu His Pro Ser Ala Asn Ile Glu Asp Leu Leu Gln Lys
705                      710                  715                  720

His Glu Gln Gln Ile Gln Gln Ala Val Arg Arg Ala His His Gly Lys
                725                  730                  735

Arg Glu Ala Leu Ser Asn Lys Ser Ser Leu Pro Gly Lys Lys Pro Val
            740                  745                  750

Asp His Arg Ala Trp Val Ser Ser Gly Lys Gly Asn Lys Glu Ser Pro
        755                  760                  765

Tyr Phe Lys Gly Lys Gly Asn Lys Glu Leu Ser Asp Leu Lys Gly Gly
    770                  775                  780

Pro Thr Ala Lys Val Thr Asn Phe Arg Gln Lys Val Met
785                  790                  795

<210> SEQ ID NO 33
<211> LENGTH: 200
<212> TYPE: PRT
<213> ORGANISM: Eucalyptus grandis

<400> SEQUENCE: 33

Met Ala Thr Ser Gly Asn Lys Asn Ile Asn Ala Lys Leu Val Leu Leu
1               5                   10                  15

Gly Asp Val Gly Ala Gly Lys Ser Ser Leu Val Leu Arg Phe Val Lys
            20                  25                  30

Gly Gln Phe Val Glu Phe Gln Glu Ser Thr Ile Gly Ala Ala Phe Phe
        35                  40                  45

Ser Gln Thr Leu Ala Val Asn Asp Ala Thr Val Lys Phe Glu Ile Trp
    50                  55                  60

Asp Thr Ala Gly Gln Glu Arg Tyr His Ser Leu Ala Pro Met Tyr Tyr
65                  70                  75                  80

Arg Gly Ala Ala Ala Ile Ile Val Tyr Asp Met Thr Asn Leu Ala
                85                  90                  95

Ser Phe Glu Arg Ala Lys Lys Trp Val Gln Glu Leu Gln Ala Gln Gly
            100                 105                 110

Asn Pro Asn Met Val Met Ala Leu Ala Gly Asn Lys Ala Asp Leu Leu
        115                 120                 125

Asp Ala Arg Lys Val Thr Ala Glu Glu Ala Gln Thr Tyr Ala Gln Glu
    130                 135                 140

His Gly Leu Phe Phe Met Glu Thr Ser Ala Lys Thr Ala Ala Asn Val
145                 150                 155                 160

Asn Asp Ile Phe Tyr Glu Ile Ala Lys Arg Leu Pro Arg Ala Gln Pro
                165                 170                 175

Ala Pro Asn Pro Ser Gly Met Val Leu Met Asp Arg Pro Ala Glu Arg
            180                 185                 190

Thr Ala Ala Ser Cys Cys Ser
        195                 200

<210> SEQ ID NO 34
<211> LENGTH: 196
<212> TYPE: PRT
<213> ORGANISM: Eucalyptus grandis

<400> SEQUENCE: 34

Met Ser Glu Ile Arg Arg Lys Leu Val Ile Val Gly Asp Gly Ala Cys
1               5                   10                  15

Gly Lys Thr Cys Leu Leu Ile Val Phe Ser Lys Gly Thr Phe Pro Glu
```

-continued

```
                20                  25                  30
Val Tyr Val Pro Thr Val Phe Glu Asn Tyr Val Ala Asp Val Val
            35                  40                  45

Asp Gly Lys Arg Val Glu Leu Ala Leu Trp Asp Thr Ala Gly Gln Glu
 50                      55                  60

Asp Tyr Asp Arg Leu Arg Pro Leu Ser Tyr Pro Asp Ser His Val Ile
 65                  70                  75                  80

Leu Ile Cys Phe Ala Val Asp Ser Pro Asp Ser Leu Asp Asn Val Gln
                 85                  90                  95

Glu Lys Trp Ile Ser Glu Val Leu His Phe Cys Ser Gly Leu Pro Ile
             100                 105                 110

Ile Leu Val Gly Cys Lys Lys Asp Leu Arg His Asp Pro Lys Thr Val
         115                 120                 125

Asp Glu Leu Arg Arg Thr Ser Gln Arg Pro Val Thr Ser Gln Glu Gly
     130                 135                 140

Asp Ser Val Arg Gln Lys Ile Gly Ala Thr Arg Tyr Leu Glu Cys Ser
145                 150                 155                 160

Ala Lys Thr Gly Glu Gly Val Arg Glu Val Phe Glu Gln Ala Thr Arg
                165                 170                 175

Leu Ala Leu Leu Ser Gln Lys Gly Gly Lys Gly Gly Lys Lys Gly Lys
            180                 185                 190

Cys Thr Val Leu
        195

<210> SEQ ID NO 35
<211> LENGTH: 211
<212> TYPE: PRT
<213> ORGANISM: Eucalyptus grandis

<400> SEQUENCE: 35

Met Ser Tyr Asp Tyr Leu Phe Lys Tyr Ile Ile Gly Asp Thr Gly
 1               5                  10                  15

Val Gly Lys Ser Cys Leu Leu Leu Gln Phe Thr Asp Lys Arg Phe Gln
                20                  25                  30

Pro Val His Asp Leu Thr Ile Gly Val Glu Phe Gly Ala Arg Met Val
             35                  40                  45

Thr Ile Asp Gly Arg Pro Ile Lys Leu Gln Ile Trp Asp Thr Ala Gly
         50                  55                  60

Gln Glu Ser Phe Arg Ser Ile Thr Arg Ser Tyr Tyr Arg Gly Ala Ala
 65                  70                  75                  80

Gly Ala Leu Leu Val Tyr Asp Ile Thr Arg Arg Asp Thr Phe Asn His
                 85                  90                  95

Leu Ala Ser Trp Leu Glu Asp Ala Arg Gln His Ala Asn Pro Asn Met
            100                 105                 110

Thr Ile Met Leu Ile Gly Asn Lys Ser Asp Leu Ser His Arg Arg Ala
        115                 120                 125

Val Thr Lys Glu Glu Gly Glu Gln Phe Ala Lys Glu Asn Gly Leu Leu
    130                 135                 140

Phe Leu Glu Ala Ser Ala Arg Thr Ala Gln Asn Val Glu Glu Ala Phe
145                 150                 155                 160

Val Lys Thr Ala Ala Gln Ile Leu Gln Asn Ile Gln Asp Gly Val Phe
                165                 170                 175

Asp Val Ser Asn Glu Thr Ser Gly Ile Lys Val Gly Tyr Gly Arg Pro
            180                 185                 190
```

```
Gln Gly Gln Ala Gly Ala Arg Asp Gly Ala Val Ala Gln Arg Gly Gly
        195                 200                 205

Cys Cys Ser
    210

<210> SEQ ID NO 36
<211> LENGTH: 216
<212> TYPE: PRT
<213> ORGANISM: Eucalyptus grandis

<400> SEQUENCE: 36

Met Val Asp Ser Phe Asp Glu Glu Cys Asp Tyr Leu Phe Lys Ala Val
  1               5                  10                  15

Leu Thr Gly Asp Ser Ala Val Gly Lys Ser Asn Leu Leu Ser Arg Phe
             20                  25                  30

Ala Arg Lys Glu Phe Gln Leu Asp Ser Lys Pro Thr Ile Gly Val Glu
         35                  40                  45

Phe Ala Tyr Arg Asn Val Lys Val Ala Asp Lys Leu Ile Lys Ala Gln
     50                  55                  60

Ile Trp Asp Thr Ala Gly Gln Glu Arg Phe Arg Ala Ile Thr Ser Ser
 65                  70                  75                  80

Tyr Tyr Arg Gly Ala Leu Gly Ala Leu Leu Val Tyr Asp Ile Thr Arg
                 85                  90                  95

Arg Val Thr Phe Glu Asn Val Lys Lys Trp Leu Arg Glu Leu Arg Asp
            100                 105                 110

Phe Gly Asn Pro Asp Met Val Val Leu Val Gly Asn Lys Ser Asp
        115                 120                 125

Leu Ser Asn Ser Arg Glu Val Asp Leu Glu Glu Gly Lys Asp Phe Ala
    130                 135                 140

Glu Ala Glu Asn Leu Cys Phe Met Glu Thr Ser Ala Leu Glu Asn Leu
145                 150                 155                 160

Asn Val Glu Glu Ala Phe Leu Glu Met Ile Thr Arg Ile His Glu Ile
                165                 170                 175

Thr Ser Gln Lys Ser Leu Glu Ala Lys Asn Asn Glu Ile Thr Ser Ser
            180                 185                 190

Leu His Gly Pro Lys Gln Val Ile Gln Ile Asp Glu Val Thr Ala Thr
        195                 200                 205

Lys Lys Ser Tyr Cys Cys Ser Ile
    210                 215

<210> SEQ ID NO 37
<211> LENGTH: 200
<212> TYPE: PRT
<213> ORGANISM: Pinus radiata

<400> SEQUENCE: 37

Met Ser Gly Pro Gly Ala Ile Arg Arg Lys Leu Val Ile Val Gly Asp
  1               5                  10                  15

Gly Ala Cys Gly Lys Thr Ser Leu Leu Cys Val Phe Ala Met Gly Glu
             20                  25                  30

Phe Pro Lys Glu Tyr Glu Pro Thr Ile Phe Glu Asn Tyr Val Ala Glu
         35                  40                  45

Ile Arg Leu Asp Gly Lys Pro Val Gln Leu Ala Leu Trp Asp Thr Ala
     50                  55                  60

Gly Gln Glu Glu Tyr Glu Arg Leu Arg Pro Leu Ser Tyr Ser Lys Ala
 65                  70                  75                  80
```

```
His Val Ile Leu Ile Ala Phe Ala Ile Asp Thr Pro Asp Ser Leu Glu
            85                  90                  95

Asn Val Ser Val Lys Trp Ile Glu Glu Val Arg Asn Ile Cys Gly Pro
            100                 105                 110

Gln Thr Pro Val Ile Leu Val Gly Cys Lys Ala Asp Leu Arg Pro Ala
            115                 120                 125

Ser Gly Ser Ser Ala Asp Gly Arg Gln Tyr Val Thr Arg Gln Arg Ala
            130                 135                 140

Gln Ala Val Ala Gln Glu Ile Gly Ala Arg Ala Tyr Lys Glu Cys Ser
145                 150                 155                 160

Ala Leu Asn Asn Gln Gly Val Asp Asp Val Phe Glu Ala Ala Thr Arg
                165                 170                 175

Ala Ser Met Ile Val Arg Glu Val Lys Pro Glu Ala Asp Glu Glu His
            180                 185                 190

Arg Gly Gly Cys Cys Val Leu Cys
            195                 200

<210> SEQ ID NO 38
<211> LENGTH: 412
<212> TYPE: PRT
<213> ORGANISM: Eucalyptus grandis

<400> SEQUENCE: 38

Met Ala Met Val Gln Arg Gln Gly His Asp Pro Ser Ser Pro Gln Glu
1               5                   10                  15

Gln Glu Asp Gly Pro Ser Ser Phe Leu Ser Asp Ala Leu Tyr Cys
            20                  25                  30

Glu Glu Gly Arg Phe Glu Glu Asp Gly Gly Gly Gly Gly Gln Val
            35                  40                  45

Asp Gly Ile Pro Leu Phe Pro Ser Gln Pro Ala Asp Arg Gln Gln Asp
    50                  55                  60

Ser Pro Trp Ala Asp Glu Asp Gly Glu Glu Lys Glu Glu Glu Glu Ala
65                  70                  75                  80

Glu Leu Gln Ser Leu Phe Ser Lys Glu Arg Gly Ala Arg Pro Glu Leu
                85                  90                  95

Ala Lys Asp Asp Gly Gly Ala Val Ala Ala Arg Arg Glu Ala Val Glu
            100                 105                 110

Trp Met Leu Met Val Arg Gly Val Tyr Gly Phe Ser Ala Leu Thr Ala
            115                 120                 125

Val Leu Ala Val Asp Tyr Leu Asp Arg Phe Leu Ala Gly Phe Arg Leu
            130                 135                 140

Gln Arg Asp Asn Arg Pro Trp Met Thr Gln Leu Val Ala Val Ala Cys
145                 150                 155                 160

Leu Ala Leu Ala Ala Lys Val Glu Glu Thr Asp Val Pro Leu Leu Val
                165                 170                 175

Glu Leu Gln Glu Val Gly Asp Ala Arg Tyr Val Phe Glu Ala Lys Thr
            180                 185                 190

Val Gln Arg Met Glu Leu Leu Val Leu Ser Thr Leu Gly Trp Glu Met
            195                 200                 205

His Pro Val Thr Pro Leu Ser Phe Val His Val Ala Arg Arg Leu
            210                 215                 220

Gly Ala Ser Pro His His Gly Glu Phe Thr His Trp Ala Phe Leu Arg
225                 230                 235                 240

Arg Cys Glu Arg Leu Leu Val Ala Ala Val Ser Asp Ala Arg Ser Leu
                245                 250                 255
```

```
Lys His Leu Pro Ser Val Leu Ala Ala Ala Met Leu Arg Val Ile
            260                 265                 270

Glu Glu Val Glu Pro Phe Arg Ser Ser Glu Tyr Lys Ala Gln Leu Leu
            275                 280                 285

Ser Ala Leu His Met Ser Gln Glu Met Val Glu Asp Cys Cys Arg Phe
            290                 295                 300

Ile Leu Gly Ile Ala Glu Thr Ala Gly Asp Ala Val Thr Ser Ser Leu
305                 310                 315                 320

Asp Ser Phe Leu Lys Arg Lys Arg Cys Gly His Leu Ser Pro Arg
                325                 330                 335

Ser Pro Ser Gly Val Ile Asp Ala Ser Phe Ser Cys Asp Asp Glu Ser
            340                 345                 350

Asn Asp Ser Trp Ala Thr Asp Pro Ser Asp Pro Asp Asn Asp
            355                 360                 365

Asp Leu Asn Pro Leu Pro Lys Lys Ser Arg Ser Ser Ser Pro Ser Ser
            370                 375                 380

Ser Pro Ser Ser Val Pro Asp Lys Val Leu Asp Leu Pro Phe Met Asn
385                 390                 395                 400

Arg Ile Phe Glu Gly Ile Val Asn Gly Ser Pro Ile
                405                 410

<210> SEQ ID NO 39
<211> LENGTH: 331
<212> TYPE: PRT
<213> ORGANISM: Cucurbita maxima

<400> SEQUENCE: 39

Met Ser Val Ser Ile Ser Asn Cys Phe Ser Asp Leu Leu Cys Gln Glu
1               5                   10                  15

Asp Ser Ser Gly Val Leu Ser Gly Glu Ser Leu Gly Cys Ser Ser Asp
            20                  25                  30

Leu Asp Ser Pro Ala Cys Val Glu Glu Ser Ile Ala Val Phe Ile Lys
        35                  40                  45

Asp Glu Arg His Phe Val Pro Asp Tyr Asp Cys Leu Ser Arg Phe Gln
    50                  55                  60

Ser Pro Ser Leu Asp Ala Ala Ala Arg Leu Asp Ser Val Ala Trp Ile
65                  70                  75                  80

Leu Lys Val Gln Ala Tyr Tyr Gly Phe Gln Pro Leu Thr Ala Tyr Leu
                85                  90                  95

Ser Val Asn Tyr Leu Asp Arg Phe Leu Cys Ser Arg Arg Leu Pro Gln
            100                 105                 110

Thr Asn Gly Trp Pro Leu Gln Leu Leu Ser Val Ala Cys Leu Ser Leu
        115                 120                 125

Ala Ala Lys Met Glu Glu Pro Leu Val Pro Ala Leu Leu Asp Leu Gln
    130                 135                 140

Val Glu Gly Ala Lys Tyr Ile Phe Glu Pro Arg Thr Ile Cys Arg Met
145                 150                 155                 160

Glu Leu Leu Val Leu Arg Val Leu Asp Trp Arg Leu Arg Ser Val Thr
                165                 170                 175

Pro Phe Asn Phe Ile Ala Phe Ala Cys Lys Leu Asp Pro Ser Gly
            180                 185                 190

Asp Phe Met Gly Phe Leu Ile Ser Arg Ala Thr Glu Ile Ile Ile Ser
        195                 200                 205

Asn Ile Arg Glu Val Ile Phe Leu Glu Tyr Trp Pro Ser Cys Ile Ala
```

```
               210                 215                 220
Ala Ala Ala Leu Leu Cys Ala Ala Asn Glu Val Pro Asn Leu Ser Val
225                 230                 235                 240

Val Asn Pro Glu His Ala Glu Ser Trp Cys Ser Gly Leu Arg Lys Glu
                245                 250                 255

Asn Ile Ile Gly Cys Tyr Arg Leu Met Gln Glu Ile Val Leu Asp Ser
                260                 265                 270

Cys Arg Ile Glu Ser Pro Lys Ile Leu Pro Gln Phe Arg Val Thr Val
                275                 280                 285

Arg Thr Arg Met Arg Ser Ser Asp Leu Ser Pro Tyr Ser Ser Ser Ser
290                 295                 300

Ser Ser Ser Ser Pro Asn Lys Arg Lys Leu Asn Gln Ser Leu
305                 310                 315                 320

Trp Val Asp Asp Lys Asp Asn Pro Glu Glu
                325                 330

<210> SEQ ID NO 40
<211> LENGTH: 336
<212> TYPE: PRT
<213> ORGANISM: Cucurbita maxima

<400> SEQUENCE: 40

Met Ser Ile Ser Ser Glu Asp Cys Phe Ile Asp Ser His Leu Leu
 1               5                  10                  15

Cys Asp Glu Asp Ser Ser Asp Ile Leu Ser Gly Glu Ser Pro Glu Tyr
                20                  25                  30

Ser Ser Asp Leu Glu Ser Pro Ala Ser Ser Glu Asp Ser Ile Ala Ser
                35                  40                  45

Phe Ile Glu Asp Glu Arg His Phe Val Pro Gly Ile Asp Tyr Leu Ser
50                  55                  60

Arg Phe His Ser Gln Ser Leu Asp Ser Ser Ala Arg Ala Asp Ser Val
65                  70                  75                  80

Ala Trp Ile Leu Lys Val Gln Ala Tyr Tyr Gly Phe Gln Pro Leu Thr
                85                  90                  95

Ala Tyr Leu Ser Val Asn Tyr Leu Asp Arg Phe Leu Tyr Ser Arg Arg
                100                 105                 110

Leu Pro Glu Thr Asn Gly Trp Pro Leu Gln Leu Leu Ser Val Ala Cys
                115                 120                 125

Leu Ser Leu Ala Ala Lys Met Glu Glu Pro Leu Val Pro Ser Phe Leu
130                 135                 140

Asp Leu Gln Ile Glu Gly Ala Lys Tyr Ile Phe Glu Pro Arg Thr Ile
145                 150                 155                 160

Arg Arg Met Glu Leu Leu Val Leu Ala Thr Leu Asp Trp Arg Leu Arg
                165                 170                 175

Ser Val Thr Pro Phe Ser Phe Ile Gly Phe Ala Tyr Lys Val Asp
                180                 185                 190

Pro Thr Gly Thr Phe Ser Ser Phe Leu Ile Ser Arg Ser Thr Glu Ile
                195                 200                 205

Ile Leu Ser Asn Ile Arg Asp Ala Ser Phe Leu Glu Tyr Trp Pro Ser
                210                 215                 220

Cys Ile Ala Ala Ala Leu Leu Cys Ala Ala Asn Glu Ile Pro Asn
225                 230                 235                 240

Leu Thr Leu Leu Asn Pro Glu His Ala Glu Ser Trp Cys Asn Gly Leu
                245                 250                 255
```

```
Ser Lys Asp Lys Ile Val Gly Cys Tyr Arg Leu Met Gln Pro Ser Thr
        260                 265                 270

Ser Glu Ser Gly Arg Arg Lys Pro Lys Val Ile Pro Gln Leu Arg
        275                 280                 285

Val Arg Ile Arg Ala Gly Leu Arg Tyr Ser Asn Ser Ser Ser Ser
        290                 295                 300

Ser Ser Thr Arg Leu Gly Tyr Lys Arg Lys Leu Asn Asn Cys Leu
305                 310                 315                 320

Trp Val Glu Glu Asp Lys Glu Asn Ser Lys Phe Arg Ala Glu Glu
                325                 330                 335
```

<210> SEQ ID NO 41
<211> LENGTH: 335
<212> TYPE: PRT
<213> ORGANISM: Cucumis sativus

<400> SEQUENCE: 41

```
Met Ser Val Ser Ile Ser Asn Cys Phe Ser Asn Leu Leu Cys Gln Glu
 1               5                  10                  15

Asp Ser Ser Gly Val Phe Ser Gly Glu Ser Pro Gly Cys Ser Ser Asp
                20                  25                  30

Leu Glu Ser Pro Ala Cys Val Glu Glu Ser Ile Ser Val Phe Ile Lys
            35                  40                  45

Asn Glu Arg His Phe Val Pro Asp Tyr Asp Cys Phe Ser Arg Phe Gln
     50                  55                  60

Ser Pro Ser Leu Asp Ala Ala Arg Leu Asp Ser Ile Ala Trp Ile
 65                  70                  75                  80

Leu Lys Val Gln Ala Tyr Tyr Gly Phe Gln Pro Leu Thr Ala Tyr Leu
                    85                  90                  95

Ser Val Asn Tyr Leu Asp Arg Phe Leu Cys Ser Arg Arg Leu Pro Gln
                100                 105                 110

Ser Asn Gly Trp Pro Leu Gln Leu Leu Ser Val Ala Cys Leu Ser Leu
            115                 120                 125

Ala Ala Lys Met Glu Glu Pro Leu Val Pro Ala Leu Leu Asp Leu Gln
130                 135                 140

Val Glu Gly Ala Lys Tyr Ile Phe Glu Pro Arg Thr Ile Cys Arg Met
145                 150                 155                 160

Glu Leu Leu Val Leu Arg Val Leu Asp Trp Arg Leu Arg Ser Val Thr
                    165                 170                 175

Pro Phe Asn Phe Ile Ala Phe Phe Ala Tyr Lys Leu Asp Pro Ser Gly
                180                 185                 190

Asp Phe Ile Glu Phe Leu Ile Ser Arg Ala Thr Glu Ile Ile Leu Ser
            195                 200                 205

His Ile Arg Glu Val Ile Phe Leu Glu Tyr Trp Pro Ser Cys Ile Ala
     210                 215                 220

Ala Ala Ala Leu Leu Cys Ala Ala Asn Glu Val Gln Ser Leu Ser Val
225                 230                 235                 240

Val Asn Pro Glu His Ala Glu Ser Trp Cys Asn Gly Leu Arg Lys Glu
                    245                 250                 255

Asn Ile Met Gly Cys Tyr Arg Leu Met Gln Glu Ile Val Leu Asp Asn
                260                 265                 270

Thr Arg Arg Lys Ser Pro Lys Ile Leu Pro Gln Tyr Arg Val Thr Val
            275                 280                 285

Arg Thr Arg Met Arg Ser Ser Asp Leu Ser Ser Ser Tyr Ser Ser Ser
        290                 295                 300
```

Ser Ser Ser Ser Ser Ser Pro Asn Lys Arg Arg Lys Leu Asn Gln
305                 310                 315                 320

Thr His Leu Trp Val His Glu Asp Lys Gly Asn Asn Thr Glu Glu
            325                 330                 335

<210> SEQ ID NO 42
<211> LENGTH: 347
<212> TYPE: PRT
<213> ORGANISM: Cucurbita maxima

<400> SEQUENCE: 42

Met Ala Pro Ser Phe Asp Leu Ala Val Thr Asn Leu Leu Cys Ala Glu
1               5                   10                  15

Glu Asn Cys Ile Phe Asp Asp Asn Asp Asp Glu Cys Leu Val Ala
                20                  25                  30

Pro Tyr Val Leu Thr Ser Asn Gly Phe Gln Ser Trp Arg His Gly Gly
            35                  40                  45

Gly His Gly Gly Asp Gly Leu Pro Phe Thr Ser Asp Glu Cys Leu Ile
    50                  55                  60

Glu Met Val Glu Lys Glu Thr His His Leu Pro Val Asp Gly Tyr Leu
65                  70                  75                  80

Met Lys Leu Gln Asn Gly Glu Leu Asp Val Gly Ala Arg Lys Asp Ala
                85                  90                  95

Val Asp Trp Ile Glu Gln Val Ser Ala Arg Phe Asn Phe Gly Pro Leu
            100                 105                 110

Cys Thr Tyr Leu Ala Val Asn Tyr Met Asp Arg Phe Leu Ser Ala Tyr
        115                 120                 125

Thr Leu Pro Lys Gly Lys Ala Trp Thr Met Gln Leu Leu Ala Val Ala
    130                 135                 140

Cys Leu Ser Leu Ala Ala Lys Leu Glu Glu Thr Glu Val Pro Ile Ser
145                 150                 155                 160

Leu Asp Leu Gln Val Gly Gly Ser Lys Phe Val Phe Glu Ala Arg Thr
                165                 170                 175

Ile Glu Arg Met Glu Leu Leu Val Leu Thr Thr Leu Gly Trp Arg Met
            180                 185                 190

Gln Ala Val Thr Pro Phe Ser Phe Ile Asp His Tyr Leu Cys Lys Ile
        195                 200                 205

His His Asp Asp Lys Thr Ser Ile Ala Arg Ser Ile His Leu Leu Leu
    210                 215                 220

Asn Ile Ile Gln Gly Ile Glu Phe Leu Glu Phe Lys Pro Ser Glu Ile
225                 230                 235                 240

Ala Ala Ala Val Ala Ile Ser Val Ala Gly Glu Gly Glu Thr Ala
                245                 250                 255

Ile Pro Leu Leu Ile Gln Gln Lys Leu His Met Glu Arg Val Val Lys
            260                 265                 270

Cys Ile Lys Leu Val Lys Glu Met Ser Gly Lys Thr Glu Glu Glu
        275                 280                 285

Ser Arg Ser Met Ser Glu Gly Pro Gln Ser Pro Ser Gly Val Leu Asn
    290                 295                 300

Val Arg Cys Leu Ser Tyr Lys Ser Asn Glu Ser Thr Ala Val Gly Ser
305                 310                 315                 320

Cys Ala Asn Ser Ser Ser His His Asn Ser Ser Asn Gly Ser Lys Arg
                325                 330                 335

Arg Arg Leu Asn Arg Pro Cys Glu Val Glu Leu

<210> SEQ ID NO 43
<211> LENGTH: 338
<212> TYPE: PRT
<213> ORGANISM: Cucurbita maxima

<400> SEQUENCE: 43

```
Met Ala Leu Pro Asp Asp Glu Ala Gln Val Gln Glu Ile Glu Thr Gln
  1               5                  10                  15

Ser Tyr Val Leu Asp Ala Leu Phe Cys Glu Asp Leu Cys Cys Asp Glu
             20                  25                  30

Asp Phe Asp Gly Asn Gly Thr Val Glu Asp Ser Asp Tyr Trp Glu Thr
         35                  40                  45

Leu Arg Lys Asp Gln Pro Phe Leu Ala Ile Asn Leu Leu Glu Lys Asp
     50                  55                  60

Pro Leu Trp Glu Asp Asp Glu Glu Leu Gln Ser Leu Ile Ser Lys Glu
 65                  70                  75                  80

Glu Gln Thr His Val Cys Asn Ala Ser Val Thr Ser Asp Gly Tyr Leu
                 85                  90                  95

Ile Gln Ala Arg Asn Glu Ala Leu Ser Trp Ile Phe Ser Val Lys His
            100                 105                 110

Tyr Tyr Ala Phe Ser Ala Phe Thr Ser Leu Leu Ala Val Asn Tyr Phe
        115                 120                 125

Asp Arg Phe Val Ser Asn Val Arg Phe Gln Arg Asp Lys Pro Trp Met
    130                 135                 140

Ser Gln Leu Ala Ala Val Ala Cys Leu Ser Leu Ala Ala Lys Val Glu
145                 150                 155                 160

Glu Thr Gln Val Pro Leu Leu Leu Asp Leu Gln Val Val Glu Ser Lys
                165                 170                 175

Phe Leu Phe Glu Ala Lys Thr Ile Gln Arg Met Glu Leu Leu Val Leu
            180                 185                 190

Ser Ala Leu Gln Trp Lys Met His Pro Val Thr Pro Phe Ser Phe Leu
        195                 200                 205

Arg His Ile Ile Arg Arg Leu Pro Leu Lys Asp His Met Leu Trp Glu
    210                 215                 220

Leu Leu Gly Arg Phe Gln Ser His Leu Leu Ser Ile Ile Ala Asp His
225                 230                 235                 240

Arg Phe Leu Cys Tyr Leu Pro Ser Val Leu Ala Thr Ala Thr Ile Leu
                245                 250                 255

His Ile Ile Asn Glu Ile Glu Pro Cys Asn Phe Leu Glu Tyr Gln Asn
            260                 265                 270

Glu Leu Leu Ser Val Leu Lys Ile Asn Lys Asn His Leu Asp Glu Cys
        275                 280                 285

Tyr Lys Val Ile Leu Asp Ser Leu Gly Ser Asn Gly Ser Val Asn Ser
    290                 295                 300

Tyr Gln Met Cys Gly Leu Gly Ser Pro Arg Asp Val Met Asp Gly Tyr
305                 310                 315                 320

Phe Ile Ser Asp Ser Ser Asn Asp Ser Trp Pro Met Val Pro Ser Ile
                325                 330                 335

Ser Pro
```

<210> SEQ ID NO 44
<211> LENGTH: 380
<212> TYPE: PRT

<213> ORGANISM: Cucurbita maxima

<400> SEQUENCE: 44

| | | | | | | | | | | | | | | |
|---|---|---|---|---|---|---|---|---|---|---|---|---|---|---|
| Met | Ala | Met | His | Arg | Tyr | Glu | Pro | Ala | Asp | Asp | Glu | Ala | Gln | Thr | His |
| 1 | | | | 5 | | | | | 10 | | | | | 15 | |
| Leu | Ile | Ser | Leu | Asp | Ser | Leu | Phe | Cys | Glu | Glu | Lys | Trp | Glu | Glu |
| | | | 20 | | | | | 25 | | | | | 30 | |
| Glu | Glu | Glu | Asp | Glu | Asp | Glu | Leu | Glu | Gln | Thr | His | Gln | Ala | His | Val |
| | | 35 | | | | | 40 | | | | | 45 | | | |
| Phe | Ser | Leu | Asp | Val | Leu | Glu | Glu | Asp | Leu | Phe | Gly | Glu | Asp | Glu | Arg |
| | 50 | | | | | 55 | | | | | 60 | | | | |
| Leu | Leu | Ser | Leu | Leu | Ser | Lys | Glu | Thr | Glu | Gln | Leu | Lys | Gln | Ser | Asn |
| 65 | | | | | 70 | | | | | 75 | | | | | 80 |
| Leu | Lys | Leu | Glu | Pro | Leu | Leu | Met | Asp | Pro | Ser | Val | Ser | Ala | Ala | Arg |
| | | | | 85 | | | | | 90 | | | | | 95 | |
| Ser | Ser | Ser | Val | Glu | Trp | Met | Leu | Lys | Val | Lys | Ser | His | Tyr | Gly | Phe |
| | | | 100 | | | | | 105 | | | | | 110 | | |
| Ser | Ser | Leu | Thr | Ala | Ile | Leu | Ala | Val | Ala | Tyr | Phe | Asp | Arg | Phe | Leu |
| | | 115 | | | | | 120 | | | | | 125 | | | |
| Ser | Ser | Phe | His | Phe | Arg | Ser | Asp | Lys | Pro | Trp | Met | Asn | Gln | Leu | Val |
| | 130 | | | | | 135 | | | | | 140 | | | | |
| Ala | Val | Thr | Cys | Leu | Ser | Leu | Ala | Ala | Lys | Val | Glu | Glu | Val | Glu | Val |
| 145 | | | | | 150 | | | | | 155 | | | | | 160 |
| Pro | Leu | Leu | Leu | Asp | Leu | Gln | Val | Glu | Asp | Ala | Lys | Phe | Val | Phe | Glu |
| | | | | 165 | | | | | 170 | | | | | 175 | |
| Ala | Lys | Thr | Ile | Gln | Arg | Met | Glu | Leu | Leu | Val | Leu | Ser | Thr | Leu | Gln |
| | | | 180 | | | | | 185 | | | | | 190 | | |
| Trp | Arg | Met | His | Leu | Val | Thr | Ser | Tyr | Ser | Tyr | Leu | Asp | Asn | Ile | Val |
| | | 195 | | | | | 200 | | | | | 205 | | | |
| Arg | Arg | Leu | Gly | Leu | Lys | Thr | Asn | Leu | His | Leu | Glu | Phe | Phe | Lys | Arg |
| | 210 | | | | | 215 | | | | | 220 | | | | |
| Ser | Glu | Asn | Leu | Leu | Leu | Ser | Leu | Leu | Ser | Asp | Ser | Arg | Phe | Val | Gly |
| 225 | | | | | 230 | | | | | 235 | | | | | 240 |
| Tyr | Leu | Pro | Ser | Val | Leu | Ala | Ser | Ala | Thr | Met | Met | Asn | Ile | Ile | Glu |
| | | | | 245 | | | | | 250 | | | | | 255 | |
| Gln | Ile | Glu | Pro | His | Lys | Ser | Met | Glu | His | Gln | Asp | His | Leu | Leu | Gly |
| | | | 260 | | | | | 265 | | | | | 270 | | |
| Val | Leu | Lys | Met | Ser | Lys | Asp | Lys | Val | Leu | Gly | Cys | Tyr | Asn | Leu | Val |
| | | 275 | | | | | 280 | | | | | 285 | | | |
| Val | Glu | His | Ser | Lys | Ala | Cys | Ser | Asn | Gly | Leu | Tyr | His | Ser | Asn | Asn |
| | 290 | | | | | 295 | | | | | 300 | | | | |
| Pro | His | Lys | Arg | Lys | Tyr | Glu | His | His | Gln | Ala | Pro | Asp | Ser | Pro | Asn |
| 305 | | | | | 310 | | | | | 315 | | | | | 320 |
| Gly | Val | Ile | Asp | Ala | Gly | Phe | Ser | Ser | Asp | Ser | Ser | Asn | Asp | Ser | Trp |
| | | | | 325 | | | | | 330 | | | | | 335 | |
| Ala | Leu | Arg | Ala | Ala | Ala | Ser | Val | Cys | Ser | Ser | Pro | Glu | Pro | Ser | Phe |
| | | | 340 | | | | | 345 | | | | | 350 | | |
| Lys | Lys | Asn | Lys | Thr | Glu | Glu | Pro | Arg | Met | Leu | Tyr | His | Ser | Leu | Asn |
| | | 355 | | | | | 360 | | | | | 365 | | | |
| Arg | Arg | Val | Cys | Leu | Asp | Ile | Val | Gly | Ser | Pro | Ser |
| | 370 | | | | | 375 | | | | | 380 |

<210> SEQ ID NO 45
<211> LENGTH: 385

```
<212> TYPE: PRT
<213> ORGANISM: Sicyos angulatus

<400> SEQUENCE: 45

Met Ala Met His Arg Phe Glu Gln Ser Asp His Glu Ala Gln Thr His
 1               5                  10                  15

Leu Ile Ser Leu Asp Ser Leu Tyr Cys Glu Glu Lys Trp Glu Asp
            20                  25                  30

Gly Glu Asp Gly Val Asp Glu Ile Glu Gln Ala His Glu Ile Asn
            35                  40                  45

Gln Thr His Leu Phe Ser Leu Gly Phe Glu Glu Asn Leu Phe Glu
 50                  55                  60

Glu Asp Glu Arg Leu Arg Ser Leu Leu Ser Lys Glu Thr Gln Leu
65                  70                  75                  80

Glu Gln Ser Asn Leu Asp Leu Glu Ala Leu Leu Met Asp Pro Ser Val
                85                  90                  95

Ser Ala Ala Arg Ser Ser Ala Val Glu Trp Met Leu Lys Val Lys Ser
               100                 105                 110

His Tyr Gly Phe Ser Thr Leu Thr Ala Ile Met Ala Val Ser Tyr Phe
               115                 120                 125

Asp Arg Phe Leu Leu Ser Phe His Tyr Lys Ser Asp Lys Pro Trp Met
130                 135                 140

Asn Gln Leu Val Ala Val Thr Cys Leu Ser Leu Ala Ala Lys Val Glu
145                 150                 155                 160

Glu Ile His Val Pro Leu Leu Leu Asp Leu Gln Val Glu Asp Ala Glu
                165                 170                 175

Tyr Val Phe Glu Ala Lys Thr Ile Gln Arg Met Glu Leu Leu Val Leu
                180                 185                 190

Ser Thr Leu Gln Trp Arg Met His Phe Val Thr Pro Phe Ser Phe Leu
                195                 200                 205

Asp His Ile Val Lys Arg Leu Gly Phe Lys Ala Asn Leu Gln Leu Glu
                210                 215                 220

Phe Leu Arg Cys Ser Glu His Leu Leu Leu Ser Met Leu Ser Asp Ser
225                 230                 235                 240

Arg Phe Val Gly Tyr Leu Pro Ser Val Leu Ala Thr Ala Thr Met Met
                245                 250                 255

Lys Val Ile Asp His Ile Glu Pro His Glu Ser Leu Glu His Gln Asp
                260                 265                 270

Gln Leu Leu Gly Val Leu Lys Met Ser Lys Glu Lys Val Gln Cys Cys
                275                 280                 285

Tyr Asn Leu Val Val Glu His Ser Lys Ala Tyr Gly Asn Asn Gly Phe
                290                 295                 300

Tyr His Leu Asn Asn Pro Tyr Lys Arg Lys His Glu His His Gln
305                 310                 315                 320

Ala Pro Tyr Ser Pro Ser Gly Val Ile Asp Ala Gly Phe Ser Ser Asp
                325                 330                 335

Ser Ser Asn Asp Ser Trp Ala Leu Arg Ala Ser Ser Ser Val Cys Ser
                340                 345                 350

Ser Pro Glu Ser Ser Phe Lys Lys Thr Lys Thr Glu Glu Pro Asn Leu
                355                 360                 365

Lys Phe His Pro Leu Asn Arg Val Phe Leu Asp Ile Val Gly Ser Pro
                370                 375                 380

Ser
385
```

<210> SEQ ID NO 46
<211> LENGTH: 779
<212> TYPE: DNA
<213> ORGANISM: Eucalyptus grandis

<400> SEQUENCE: 46

```
ccgcactcga acttcaacgc agcgagggga gcagaacgag gtcgccgtcg tctccagcct      60
ctgccaaaat agagtccgcc gatcgcaaga ggaagagacc gtcgtcctca acgatctcgt     120
cggccgatcc atccgccgcc aagtccggca gcctcaggga caagcacagg gcgaaggcca     180
agatgtcgtc gtcggcggcg ggggcggcgg cggcggggag ccaggtccgc gcgtcgcaca     240
tcctcatcaa gcacgagggc tcccggagga aggcctcgtg gaaggatccg gagggcaggg     300
tcatccgcag caccacccgc gagagcgccg tctcgcagct caaggccctc agggaggaca     360
tcgtcgccgg caaggccaag ttcgaggacc tcgcctcgcg cttctccgac tgcagctccg     420
ccaagcgcgg cggtgatctc ggtccctttg ggcgaggcca gatgcagaaa cctttcgagg     480
aagcgactta tgctctcaag gttggcgaga ttagcgacat cgtcgatacc gacagtgggg     540
tccacatcat aatgaggact ggctaaaaca tagttggagt gcagagaaga tcaagaatac     600
gatcaatgct ttgcttggga ttctggttat atggtgtttg actattcgga ctacgttgcc     660
ttgatttacc ggttccgtgc ctcctctatg tcattgcaat gcataaatt  gtttcgagga     720
aacattcacc tgtcaaaaac ctttggatgc ttgttgggat atttctcgca aaaaaaaaa     779
```

<210> SEQ ID NO 47
<211> LENGTH: 403
<212> TYPE: DNA
<213> ORGANISM: Pinus radiata

<400> SEQUENCE: 47

```
ccggaggcgt aacatcgttc gccgcctgac aattattcac tcaaggcacg atcatggcaa      60
aaacagcagc agcactgcat atccttgtaa agaagagaa  actggctctg gatcttctcg     120
agcagattaa gaacggggcc gatttcggca agctggcgaa gaaacactcc atttgcccat     180
caggcaaacg cggcggtgat ttaggtgaat ccgccaggg  tcagatggtt ccggcgttcg     240
ataaagtggt tttctcttgt ccggtactgg agccgaccgg cccgctgcac acccagttcg     300
gatatcacat cattaaggtg ctgtaccgca actaatagca aggccttctc caggagaagg     360
ccttgagtgt tttctccctc tccctgtggg agagggtcgg ggt                        403
```

<210> SEQ ID NO 48
<211> LENGTH: 123
<212> TYPE: PRT
<213> ORGANISM: Eucalyptus grandis

<400> SEQUENCE: 48

```
Met Glu Lys Lys Met Ala Ser Ser Gln Lys Val Arg Ala Ser His Leu
 1               5                  10                  15

Leu Ile Lys His Glu Gly Ser Arg Arg Pro Ser Ser Trp Gln Asp Pro
            20                  25                  30

Asp Gly Arg Arg Ile Lys Ala Thr Thr Arg Asp Ala Ala Val Ala Gln
        35                  40                  45

Leu Ser Ala Leu Arg Glu Glu Ile Val Ser Gly Arg Ala Lys Phe Glu
    50                  55                  60

Asp Leu Ala Ala Arg Tyr Ser Asp Cys Lys Ser Ala Lys Lys Gly Gly
65                  70                  75                  80
```

```
Asp Leu Gly Pro Phe Gly Arg Gly Gln Met Gln Lys Pro Phe Glu Asp
                85                  90                  95

Ala Thr Tyr Leu Leu Lys Val Gly Glu Ile Ser Asp Ile Val Asp Thr
            100                 105                 110

Asp Ser Gly Val His Ile Ile Leu Arg Thr Gly
        115                 120
```

<210> SEQ ID NO 49
<211> LENGTH: 93
<212> TYPE: PRT
<213> ORGANISM: Pinus radiata

<400> SEQUENCE: 49

```
Met Ala Lys Thr Ala Ala Leu His Ile Leu Val Lys Glu Glu Lys
1               5                   10                  15

Leu Ala Leu Asp Leu Leu Glu Gln Ile Lys Asn Gly Ala Asp Phe Gly
            20                  25                  30

Lys Leu Ala Lys Lys His Ser Ile Cys Pro Ser Gly Lys Arg Gly Gly
        35                  40                  45

Asp Leu Gly Glu Phe Arg Gln Gly Gln Met Val Pro Ala Phe Asp Lys
    50                  55                  60

Val Val Phe Ser Cys Pro Val Leu Glu Pro Thr Gly Pro Leu His Thr
65                  70                  75                  80

Gln Phe Gly Tyr His Ile Ile Lys Val Leu Tyr Arg Asn
                85                  90
```

<210> SEQ ID NO 50
<211> LENGTH: 119
<212> TYPE: PRT
<213> ORGANISM: Arabidopsis thaliana

<400> SEQUENCE: 50

```
Met Ala Ser Arg Asp Gln Val Lys Ala Ser His Ile Leu Ile Lys His
1               5                   10                  15

Gln Gly Ser Arg Arg Lys Ala Ser Trp Lys Asp Pro Glu Gly Lys Ile
            20                  25                  30

Ile Leu Thr Thr Thr Arg Glu Ala Ala Val Glu Gln Leu Lys Ser Ile
            35                  40                  45

Arg Glu Asp Ile Val Ser Gly Lys Ala Asn Phe Glu Glu Val Ala Thr
    50                  55                  60

Arg Val Ser Asp Cys Ser Ser Ala Lys Arg Gly Gly Asp Leu Gly Ser
65                  70                  75                  80

Phe Gly Arg Gly Gln Met Gln Lys Pro Phe Glu Glu Ala Thr Tyr Ala
                85                  90                  95

Leu Lys Val Gly Asp Ile Ser Asp Ile Val Asp Thr Asp Ser Gly Val
            100                 105                 110

His Ile Ile Lys Arg Thr Ala
        115
```

<210> SEQ ID NO 51
<211> LENGTH: 127
<212> TYPE: PRT
<213> ORGANISM: Lycopersicon esculentum

<400> SEQUENCE: 51

```
Met Pro Ser Ser Ser Arg Tyr Gly Ala Gly Gly Asp Lys Val Lys
1               5                   10                  15
```

```
Ala Ser His Ile Leu Ile Lys His Gln Glu Ser Arg Arg Lys Phe Ser
            20                  25                  30

Trp Lys Asp Pro Glu Gly Arg Val Ile Ser Asn Thr Thr Lys Glu Ala
        35                  40                  45

Ala Val Ser Gln Leu Lys Ser Ile Arg Glu Asp Ile Val Ser Gly Lys
    50                  55                  60

Ala Lys Phe Gln Asp Ile Ala Ala Thr His Ser His Cys Ser Ser Ala
65                  70                  75                  80

Lys Arg Gly Gly Asp Leu Gly Ser Phe Gly Lys Gly Gln Met Gln Lys
                85                  90                  95

Pro Phe Glu Glu Ala Thr Phe Ala Leu Lys Val Gly Glu Ile Ser Asp
            100                 105                 110

Ile Val Glu Thr Glu Ser Gly Val His Ile Ile Leu Arg Thr Ala
            115                 120                 125

<210> SEQ ID NO 52
<211> LENGTH: 121
<212> TYPE: PRT
<213> ORGANISM: Malus domestica

<400> SEQUENCE: 52

Met Ser Ser Ser Ala Gly Asn Gln Val Arg Ala Ser His Ile Leu Ile
1               5                   10                  15

Lys His Gln Gly Ser Arg Arg Lys Ala Ser Trp Lys Asp Pro Glu Gly
            20                  25                  30

Gln Ile Ile Arg Asn Thr Thr Arg Asp Ser Ala Val Ser Gln Leu Lys
        35                  40                  45

Ala Leu Arg Asp Asp Ile Leu Ser Gly Lys Ala Lys Phe Asp Asp Leu
    50                  55                  60

Ala Ala Arg Tyr Ser Asp Cys Ser Ser Ala Lys Arg Gly Gly Asp Leu
65                  70                  75                  80

Gly Pro Phe Gly Arg Asn Gln Met Gln Lys Pro Phe Glu Glu Ala Thr
                85                  90                  95

Phe Ala Leu Lys Val Gly Glu Met Ser Asp Ile Val Asp Thr Asp Ser
            100                 105                 110

Gly Val His Ile Ile Lys Arg Thr Gly
            115                 120

<210> SEQ ID NO 53
<211> LENGTH: 118
<212> TYPE: PRT
<213> ORGANISM: Lycopersicon esculentum

<400> SEQUENCE: 53

Met Ala Ser Asn Gln Val Arg Ala Ser His Ile Leu Ile Lys His Glu
1               5                   10                  15

Gly Ser Arg Arg Lys Ser Ser Trp Lys Asp Pro Glu Gly Arg Ile Ile
            20                  25                  30

Cys Asn Thr Thr Arg Asp Ala Ala Ala Ser Gln Leu Lys Ser Phe Arg
        35                  40                  45

Asp Asp Ile Ile Ser Gly Lys Ser Lys Phe Glu Asp Val Ala Ser Arg
    50                  55                  60

Phe Ser Asp Cys Ser Ser Ala Lys Arg Gly Gly Asp Leu Gly Pro Phe
65                  70                  75                  80

Gly Arg Gly Gln Met Gln Lys Pro Phe Glu Val Ala Thr Tyr Ala Leu
                85                  90                  95
```

```
Glu Val Gly Glu Ile Ser Asp Ile Ile Asp Thr Asp Ser Gly Ala His
            100                 105                 110

Ile Ile Leu Arg Thr Gly
        115

<210> SEQ ID NO 54
<211> LENGTH: 118
<212> TYPE: PRT
<213> ORGANISM: Digitalis lanata

<400> SEQUENCE: 54

Met Ser Ser Glu Lys Val Arg Ala Ser His Ile Leu Ile Lys His Gln
  1               5                  10                  15

Gly Ser Arg Arg Lys Ser Ser Trp Lys Asp Pro Asp Gly Ser Leu Ile
             20                  25                  30

Ser Ala Thr Thr Arg Asp Asp Ala Val Ser Gln Leu Gln Ser Leu Arg
         35                  40                  45

Gln Glu Leu Leu Ser Asp Pro Ala Ser Phe Ser Asp Leu Ala Ser Arg
     50                  55                  60

His Ser His Cys Ser Ser Ala Lys Arg Gly Gly Asp Leu Gly Pro Phe
 65                  70                  75                  80

Gly Arg Gly Gln Met Gln Lys Pro Phe Glu Glu Ala Thr Phe Ala Leu
                 85                  90                  95

Lys Val Gly Glu Ile Ser Asp Ile Val Asp Thr Asp Ser Gly Val His
            100                 105                 110

Ile Ile Lys Arg Thr Gly
        115

<210> SEQ ID NO 55
<211> LENGTH: 648
<212> TYPE: DNA
<213> ORGANISM: Lycopersicon esculentum

<400> SEQUENCE: 55
cagagaaacc ccaagtactc tgcaattctc agcttccacc tttgcaaagt cgtatatcaa      60
atctgtaaaa atagagtcgg atcggaagag gaagaagaca tcgatctctg ctgcagatcg     120
accgccggat aagcacaaga aaaagtccaa aatgccgtca tcctcttccc gctacggcgc     180
cggtggagac aaagtgaagg cgtctcatat actcattaag catcaggagt ctcgtcgcaa     240
gttttcctgg aaggatccgg aaggtcgtgt tatctccaac accaccaaag aagctgccgt     300
ttctcagctg aaatctatcc gtgaagacat tgtctctggc aaagccaagt ccaggatat      360 agccgccact cattctcact gcagctcagc caaacgcggc ggtgatctcg gttcatttgg     420
caaaggtcag atgcagaaac cttttgaaga agcaactttt gctctaaaag ttggcgagat     480
aagtgacatc gtggaaactg agagtggtgt tcatatcatc ttgagaacgg cataatgtga     540
tgcttgcgga agaatgattg gaatactcac ccagaaaata ctcatattaa agatcacac      600 ccaggatatt ttttcttacg cccttctatt ccctgtgggt gtggtgaa                  648

<210> SEQ ID NO 56
<211> LENGTH: 879
<212> TYPE: DNA
<213> ORGANISM: Malus domestica

<400> SEQUENCE: 56
acgttgtagt cgcctccctc tctgtctctc agtttctcac ctcgcatctt tatctcttct      60
tcatctgcca tcccttccc cacagcccga tccccgctc tcaggctttt cactacatcc       120
```

```
gccgttggat tgcttcgttg caggtctgtc gactacaggc aagcaaacat tatcaaaact      180
ctgtgtttga gctgcaaaga tagattcgtc cgggcataag cgtaagaaag cagctccttt      240
gatctgtgca tcagatcaca cggacaagga caaagaaaaa aggcaggctg ctcgaaagac      300
caaaaggaca aaaatgtcct cgtcagcggg gaatcaggtg agggcgtccc atatactcat      360
caagcatcag gggtcgagaa gaaaggcatc gtggaaggat cctgaagggc agatcatcag      420
gaacaccacc cgagactctg ccgtctctca actcaaggct ctccgcgatg acatcctttc      480
tggaaaggcc aagtttgatg atcttgccgc tcgctactct gattgcagct ctgccaaacg      540
tggtggcgat ctcggtccct tggtcggaac cagatgcag aagcctttg aagaagcaac       600 atttgctctc aaggttggtg agatgagtga cattgtggat acggatagtg gtgtccatat      660
catcaagaga actggatgag caccgaaagt gaaacttgtt gatctttggg tgaatccaag      720
tatcttttga aacacaattt gttccttgat attattaatg cctatggctg gcactcttat      780
tgtatgaagt gatgttgtct cgttggcgtg tgagtaccta aagacggatt taagcaccgt      840
ttctgatacg gtttattctg agaatgttat ggttgtgct                            879
```

```
<210> SEQ ID NO 57
<211> LENGTH: 595
<212> TYPE: DNA
<213> ORGANISM: Lycopersicon esculentum
<220> FEATURE:
<221> NAME/KEY: misc_feature
<222> LOCATION: (1)...(595)
<223> OTHER INFORMATION: n = A,T,C or G

<400> SEQUENCE: 57
ggatcgtcgg cgatagagag tangagaaag gaatttgaaa gaaaaatggc gtcgaaccaa       60
gtgagggcat cccacatact catcaaacac gaaggatcta gacgtaaatc ttcatggaaa      120
gatccagaag gtcgcatcat ctgtaacacc accagagacg ccgccgcttc ccagctcaaa      180
tcctttcgcg atgacatcat ctccggcaag tccaagttcg aagatgttgc ttctcgcttc      240
tctgattgca gctctgccaa acgcggcggc gatctcggtc catttggtcg agggcagatg      300 cagaaaccctt ttgaagttgc aacctatgca ctggaggttg gtgagatcag cgacatcatt      360
gatactgaca gtggtgctca cataattctg agaaccggtt aacattggtg gagagagtat      420
ctaaagattc aagagcaatt gcaagttgta acgttttttt aatttttatt ttggtgtctc      480
aaagactacc caggtttgtt tcgtttttta ttttcaccac gtttgtgata aatttcgatt      540
gtattatcag tcagctacaa ctccagatgc ctgatgttta tagacgtttt aatcc           595
```

```
<210> SEQ ID NO 58
<211> LENGTH: 707
<212> TYPE: DNA
<213> ORGANISM: Digitalis lanata

<400> SEQUENCE: 58
ggcacgagtc cgatcggaag aggaagaagg cctcgatctc gtccggagat cgggctagcg       60
agcaccatca ccaccaccac aagaagcaag cgagcagcac caagaagacg aaaatgtcat      120
cggagaaggt tagggcgtcc acatactcta taaagcacca gggatcccgc cgcaagtcct      180
cctggaagga ccctgatggt agcctcatct ccgccactac ccgagacgac gctgtttctc      240
agctccaatc cctccgacaa gaactccttt ccgaccccgc tccttctcc gacctcgcct       300 cccgtcactc ccactgcagc tctgcaaagc gtggtggcga tcttggtcct tttggaaggg      360
```

```
gccagatgca gaaacctttc gaagaagcca catttgcact aaaggttggt gagataagtg    420
atatcgtgga tactgacagt ggagttcaca tcatcaagag aacaggatag caagtgatgc    480
aaaatttgca acttcagggt gctttggttg ccagattgtg tgcctatatg tgagctttgc    540
ttttttgttt gagcaacaac agactcatgt cattgtaatg cctatagccg ttccttgagg    600
ctacagtttt taatgattgt aatttattac cctattgcat ttacacacaa accaaattat    660
ctctctggct gctgtgcagt aattggtata ttattgatcc aaaaaaa                   707

<210> SEQ ID NO 59
<211> LENGTH: 1664
<212> TYPE: DNA
<213> ORGANISM: Lolium perenne

<400> SEQUENCE: 59
tctcctctct cctctctctc cccccacatc ttgtctttcc ctttgccact tcccaagaca     60
cacgccgata cagtgagagag agagcggcgc cttctcctcc attggcgcat cttcatctag   120
gccacagccg gagggaaaga gcagcaacct ttaggcccca agaacgccga tccttgcgaa    180
agaaccaaat actactcccc aaccccaagt gatagcggcg gcggctgttt cttgcgatct    240
tgagatgggt atcctctgct tcggtgcttc ctccaccctg ctctgcgggg aggacaggaa    300
cagcgtcctc ggcctgggcg gctgcggcgg cgacggcgac ggcgaggtgg tggaggcggg    360
gagcggcctg gatttcttgg aggccggcgc tctgttccca gtggactgtg acgaggtcgt    420
gggggtgctg gtgctcaagg agatcgatca tcagcccaag ggcggctatg tggagagatt    480
ggagcaagga ggattcgagt cttcctggag gaaagatgcc atggattgga tttgcaaggt    540
ccattcctac tacaattttg gaccactcag cctctgcctc tcggtgaact acctggatcg    600
gttcctctcc acgtttaatc tccctcatga caaatcttgg atgcaacagt tgatgtcagt    660
tgcctgccta tctcttgctg tcaagatgga ggagactgtg gcccctcttc ctgtagacct    720
tcaggtctgt ggcgcgaaga acatgtttga agcaaagaac attaagagga tggagctcgt    780
tgtgatggag accctgaatt ggagattgca cgccgtgacc ccattctctt tcatctgcta    840
cttcttggac aagttcaccg aagggaagcc gccgagttac atgctggcct cacggtgcgc    900
cgagctcatt gttggcactg tgaaagacta cagattcttg tcattcagac cttctgagat    960
tgctgccgca gtggttctat ggcgctcgt tgagaatcag gttattggct tcagcagtgc   1020
cattgcagca tctgaaatcc ctgtaaataa ggagatgatt atgagatgct atgagctgtt   1080
ggtgaggatg agagggaact tgagtgcaag cctttcagcg ccgcagagcc cgatcggtgt   1140
gctggatgca gcatgcttca gctttaggag cgatgacaca acaccaggat catcgccatc   1200
aaacaataac aacagcggca acaacgatca ggcctctgct ccggcttcga agaagagaag   1260
gctaagcaca tcaccaatct gatacaacgt acatatatat tactcggcac tgctcccggc   1320
ttgttcattc gattatcatc ttatccccaa agcccatcag tcatcagggt aacaagttgt   1380
ggtgcaatag taattatagt gagcattgtg ccgattagag aaatgtgggc agcaataagg   1440
ttagtaccgg cttcttgaac tctgaaagag gagaggaggg tgtgtgcgtt gatgggagga   1500
gggagtcttc ttcctcttac aattttgtct ccccccttctt catttttaatt atttatttat   1560 tttctttttt tccttctctg ggggctactc caggagatca ttgtggatat gagatggaag   1620
atgtgagaaa atcagcaaaa ttggattttc gtttaaaaaa aaaa                    1664

<210> SEQ ID NO 60
<211> LENGTH: 345
```

```
<212> TYPE: PRT
<213> ORGANISM: Lolium perenne

<400> SEQUENCE: 60
```

| | | | | | | | | | | | | | | |
|---|---|---|---|---|---|---|---|---|---|---|---|---|---|---|
|Met|Gly|Ile|Leu|Cys|Phe|Gly|Ala|Ser|Ser|Thr|Leu|Leu|Cys|Gly|Glu
|1| | | |5| | | | |10| | | | |15|

Asp Arg Asn Ser Val Leu Gly Leu Gly Gly Cys Gly Gly Asp Gly Asp
            20                  25                  30

Gly Glu Val Val Glu Ala Gly Ser Gly Leu Asp Phe Leu Glu Ala Gly
                35                  40                  45

Ala Leu Phe Pro Val Asp Cys Asp Glu Val Val Gly Val Leu Val Leu
 50                  55                  60

Lys Glu Ile Asp His Gln Pro Lys Gly Gly Tyr Val Glu Arg Leu Glu
 65                  70                  75                  80

Gln Gly Gly Phe Glu Ser Ser Trp Arg Lys Asp Ala Met Asp Trp Ile
                85                  90                  95

Cys Lys Val His Ser Tyr Tyr Asn Phe Gly Pro Leu Ser Leu Cys Leu
                100                 105                 110

Ser Val Asn Tyr Leu Asp Arg Phe Leu Ser Thr Phe Asn Leu Pro His
                115                 120                 125

Asp Lys Ser Trp Met Gln Gln Leu Met Ser Val Ala Cys Leu Ser Leu
                130                 135                 140

Ala Val Lys Met Glu Glu Thr Val Ala Pro Leu Pro Val Asp Leu Gln
145                 150                 155                 160

Val Cys Gly Ala Lys Asn Met Phe Glu Ala Lys Asn Ile Lys Arg Met
                165                 170                 175

Glu Leu Val Val Met Glu Thr Leu Asn Trp Arg Leu His Ala Val Thr
                180                 185                 190

Pro Phe Ser Phe Ile Cys Tyr Phe Leu Asp Lys Phe Thr Glu Gly Lys
                195                 200                 205

Pro Pro Ser Tyr Met Leu Ala Ser Arg Cys Ala Glu Leu Ile Val Gly
                210                 215                 220

Thr Val Lys Asp Tyr Arg Phe Leu Ser Phe Arg Pro Ser Glu Ile Ala
225                 230                 235                 240

Ala Ala Val Val Leu Leu Ala Leu Val Glu Asn Gln Val Ile Gly Phe
                245                 250                 255

Ser Ser Ala Ile Ala Ala Ser Glu Ile Pro Val Asn Lys Glu Met Ile
                260                 265                 270

Met Arg Cys Tyr Glu Leu Leu Val Arg Met Arg Gly Asn Leu Ser Ala
                275                 280                 285

Ser Leu Ser Ala Pro Gln Ser Pro Ile Gly Val Leu Asp Ala Ala Cys
                290                 295                 300

Phe Ser Phe Arg Ser Asp Asp Thr Thr Pro Gly Ser Ser Pro Ser Asn
305                 310                 315                 320

Asn Asn Asn Ser Gly Asn Asn Asp Gln Ala Ser Ala Pro Ala Ser Lys
                325                 330                 335

Lys Arg Arg Leu Ser Thr Ser Pro Ile
                340                 345